(12) United States Patent
Constien et al.

(10) Patent No.: US 9,433,681 B2
(45) Date of Patent: Sep. 6, 2016

(54) LIPIDS AND COMPOSITIONS FOR INTRACELLULAR DELIVERY OF BIOLOGICALLY ACTIVE COMPOUNDS

(71) Applicant: AXOLABS GMBH, Kulmbach (DE)

(72) Inventors: Rainer Constien, Kulmbach (DE); Anke Geick, Bayreuth (DE); Philipp Hadwiger, Kulmbach (DE); Torsten Haneke, Kulmbach (DE); Ludger Markus Ickenstein, Kulmbach (DE); Carla Alexandra Hernandez Prata, Kulmbach (DE); Andrea Schuster, Bayreuth (DE); Timo Weide, Kulmbach (DE)

(73) Assignee: AXOLABS GMBH, Kulmbach (DE)

( * ) Notice: Subject to any disclaimer, the term of this patent is extended or adjusted under 35 U.S.C. 154(b) by 267 days.

(21) Appl. No.: 14/178,538

(22) Filed: Feb. 12, 2014

(65) Prior Publication Data

US 2014/0162962 A1    Jun. 12, 2014

Related U.S. Application Data

(62) Division of application No. 13/466,640, filed on May 8, 2012, now Pat. No. 8,691,750.

(30) Foreign Application Priority Data

May 17, 2011    (EP) ..................................... 11166353

(51) Int. Cl.
| | | |
|---|---|---|
| *C07C 211/22* | (2006.01) | |
| *C07D 295/30* | (2006.01) | |
| *C07D 241/04* | (2006.01) | |
| *A61K 31/713* | (2006.01) | |
| *A61K 31/7088* | (2006.01) | |
| *C07C 211/11* | (2006.01) | |
| *C07C 211/13* | (2006.01) | |
| *A61K 47/18* | (2006.01) | |
| *A61K 31/575* | (2006.01) | |
| *A61K 31/70* | (2006.01) | |
| *B82Y 5/00* | (2011.01) | |
| *C07C 217/42* | (2006.01) | |
| *C07C 211/14* | (2006.01) | |
| *C07C 217/08* | (2006.01) | |
| *C07C 217/28* | (2006.01) | |
| *A61K 9/127* | (2006.01) | |
| *A61K 9/14* | (2006.01) | |
| *A61K 38/02* | (2006.01) | |
| *A61K 47/22* | (2006.01) | |
| *A61K 39/00* | (2006.01) | |

(52) U.S. Cl.
CPC ............. *A61K 47/18* (2013.01); *A61K 9/1271* (2013.01); *A61K 9/145* (2013.01); *A61K 31/575* (2013.01); *A61K 31/70* (2013.01); *A61K 31/7088* (2013.01); *A61K 31/713* (2013.01); *A61K 38/02* (2013.01); *A61K 39/00* (2013.01); *A61K 47/22* (2013.01); *B82Y 5/00* (2013.01); *C07C 211/11* (2013.01); *C07C 211/13* (2013.01); *C07C 211/14* (2013.01); *C07C 211/22* (2013.01); *C07C 217/08* (2013.01); *C07C 217/28* (2013.01); *C07C 217/42* (2013.01); *C07D 241/04* (2013.01); *C07D 295/30* (2013.01)

(58) Field of Classification Search
CPC ...... A61K 47/18; A61K 39/00; A61K 38/02; A61K 9/145; A61K 31/575; A61K 31/7088; A61K 47/22; A61K 31/713; A61K 31/70; A61K 9/1271; C07D 295/30; C07D 241/04; C07C 211/22; C07C 211/13; C07C 211/11; C07C 217/42; C07C 211/14; C07C 217/28; C07C 217/08; B82Y 5/00
See application file for complete search history.

(56) References Cited

U.S. PATENT DOCUMENTS

| | | | |
|---|---|---|---|
| 5,948,902 | A | 9/1999 | Honkanen et al. |
| 8,691,750 | B2 | 4/2014 | Constien et al. |
| 2006/0148904 | A1 | 7/2006 | Protopopova et al. |
| 2012/0295832 | A1 | 11/2012 | Constien et al. |
| 2014/0162934 | A1 | 6/2014 | Constien et al. |
| 2014/0170175 | A1 | 6/2014 | Constien et al. |

FOREIGN PATENT DOCUMENTS

| | | | |
|---|---|---|---|
| JP | 07017138 A | * | 1/1995 |
| WO | WO 2007/111993 A2 | | 10/2007 |
| WO | WO 2010/053572 A2 | | 5/2010 |

OTHER PUBLICATIONS

Smith, D. R.,"Preparation of Symmetrical N, N'-Disubstituted Piperazines and their Quaternary Ammonium Salts." Journal of the American Chemical Society 72.7 (1950): 2969-2970.*
De Fougerolles et al., "Interfering with disease: a progress report on siRNA-based therapeutics" Nature Reviews Drug Discovery, vol. 6, Jun. 2007, pp. 443-453.
Robbins et al., "siRNA and Innate Immunity" Oligonucleotides, vol. 19, No. 2, Mar. 11, 2009, pp. 89-101.
Soutschek et al., "Therapeutic silencing of an endogenous gene by systemic administration of modified siRNAs" Nature, vol. 432, Nov. 11, 2004, pp. 173-178.
Zimmermann et al., "RNAI-mediated gene silencing in non-human primates" Nature, 2006, pp. 1-4.
Akinc et al., "A combinatorial library of lipid-like materials for delivery of RNAI therapeutics" Nature Biotechnology, Apr. 27, 2008, pp. 1-9.
Love et al., "Lipid-like materials for low-dose, in vivo gene silencing" Proceedings of the National Academy of Sciences, vol. 107, No. 5, Feb. 2, 2010, pp. 1864-1869.
Heyes et al., "Cationic lipid saturation influences intracellular delivery of encapsulated nucleic acids" Journal of Controlled Release, vol. 107, Jul. 28, 2005, pp. 276-287.
Semple et al., "Rational design of cationic lipids for siRNA delivery" Nature Biotechnology, vol. 28, No. 2, Jan. 17, 2010, pp. 172-176.
MacLachlan et al., "Progress towards a synthetic virus for systemic gene therapy" Current Opinion in Molecular Therapeutics, vol. 1, No. 2, 1999, pp. 252-259.

(Continued)

*Primary Examiner* — Samantha Shterengarts
*Assistant Examiner* — Matt Mauro
(74) *Attorney, Agent, or Firm* — Medler Ferro Woodhouse & Mills PLLC

(57) ABSTRACT

The present invention provides novel amino-lipids, compositions comprising such amino-lipids and methods of producing them. In addition, lipid nanoparticles comprising the novel amino-lipids and a biologically active compound are provided, as well as methods of production and their use for intracellular drug delivery.

21 Claims, 23 Drawing Sheets

(56) References Cited

OTHER PUBLICATIONS

Soni et al., "Biodistribution, Stability, and Antiviral Efficacy of Liposome-Entrapped Phosphorothioate Antisense Oligodeoxynucleotides in Ducks for the Treatment of Chronic Duck Hepatitis B Virus Infection" Hepatology, vol. 28, No. 5, 1996, p. 1402-1410.

Felgner et al., "Lipofection: a highly efficient, lipid-mediated DNA-transfection procedure" Proceedings of the National Academy of Sciences, vol. 84, Nov. 1967, Biochemistry pp. 7413-7417.

Olson et al., "Preparation of Liposomes of Defined Size Distribution by Extrusion through Polycarbonate Membranes" Biochimica et Biophysica Acta—Biomembranes, vol. 557, 1979, pp. 9-23.

Szoka et al., "Preparation of Unllamellar Liposomes of Intermediate Size (0.1-0.2 μm) by a Combination of Reverse Phase Evaporation and Extrusion through Polycarbonate Membranes" Biochimica et Biophysica Acta—Biomembranes, vol. 601, 1980, pp. 559-571.

Vemuri et al., "Preparation and characterization of liposomes as therapeutic delivery systems: a review" Pharmaceutica Acta Halvetiae, vol. 70, 1995, pp. 95-111.

Watwe et al., "Manufacture of liposomes: A review" Current Science, vol. 68, No. 7, Apr. 10, 1995, pp. 715-724.

Riaz et al., "Liposomes Preparation Methods" Pakistan Journal of Pharmaceutical Sciences, vol. 19, No. 1, 1996, p. 65-77.

Podesta et al., "Chapter Seventeen—Engineering Cationic Liposome: siRNA Complexes for In Vitro and In Vivo Delivery" Methods in Enzymology, vol. 464, 2009, pp. 343-354.

Bajaj et al., "Structure-Activity Investigation on the Gene Transfection Properties of Cardiolipin Mimicking Gemini Lipid Analogues" Bioconjugate Chemistry, vol. 19, No. 6, May 29, 2008, p. 1283-1300.

Piancatelli et al., "Pyridinium Chlorochromate: A Versatile Oxidant in Organic Synthesis" Synthesis, Apr. 1982, pp. 245-258.

Abdel-Magid et al., "Reductive Amination of Aldehydes and Ketones with Sodium Triacetoxyborohydride. Studies on Direct and Indirect Reductive Amination Procedures" Journal of Organic Chemistry, vol. 61, No. 11, pp. 3849-3862.

Wincott et al. "Synthesis, deprotection, analysis and purification of RNA and ribozymes" Nucleic Acids Research, vol. 23, No. 14, 1995, p. 2677-2684.

Non-Final Office Action issued in related U.S. Appl. No. 14/178,538, mailed Apr. 10, 2015.

Notice of Allowance issued in related U.S. Appl. No. 14/178,538, mailed Jul. 17, 2015.

* cited by examiner

A. KL5, mol. wt. 1149

B. KL6, mol. wt. 611.1

C. KL7, mol. wt. 1192.1

D. KL8, mol. wt. 1191.1

E. KL9, mol. wt. 1155.3

F. KL10, mol. wt. 985.9

G. KL12, mol. wt. 1035

H. KL15, mol. wt. 1036.1

I. KL16, mol. wt. 1080

J. KL22, mol. wt. 1037

K. KL23, mol. wt. 973

L. KL24, mol. wt. 1284

M. KL25, mol. wt. 904

N. KL26, mol. wt. 861

O. KL27, mol. wt. 509

P. KL28, mol. wt. 481

Q. KL30, mol. wt. 1015

R. KL32, mol. wt. 1236.2

S. KL33, mol. wt. 1477.8

T. KL34, mol. wt. 1467.7

U. KL35, mol. wt. 1457.6

W. KL36, mol. wt. 774.4

X. KL37, mol. wt. 1372.5

Y. KL39, mol. wt. 1279.3

Z. KL43, mol. wt. 846.8

AA. KL44, mol. wt. 905.0

BB. KL45, mol. wt. 929.0

CC. KL47, mol. wt. 646.8

DD. KL49, mol. wt. 1168.1

EE. KL51, mol. wt. 845.6

FF. KL52, mol. wt. 700.7

GG. KL53, mol. wt. 1126.1

HH. KL56, mol. wt. 1196.3

II. KL58, mol. wt. 959.8

LIPIDS AND COMPOSITIONS FOR INTRACELLULAR DELIVERY OF BIOLOGICALLY ACTIVE COMPOUNDS

CROSS-REFERENCE TO RELATED APPLICATIONS

The present application is a divisional of U.S. Ser. No. 13/466,640, filed May 8, 2012, which claims benefit of EP 11166353, filed May 17, 2011, the entire disclosures of which are incorporated by reference herein.

FIELD OF THE INVENTION

The present invention provides novel amino-lipids, compositions comprising such amino-lipids and methods of producing them. In addition, lipid nanoparticles (LNPs) comprising the novel amino-lipids and a biologically active compound are provided, as well as methods of production and their use for intracellular drug delivery.

BACKGROUND OF THE INVENTION

Lipid nanoparticles (LNPs), liposomes or lipoplexes are effective drug delivery systems for biologically active compounds such as therapeutic proteins, peptides or nucleic acid based therapeutics, which are otherwise cell impermeable. Liposomal formulations have also been developed 15 for small molecule drugs with the aim to enrich the drug in certain tissues.

Drugs based on nucleic acids interact with a messenger RNA or a gene and have to be delivered to the proper cellular compartment in order to be effective. In particular double stranded nucleic acids, for example double stranded RNA molecules (dsRNA) such as siRNAs, suffer from their physico-chemical properties that render them impermeable to cells. Upon delivery into the proper compartment, siRNAs block gene expression through a highly conserved regulatory mechanism known as RNA interference (RNAi). Typically, siRNAs are large in size with a molecular weight ranging from 12·17 kDa, and are highly anionic due to their phosphate backbone with up to 50 negative charges. In addition, the two complementary RNA strands result in a rigid helix. These 25 features contribute to the siRNA's poor "drug-like" properties (*Nature Reviews, Drug Discovery* 2007, 6:443). When administered intravenously, the siRNA is rapidly excreted from the body with a typical half-life in the range of only 10 min. Additionally, siRNAs are rapidly degraded by nucleases present in blood and other fluids or in tissues, and have been shown to stimulate strong immune responses in vitro and in vivo (*Oligonucleotides* 2009, 19:89).

By introduction of appropriate chemical modifications stability towards nucleases can be increased and at the same time immune stimulation can be suppressed. Conjugation of lipophilic small molecules to the siRNAs improves the pharmacokinetic characteristics of the double stranded RNA molecule. It has been demonstrated that these small molecule siRNA conjugates are efficacious in a specific down regulation of a gene expressed in hepatocytes of rodents. However, in order to elicit the desired biologic effect a large dose was needed (*Nature* 2004, 432:173).

With the advent of lipid nanoparticle formulations the siRNA doses necessary to achieve target knockdown in vivo could be significantly reduced (*Nature* 2006, 441:111). Typically, such lipid nanoparticle drug delivery systems are multi-component formulations comprising cationic lipids, helper lipids, lipids containing polyethylene glycol and cholesterol. The positively charged cationic lipids bind to the anionic nucleic acid, while the other components support a stable self-assembly of the lipid nanoparticles.

To improve delivery efficacy of these lipid nanoparticle formulations, many efforts are directed to develop more appropriate cationic lipids. These efforts include high throughput generation of cationic lipid libraries based on solvent- and protecting group free chemical reaction such as Michael additions of amines to acrylamides or acrylates (*Nature Biotechnology* 2008, 26:561) or ring-opening reactions with mines and terminal epoxides (*PNAS* 2010, 107: 1854). Another strategy involves structure activity studies, e.g. systematic variation of the degree of saturation in the hydrophobic part (*Journal of Controlled Release* 2005, 107:276) or the polar head group of the cationic lipid (*Nature Biotechnology* 2010, 28:172) resulting in an improved efficacy of the so-called stable nucleic acid-lipid particles (SNALP) technology (*Current Opinion in Molecular Therapeutics* 1999, 1:252).

Despite these efforts, improvements in terms of increased efficacy and decreased toxicity are still needed, especially for lipid nanoparticle based drug delivery systems intended for therapeutic uses. LNPs naturally accumulate in the liver after intravenous injection into an animal (*Hepatology* 1998, 28:1402). It has been demonstrated that gene silencing can be achieved in vivo in hepatocytes which account for the majority of the cells in the liver. Even the simultaneous down-modulation of several target genes expressed in hepatocytes could be successfully achieved (*PNAS* 2010, 107:1854). However, evidence of successful gene regulation in other liver cell types is lacking.

SUMMARY OF THE INVENTION

The present invention provides novel amino-lipids, compositions comprising the inventive amino-lipids, as well as methods of producing them. In particular, compositions comprising the amino-lipids of the invention that form lipid nanoparticles (LNPs) are provided, as well as methods of producing and their use for the intracellular delivery of biologically active compounds, for example nucleic acids.

The methods of producing the amino-lipids provided herein are advantageous compared to those known in prior art as the amino-lipids can be produced with a higher yield and increased purity.

The lipid nanoparticles (LNPs) comprising the inventive amino-lipids significantly enhance the intracellular delivery of nucleic acids into hepatocytes compared to LNPs comprising lipids known in prior art. In addition, the lipid nanoparticles (LNPs) comprising the inventive amino-lipids enable inhibition of gene expression in additional liver cell types apart from hepatocytes, such as Kupffer cells, Stellate cells and endothelial cells. Moreover, the lipid nanoparticles (LNPs) comprising the inventive amino-lipids are suitable for cell-type specific delivery of nucleic acids into various organs in vivo, including jujunum, liver, kidney, lung and spleen. Importantly, these lipid nanoparticles can also be administered via the air ways enabling gene silencing in the lung.

DETAILED DESCRIPTION OF THE INVENTION

Figure 1:
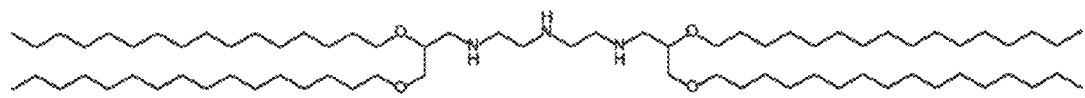
FIG. 1. Structures representing amino-lipids of the invention.
Figure 1:
Figure 1:
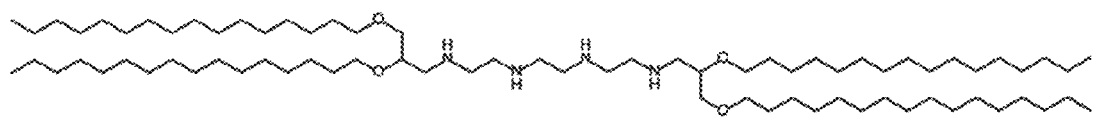
Figure 1:
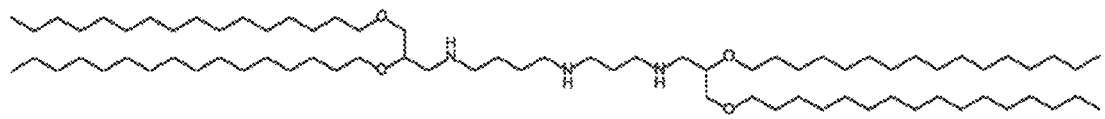
Figure 1:
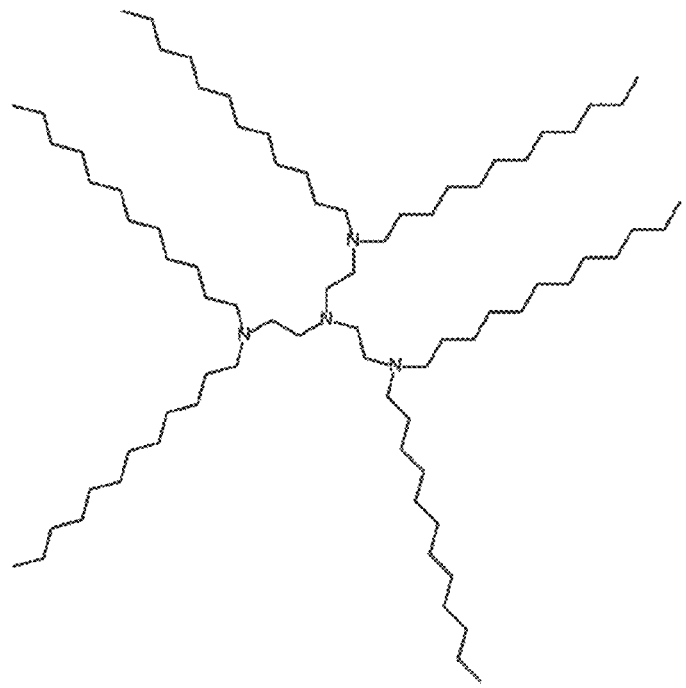
Figure 1:
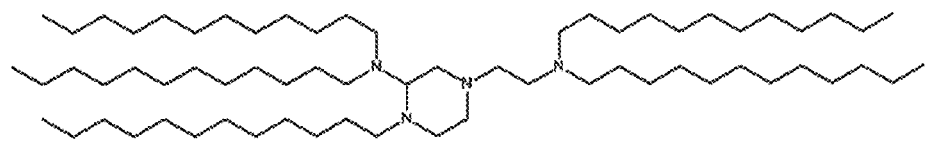
Figure 1:
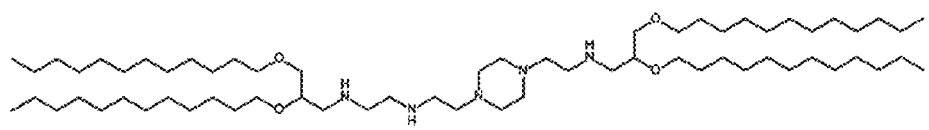
Figure 1:
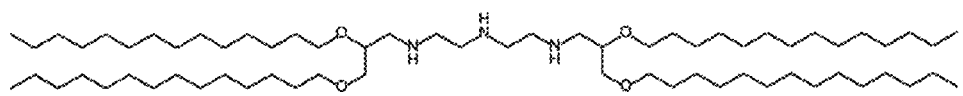
Figure 1:
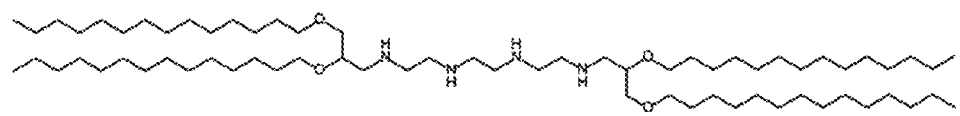
Figure 1:
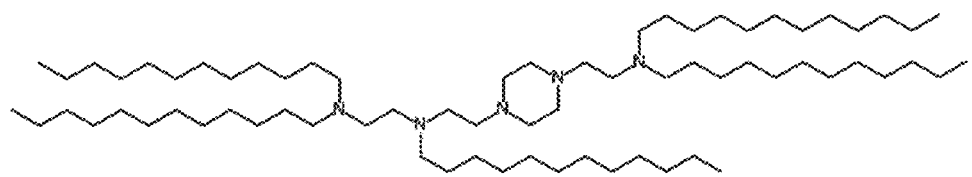
Figure 1:
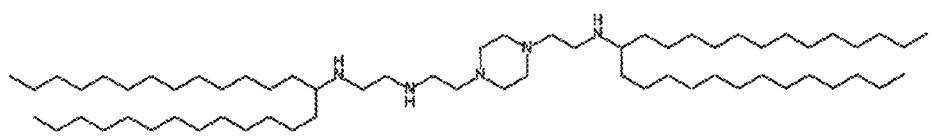
Figure 1:
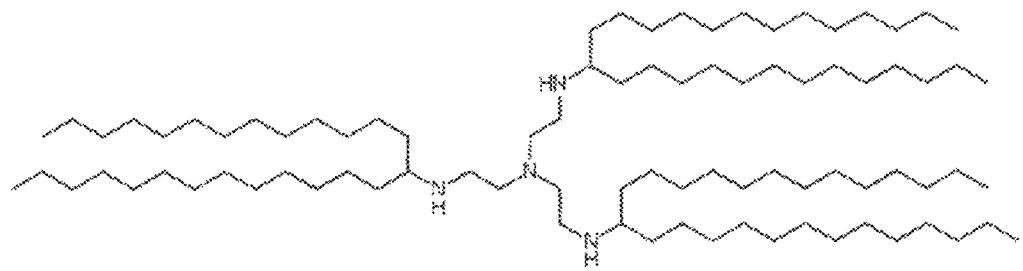
Figure 1:
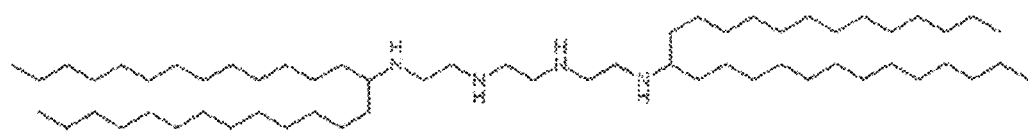
Figure 1:
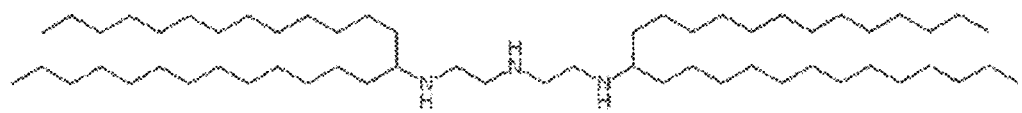
Figure 1:
Figure 1:
Figure 1:
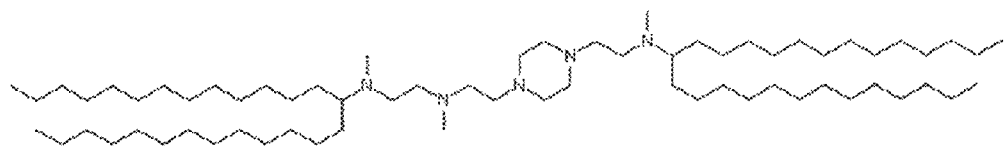
Figure 1:
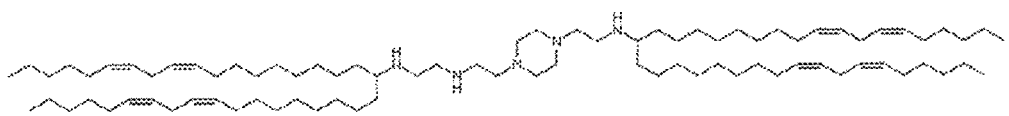
Figure 1:
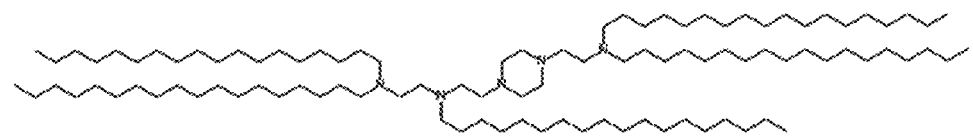
Figure 1:
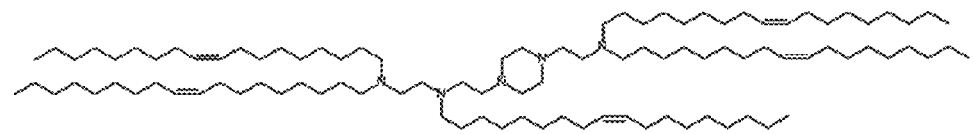
Figure 1:
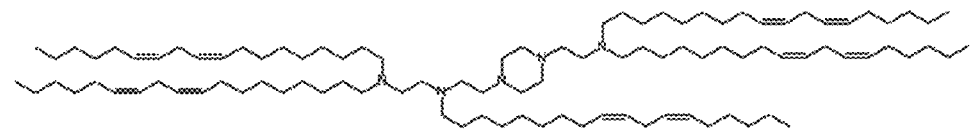
Figure 1:
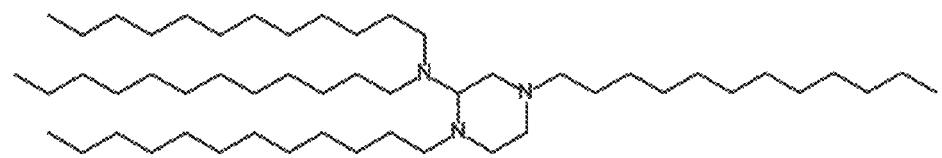
Figure 1:
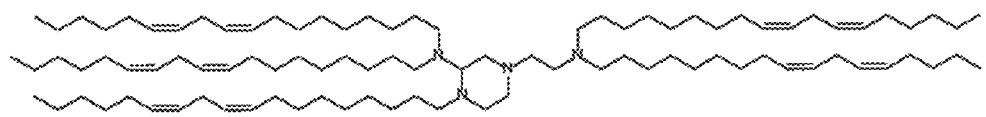
Figure 1:
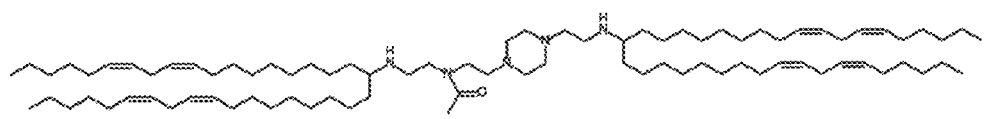
Figure 1:
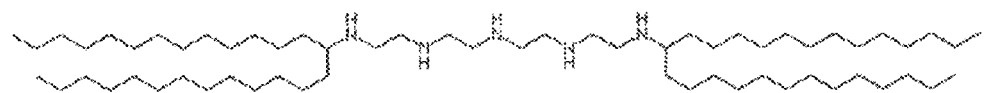
Figure 1:
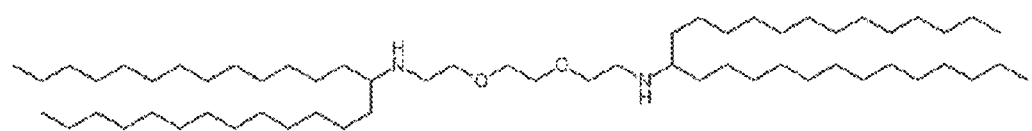
Figure 1:
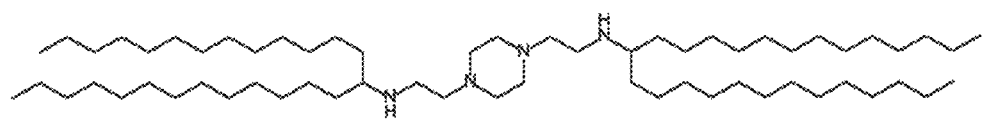
Figure 1:
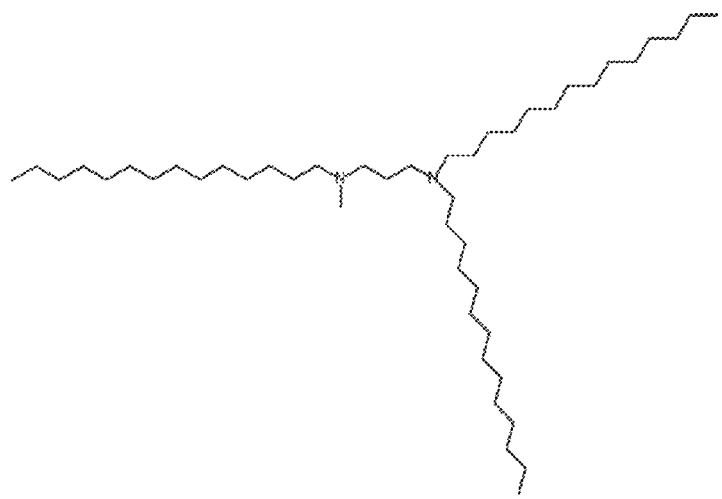
Figure 1:
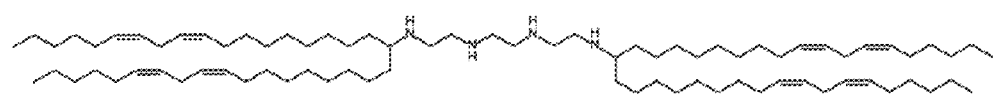
Figure 1:
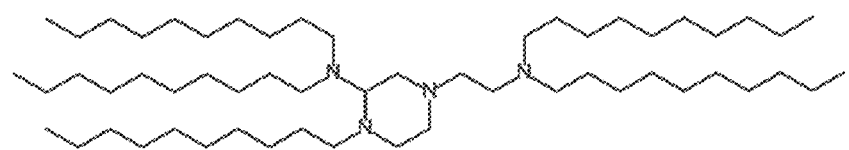
Figure 1:
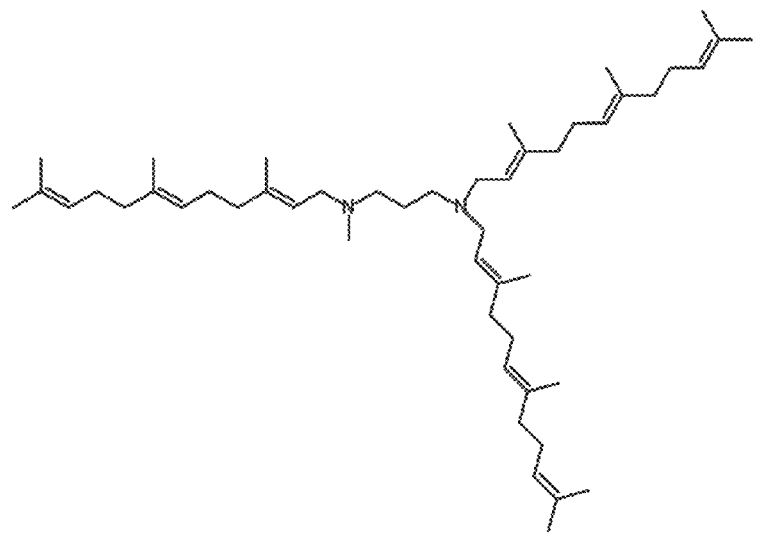
Figure 1:
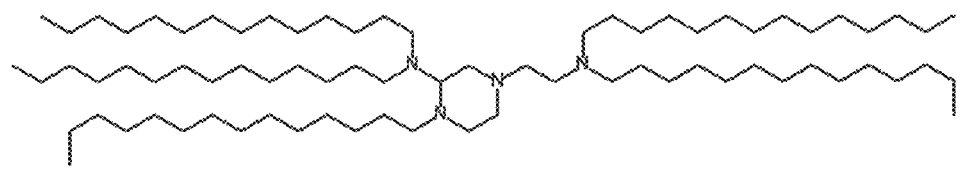
Figure 1:
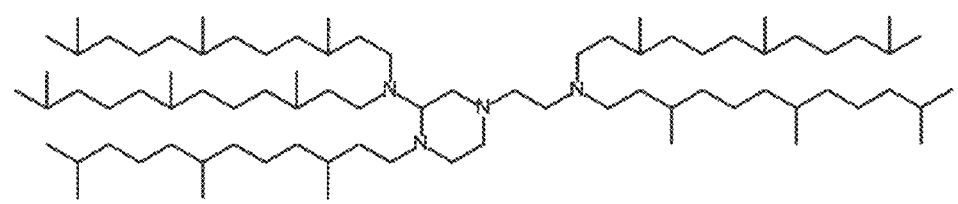
Figure 1:
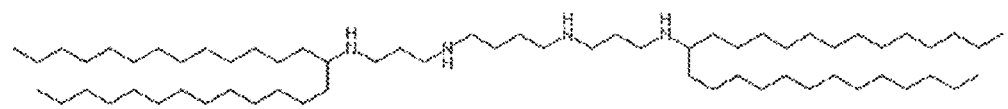
Figure 2:
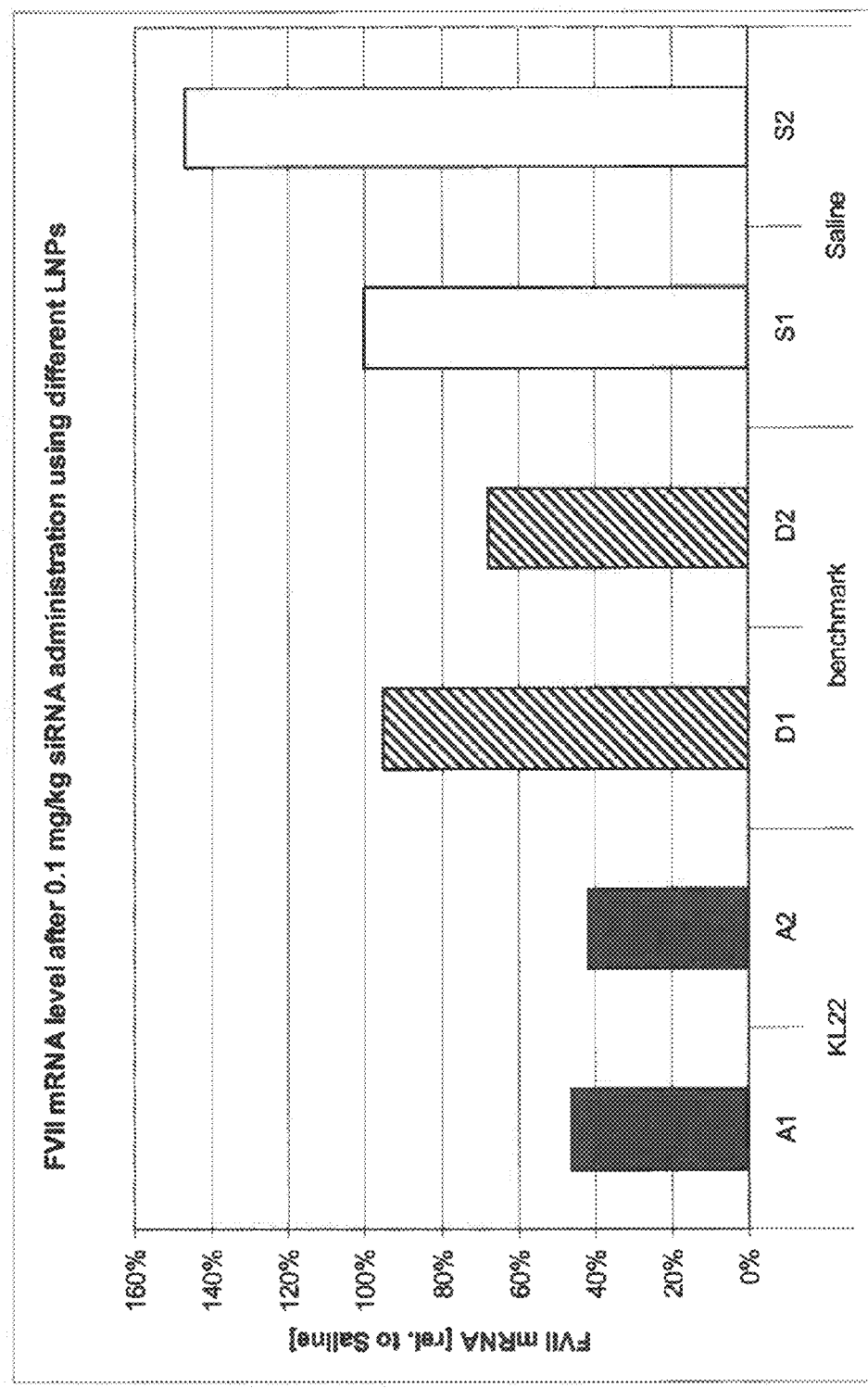
FIG. 2. Bar graph illustrating improved LNP composition of the invention to reduce FVII mRNA levels in mice.
Figure 3:
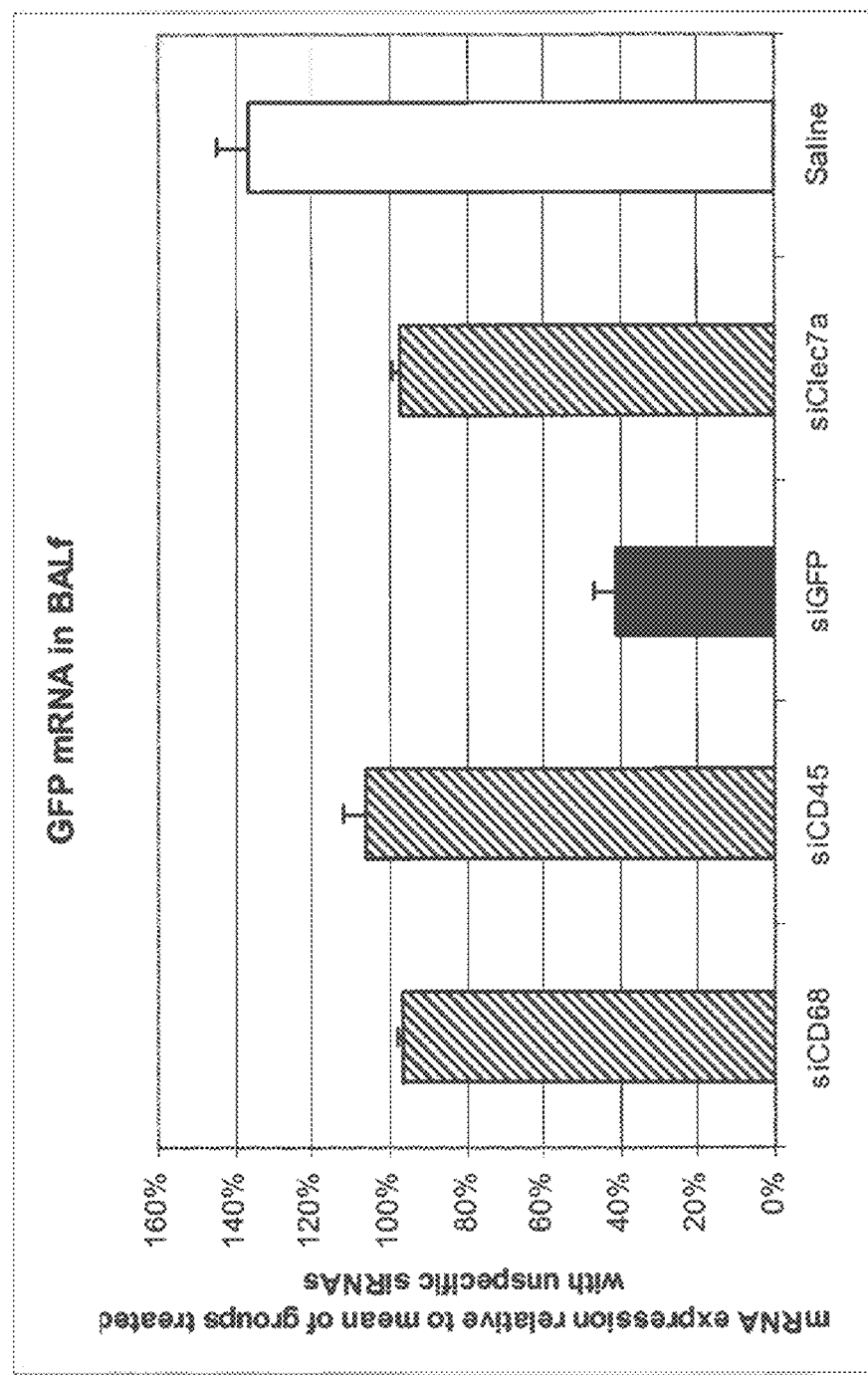
FIG. 3. Graph illustrating GFP mRNA levels after orotracheal instillation of LNPs of the present invention into GFP transgenic mice (n=4). Individual siRNAs directed against the targets indicated below the bars were formulated into LNPs consisting of 50% KL25, 10% DSPC, 38.5% cholesterol and 1.5% PEG2000-c-DOMG. 48 h post administration animals were killed, bronchoalveolar lavage fluid (BALf) prepared and the GFP mRNA level determined using bDNA assay. Hatched bars represent GFP mRNA levels of animals treated with the unspecific siRNAs.
Figure 4:
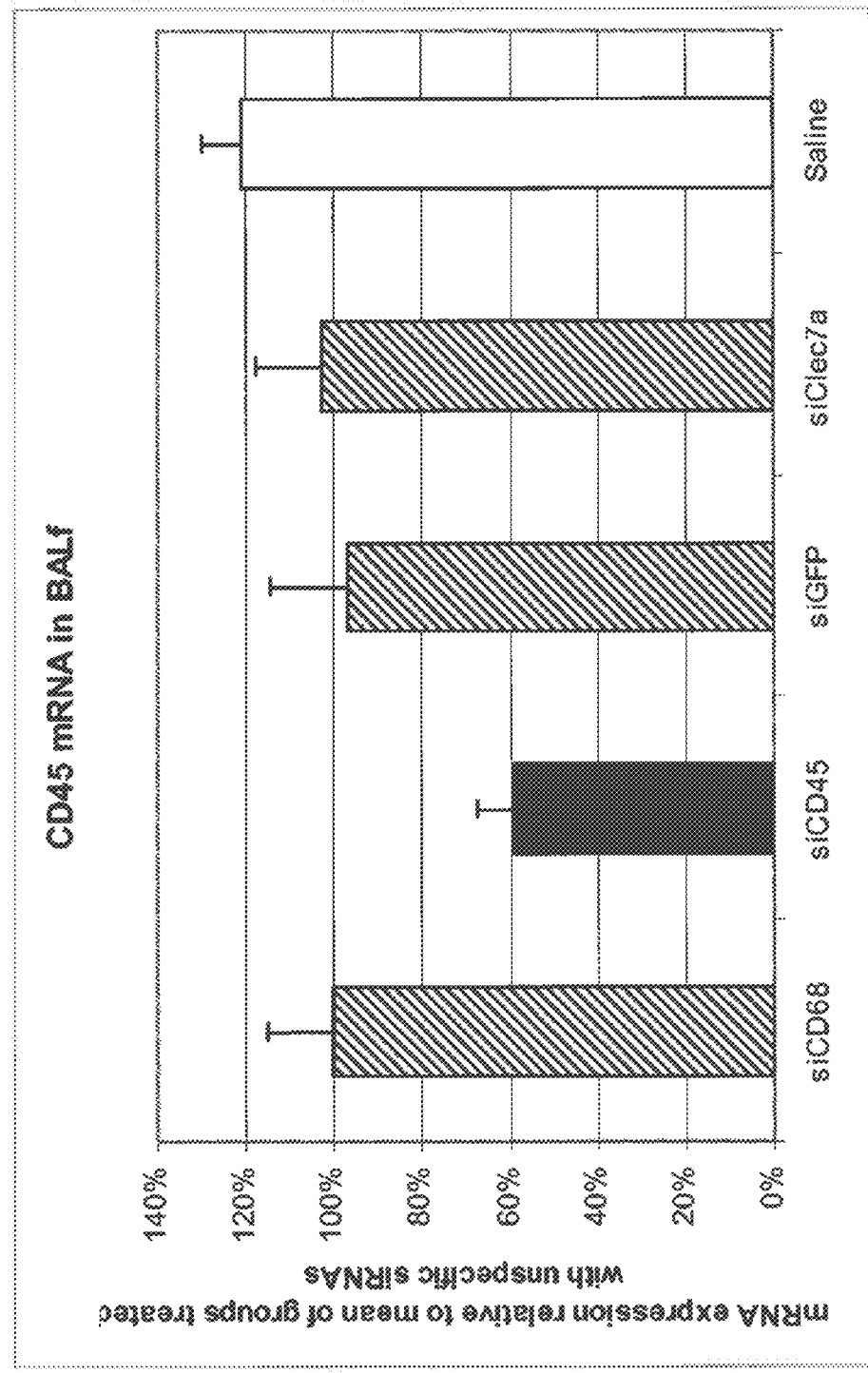
FIG. 4. Graph illustrating CD45 mRNA levels after orotracheal instillation of LNPs of the present invention into GFP transgenic mice (n=4). Individual siRNAs directed against the targets indicated below the bars were formulated into LNPs consisting of 50% KL25, 10% DSPC, 38.5% cholesterol and 1.5% PEG2000-c-DOMG. 48 h post administration animals were killed, bronchoalveolar lavage fluid (BALf) prepared and the CD45 mRNA level determined using bDNA assay. Hatched bars represent CD45 mRNA levels of animals treated with the unspecific siRNAs.
Figure 5:
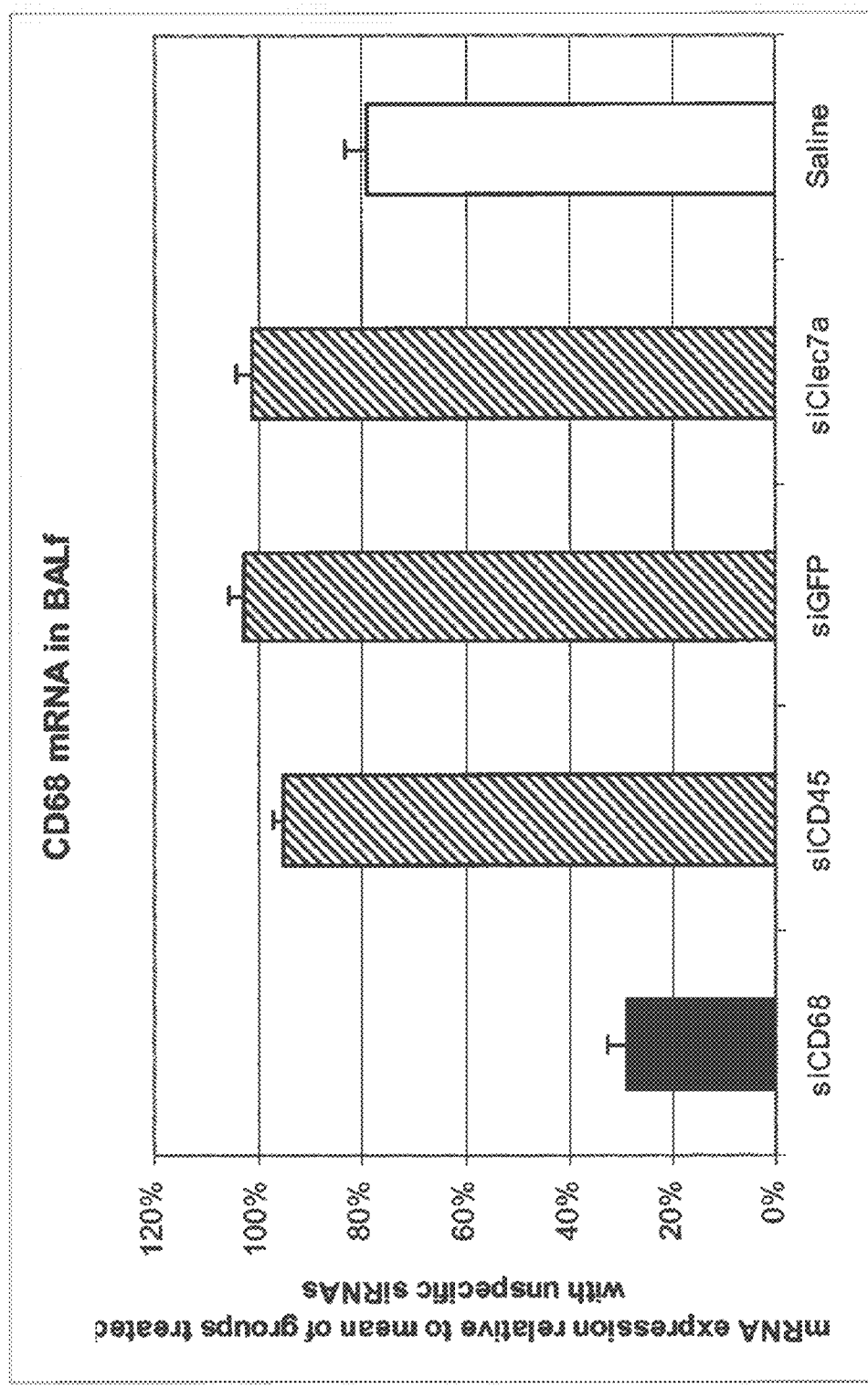
FIG. 5. Graph illustrating CD68 mRNA levels after orotracheal instillation of LNPs of the present invention into GFP transgenic mice (n=4). Individual siRNAs directed against the targets indicated below the bars were formulated into LNPs consisting of 50% KL25, 10% DSPC. 38.5% cholesterol and 1.5% PEG2000-c-DOMG. 48 h post administration animals were killed, bronchoalveolar lavage fluid (BALf) prepared and the CD68 mRNA level determined using bDNA assay. Hatched bars represent CD68 mRNA levels of animals treated with the unspecific siRNAs.
Figure 6:
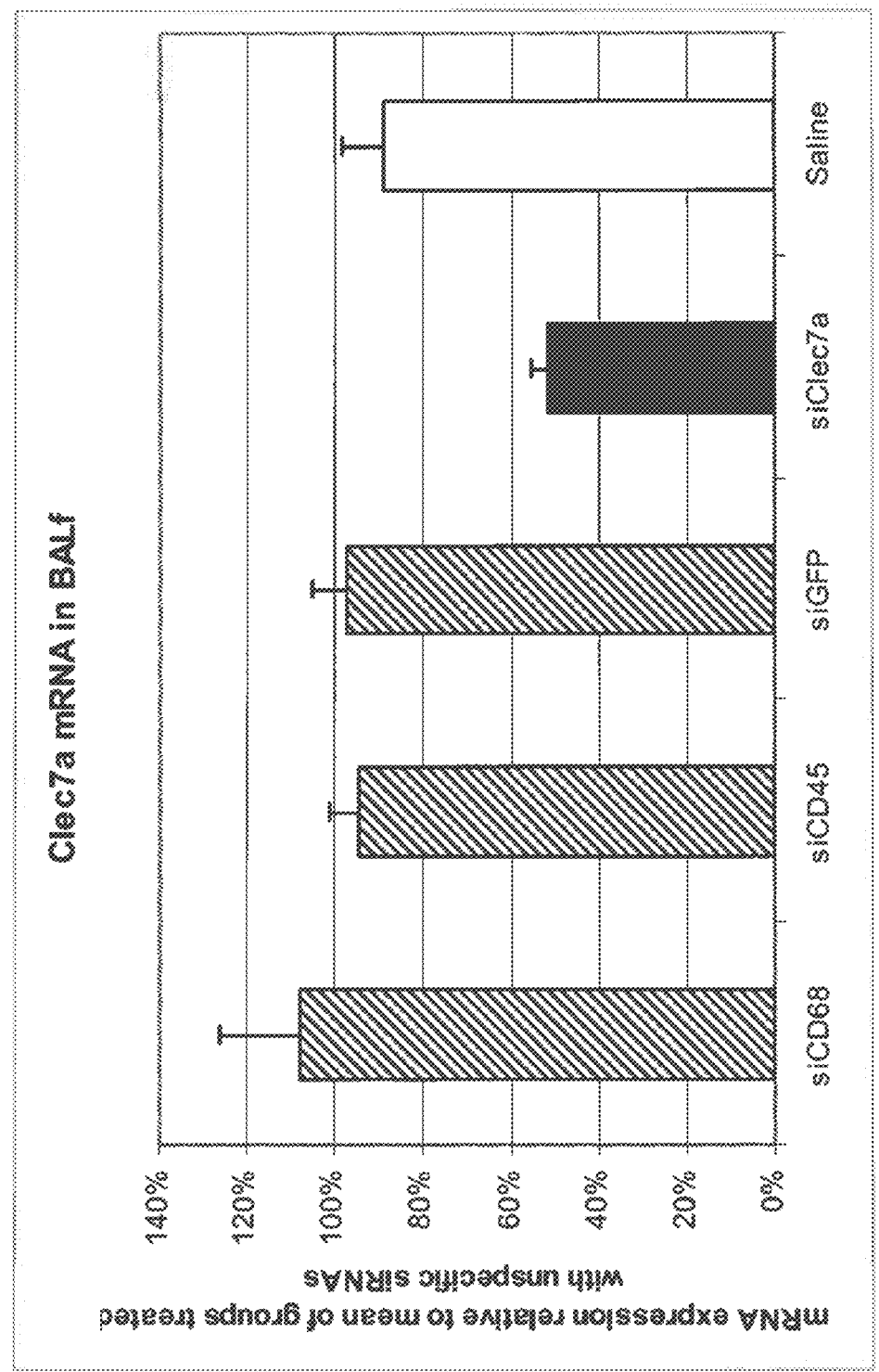
FIG. 6. Graph illustrating Clec7a mRNA levels after orotracheal instillation of LNPs of the present invention into GFP transgenic mice (n=4). Individual siRNAs directed against the targets indicated below the bars were formulated into LNPs consisting of 50% KL25, 10% DSPC, 38.5% cholesterol and 1.5% PEG2000-c-DOMG. 48 h post administration animals were killed, bronchoalveolar lavage fluid (BALf) prepared and the Clec7a mRNA level determined using bDNA assay. Hatched bars represent Clec7a mRNA levels of animals treated with the unspecific siRNAs.
Figure 7:
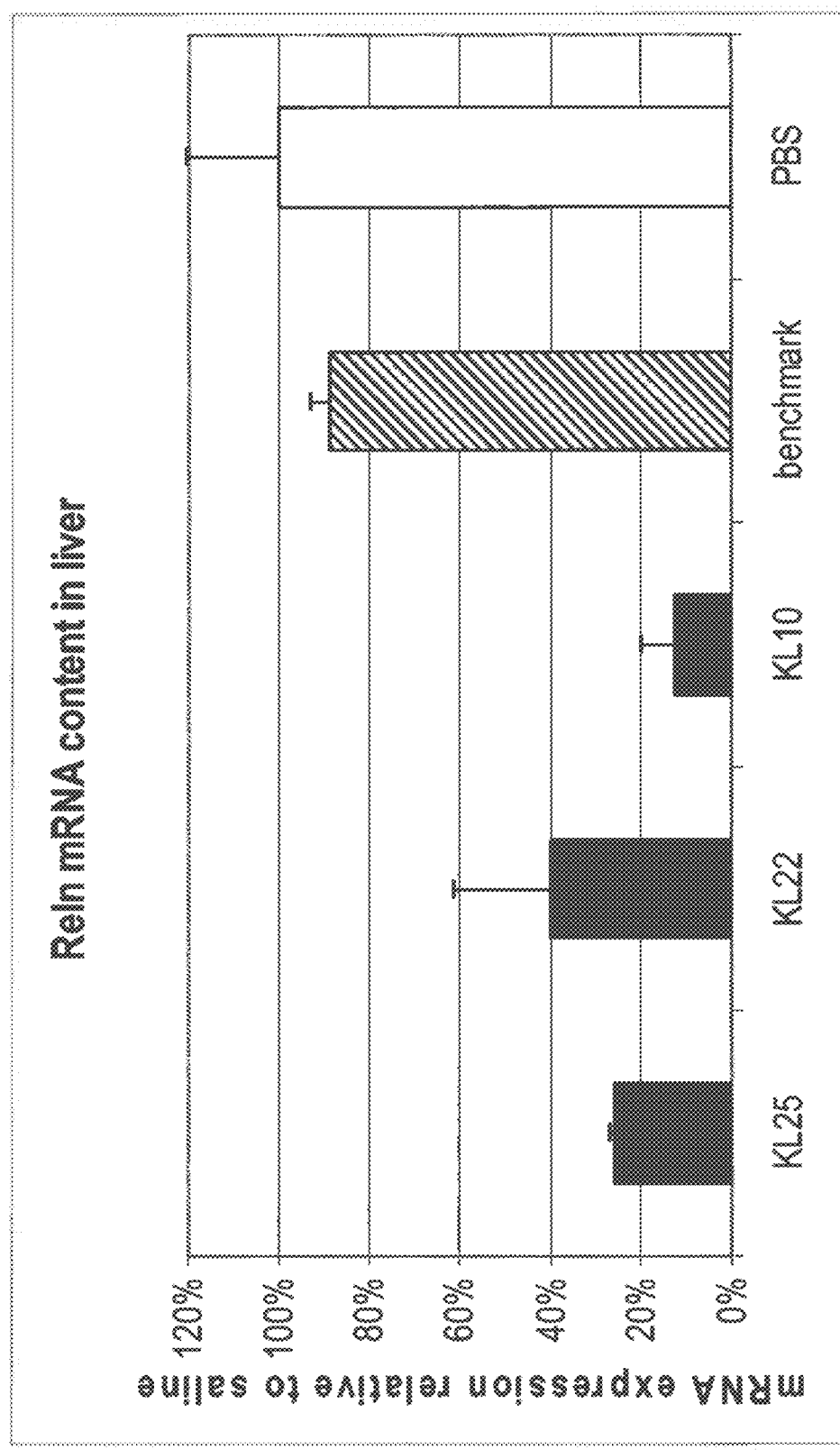
FIG. 7. Graph illustrating Rein mRNA levels after siRNA treatment employing different LNPs of the present invention. The LNPs contained a pool of five different siRNAs directed against five different targets (FVII, Rein, Clec4f, Tek, GFP). The siRNA dose was 0.5 mg/kg per siRNA (total siRNA dose 2.5 mg/kg). LNPs were dosed i.v. and 48 h post dosing mRNA levels were measured using bDNA assay. For comparison and shown has hashed bar, a benchmark LNP in which XTC2 substituted the amino-lipid was included.
Figure 8:
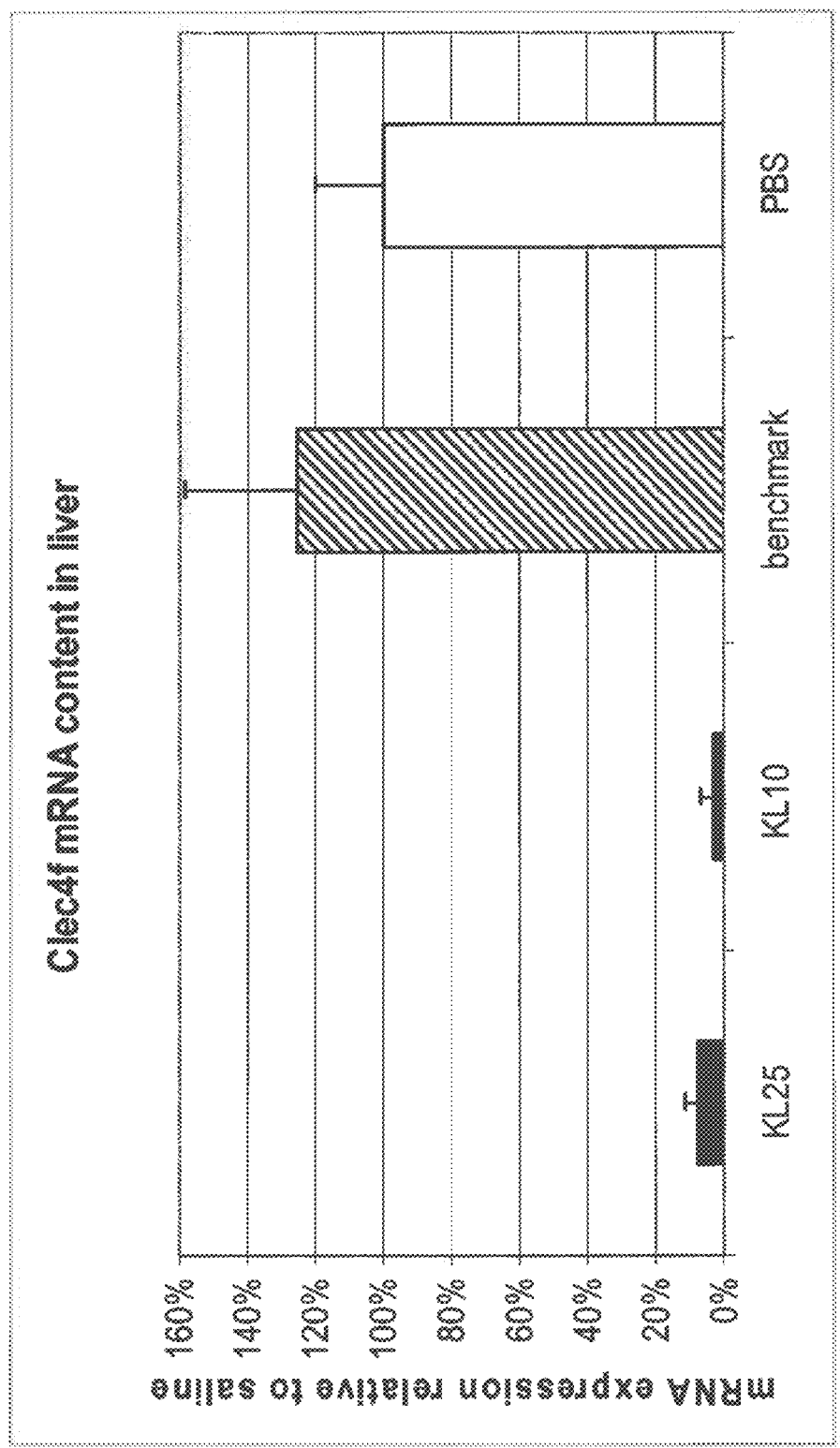
FIG. 8. Graph illustrating Clec4f mRNA levels after siRNA treatment employing different LNPs of the present invention. The LNPs contained a pool of five different siRNAs directed against five different targets (FVII, Rein, Clec4f, Tek, GFP). The siRNA dose was 0.5 mg/kg per siRNA (total siRNA dose 2.5 mg/kg). LNPs were dosed i.v. and 48 h post dosing mRNA levels were measured using bDNA assay. For comparison and shown has hashed bar, a benchmark LNP in which XTC2 substituted the amino-lipid was included.
Figure 9:
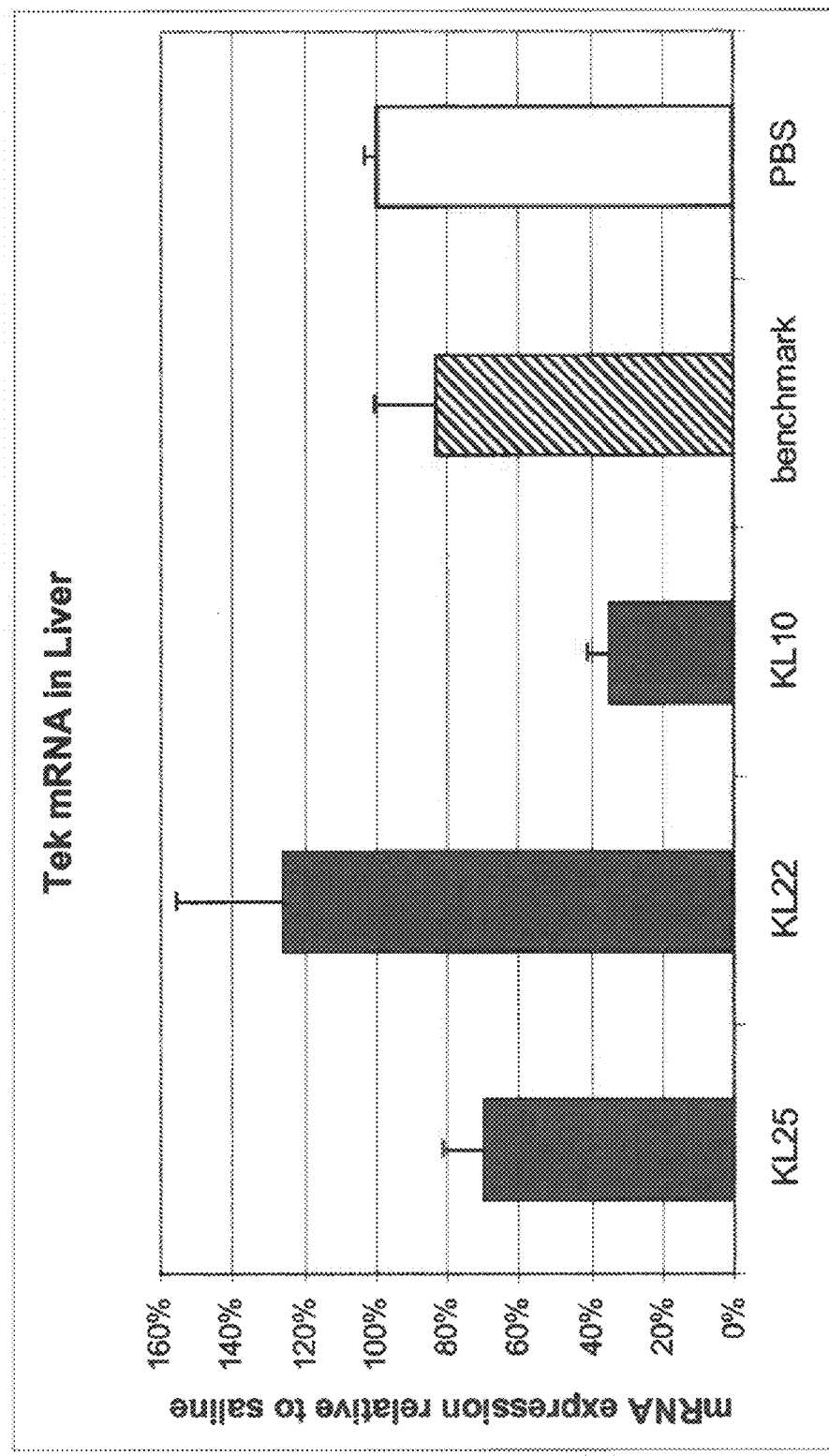
FIG. 9. Graph illustrating Tek mRNA levels in liver after siRNA treatment employing different LNPs of the present invention. The LNPs contained a pool of five different siRNAs directed against five different targets (FVII, Rein, Clec4f, Tek, GFP). The siRNA dose was 0.5 mg/kg per siRNA (total siRNA dose 2.5 mg/kg). LNPs were dosed i.v. and 48 h post dosing mRNA levels were measured using bDNA assay. For comparison and shown has hashed bar, a benchmark LNP in which XTC2 substituted the amino-lipid was included.
Figure 10:
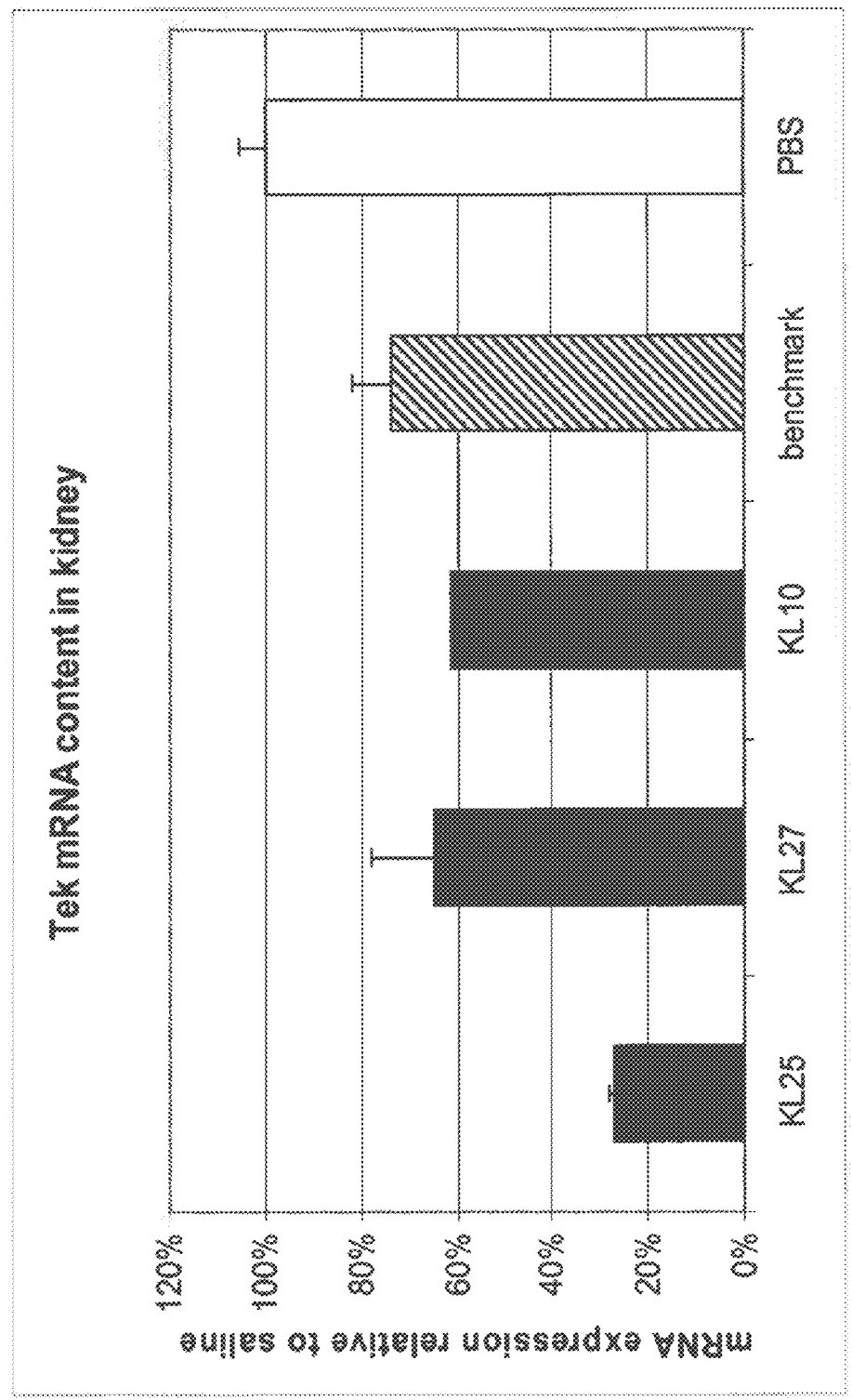
FIG. 10. Graph illustrating Tek mRNA levels in liver ater siRNA treatment employing different LNPs of the present invention. The LNPs contained a pool of five different siRNAs directed against five different targets (FVII, Rein, Clec4f, Tek, GFP). The siRNA dose was 0.5 mg/kg per siRNA (total siRNA dose 2.5 mg/kg). LNPs were dosed i.v. 5 and 48 h post dosing mRNA levels were measured using bDNA assay. For comparison and shown has hashed bar, a benchmark LNP in which XTC2 substituted the amino-lipid was included.
Figure 11:
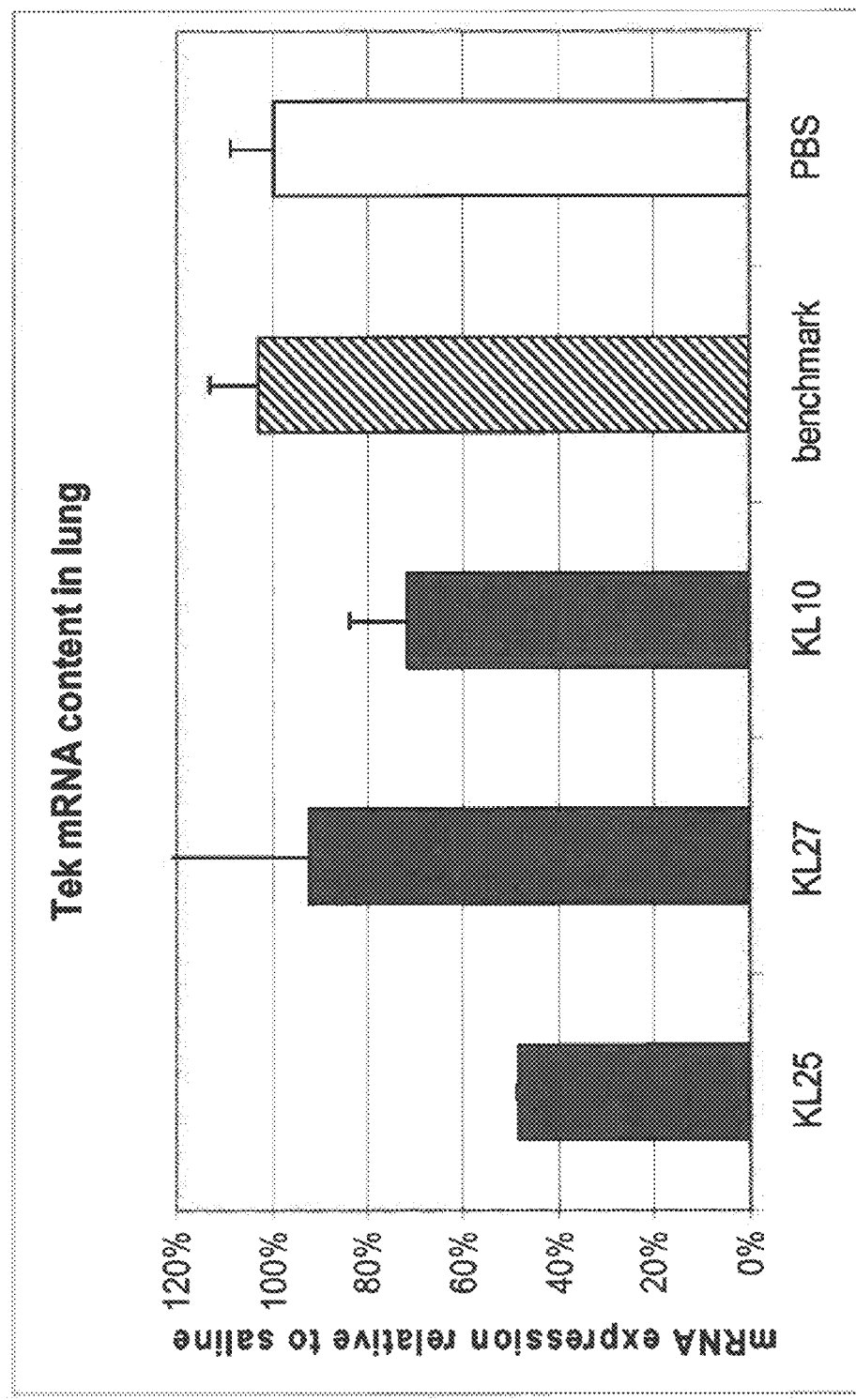
FIG. 11. Graph illustrating Tek mRNA levels in lung after siRNA treatment employing different LNPs of the present invention. The LNPs contained a pool of five different siRNAs directed against five different targets (FVII, Rein, Clec4f, Tek, GFP). The siRNA dose was 0.5 mg/kg per siRNA (total siRNA dose 2.5 mg/kg). LNPs were dosed i.v. and 48 h post dosing mRNA levels were measured using bDNA assay. For comparison and shown has hashed bar, a benchmark LNP in which XTC2 substituted the amino-lipid was included.
Figure 12:
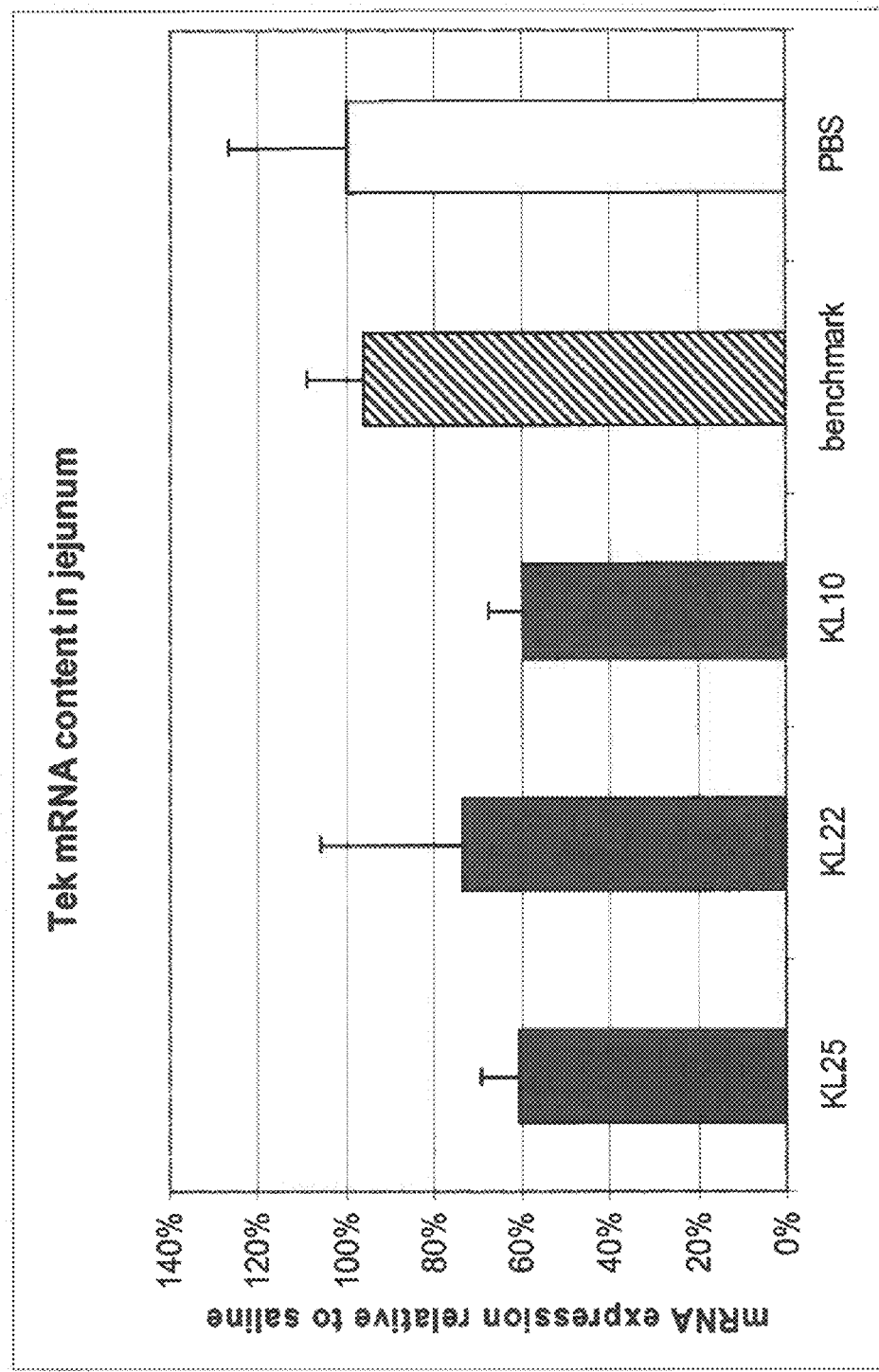
FIG. 12. Graph illustrating Tek mRNA levels in jejunum after siRNA treatment employing different LNPs of the present invention. The LNPs contained a pool of five different siRNAs directed against five different targets (FVII, Rein, Clec4f, Tek, GFP). The siRNA dose was 0.5 mg/kg per siRNA (total siRNA dose 2.5 mg/kg). LNPs were dosed i.v. and 48 h post dosing mRNA levels were measured using bDNA assay. For comparison and shown has hashed bar, a benchmark LNP in which XTC2 substituted the amino-lipid was included.
Figure 13:
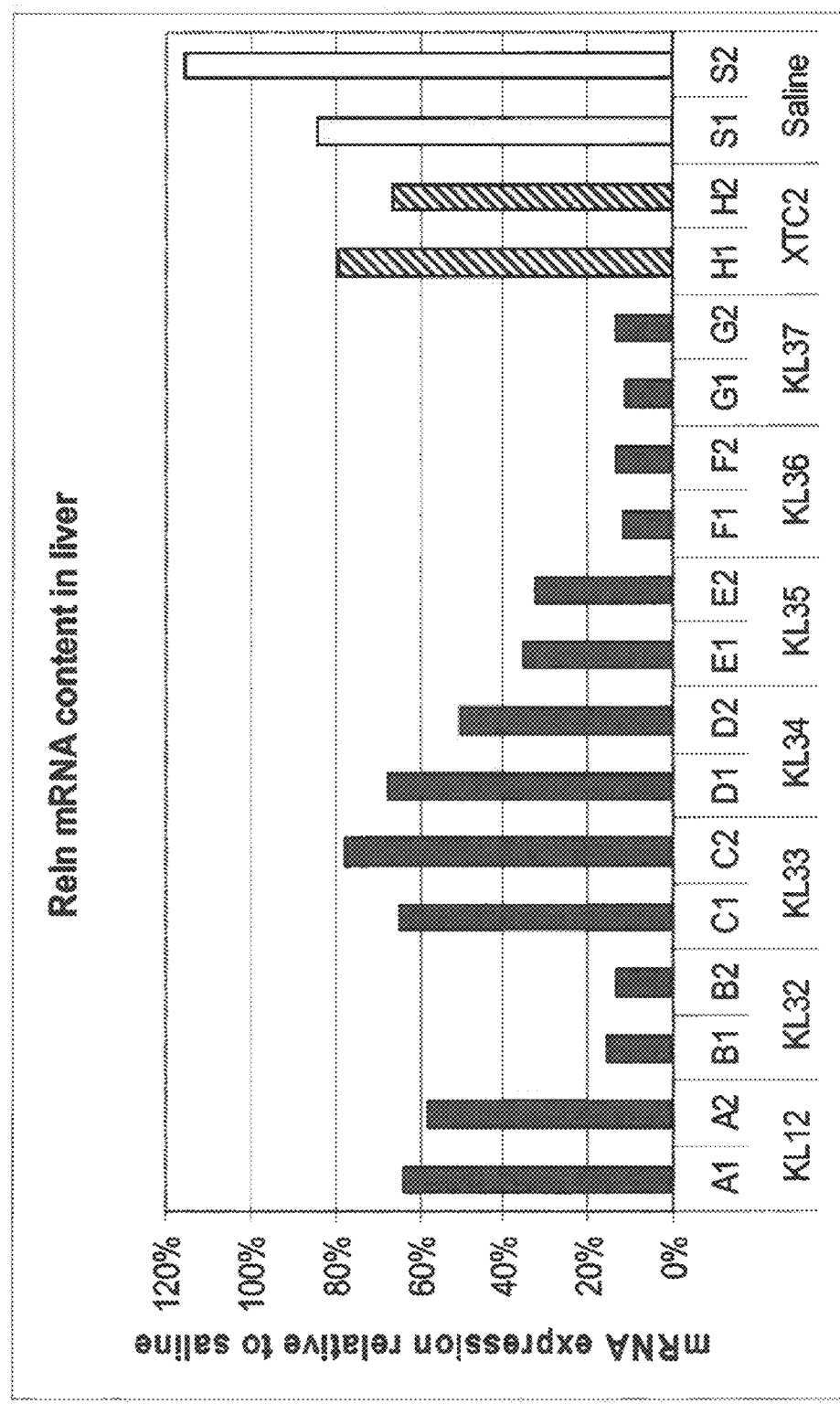
FIG. 13. Graph illustrating Rein mRNA expression levels of 2 individual animals per LNP relative to saline treated animals 48 h post iv dosing. LNPs contained a pool of five different siRNAs directed against FVII, GFP, Rein, Clec4f and Tek each at a dose of 0.5 mg/kg (total siRNA dose 2.5 mg/kg). LNPs were composed of 50 mol % amino-lipid designated by the KL numbers in the graphs below, 10 mol % DSPC, 38.5 mol % cholesterol and 1.5 mol % PEG-c-OMOG. For comparison and shown as hashed bar, a benchmark LNP in which XTC2 substituted the amino-lipid was included.
Figure 14:
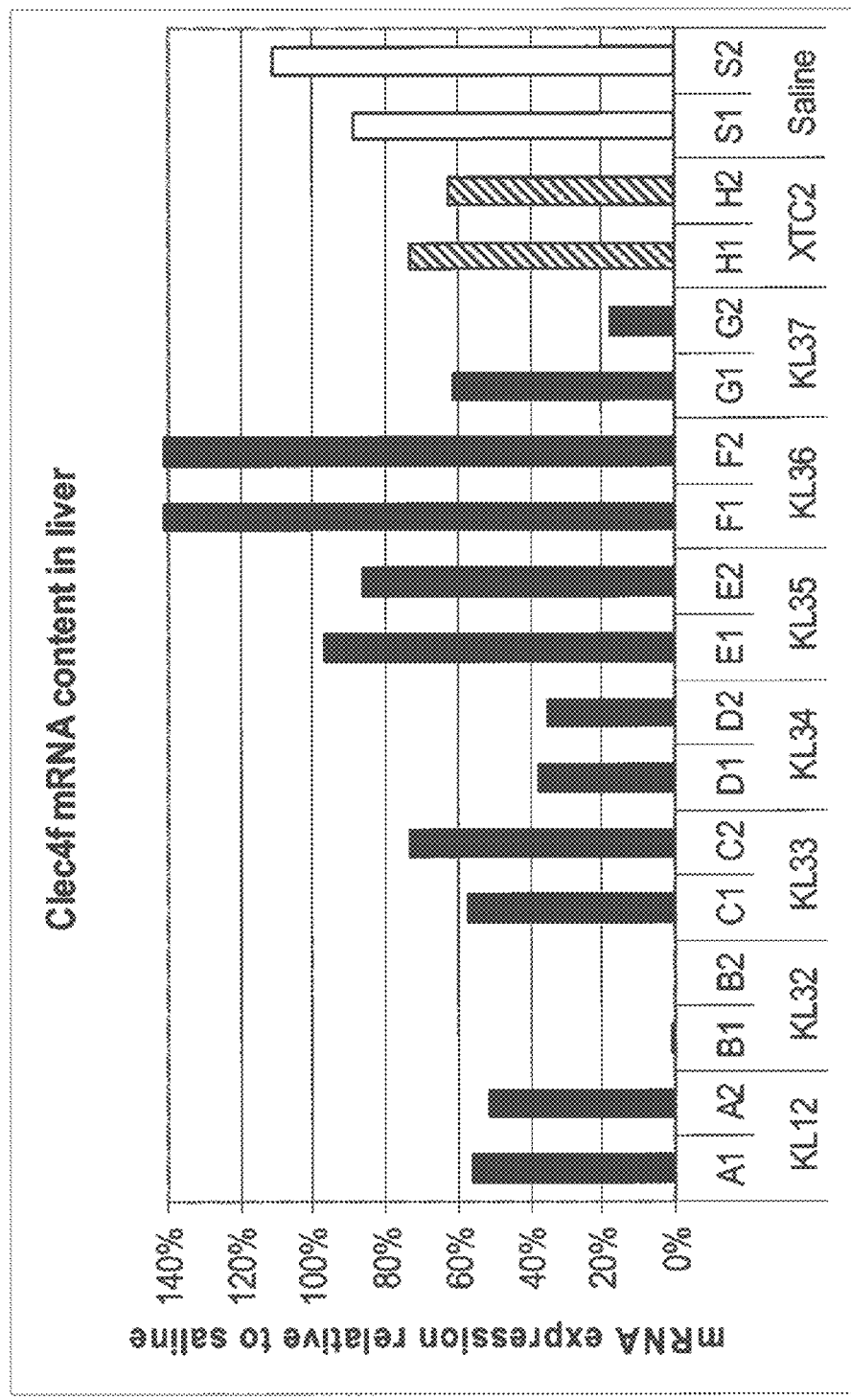
FIG. 14. Graph illustrating Clec4f mRNA expression levels of 2 individual animals per LNP relative to saline treated animals 48 h post iv dosing. LNPs contained a pool of five different sIRNAs directed against FVII, GFP, Rein, Clec4f and Tek each at a dose of 0.5 mg/kg (total siRNA dose 2.5 mg/kg). LNPs were composed of 50 mol % amino-lipid designated by the KL numbers in the graphs below, 10 mol % DSPC, 38.5 mol % cholesterol and 1.5 mol % PEG-c-OMOG. For comparison and shown as hashed bar, a benchmark LNP in which XTC2 substituted the amino-lipid was included.
Figure 15:
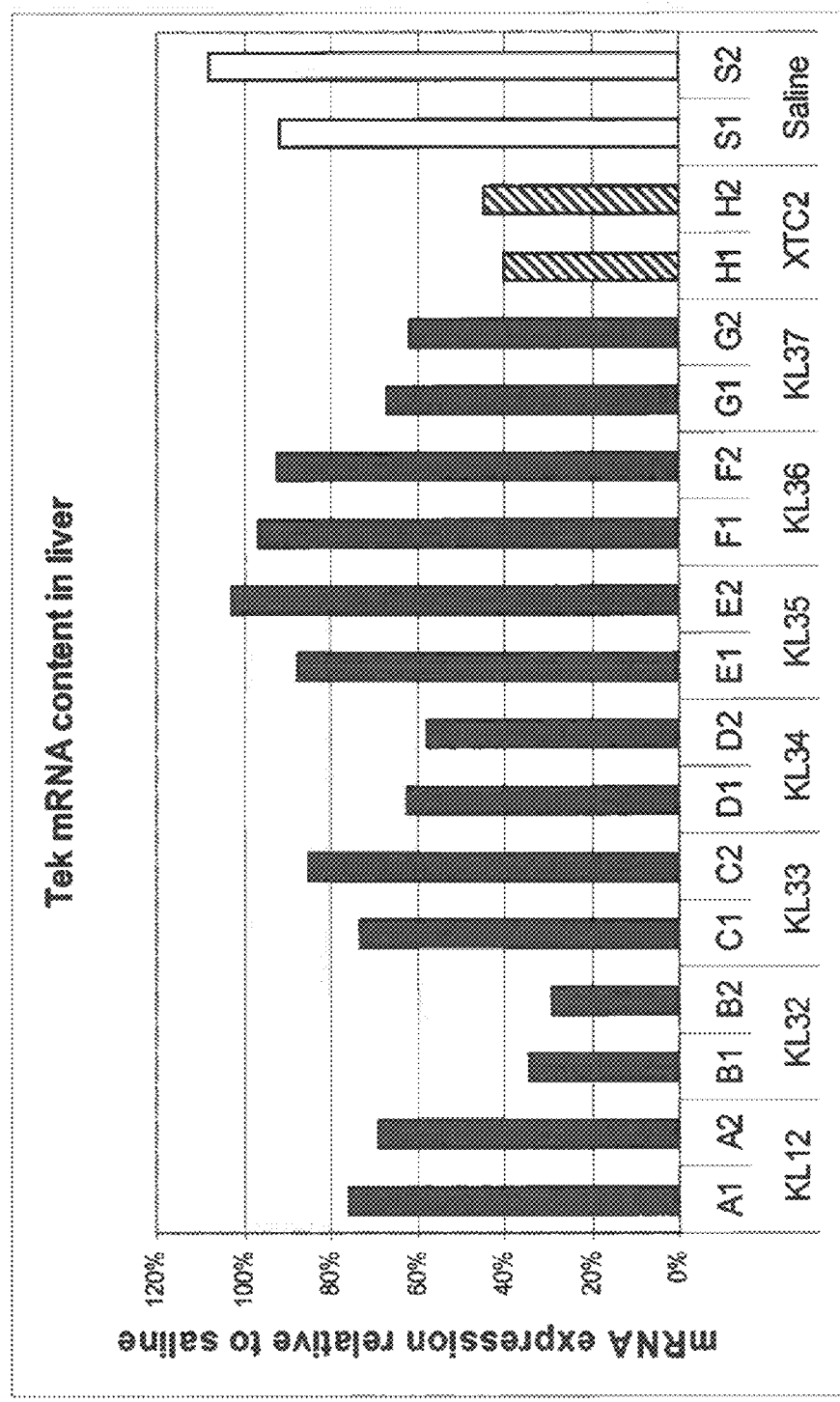
FIG. 15. Graph illustrating Tek mRNA expression levels of 2 individual animals per LNP relative to saline treated animals 48 h post iv dosing. LNPs contained a pool of five different siRNAs directed against FVII, GFP, Rein, Clec4f and Tek each at a dose of 0.5 mg/kg (total siRNA dose 2.5 mg/kg). LNPs were composed of 50 mol % amino-lipid designated by the KL numbers in the graphs below, 10 mol % DSPC, 38.5 mol % cholesterol and 1.5 mol % PEG-c-OMOG. For comparison and shown as hashed bar, a benchmark LNP in which XTC2 substituted the amino-lipid was included.
Figure 16:
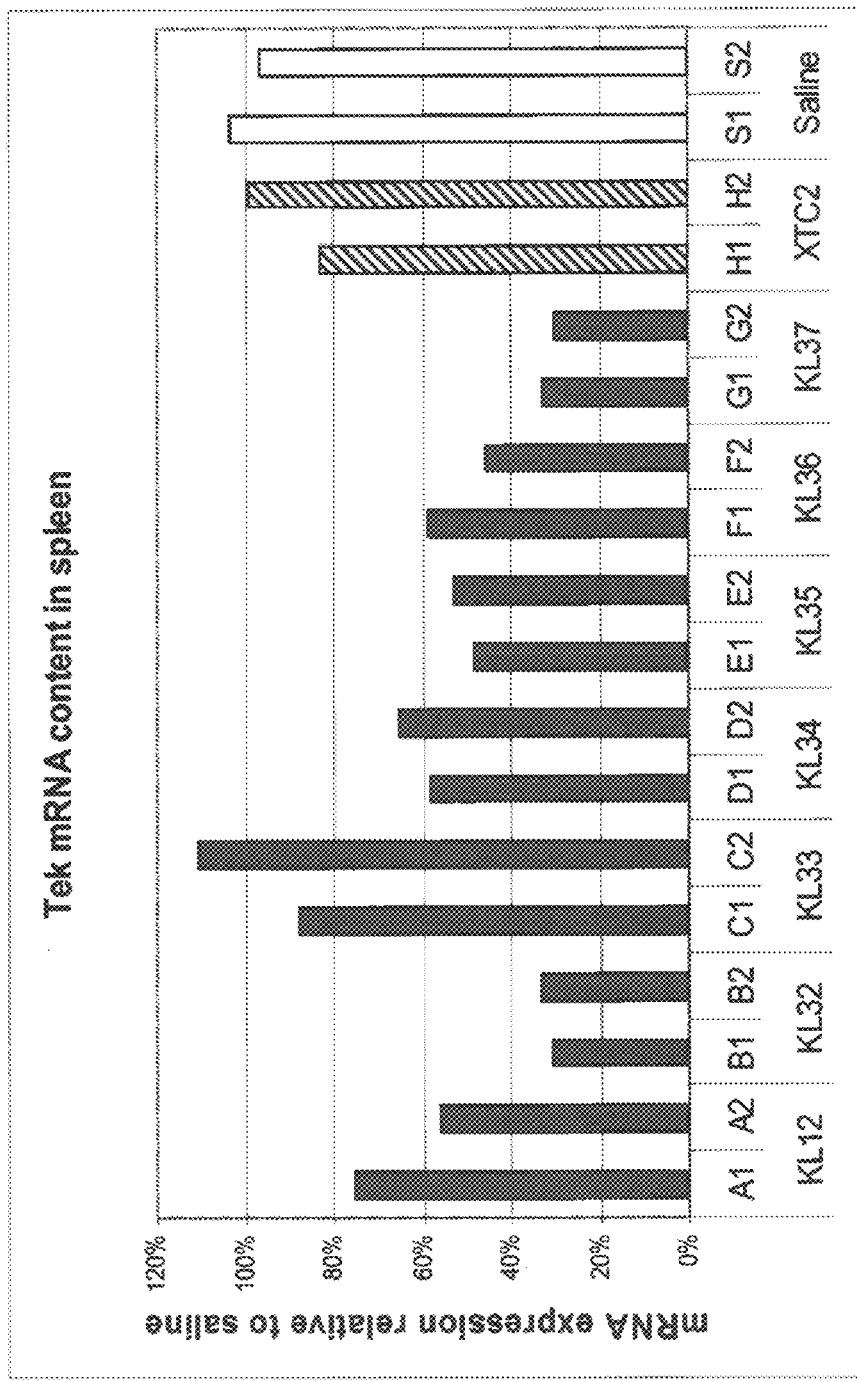
FIG. 16. Graph illustrating Tek mRNA expression levels of 2 individual animals per LNP relative to saline treated animals 48 h post iv dosing. LNPs contained a pool of five different siRNAs directed against FVII, GFP, Rein, Clec4f and Tek each at a dose of 0.5 mg/kg (total siRNA dose 2.5 mg/kg). LNPs were composed of 50 mol % amino-lipid designated by the KL numbers in the graphs below, 10 mol % DSPC, 38.5 mol % cholesterol and 1.5 mol % PEG-c-OMOG. For comparison and shown as hashed bar, a benchmark LNP in which XTC2 substituted the amino-lipid was included.
Figure 17:
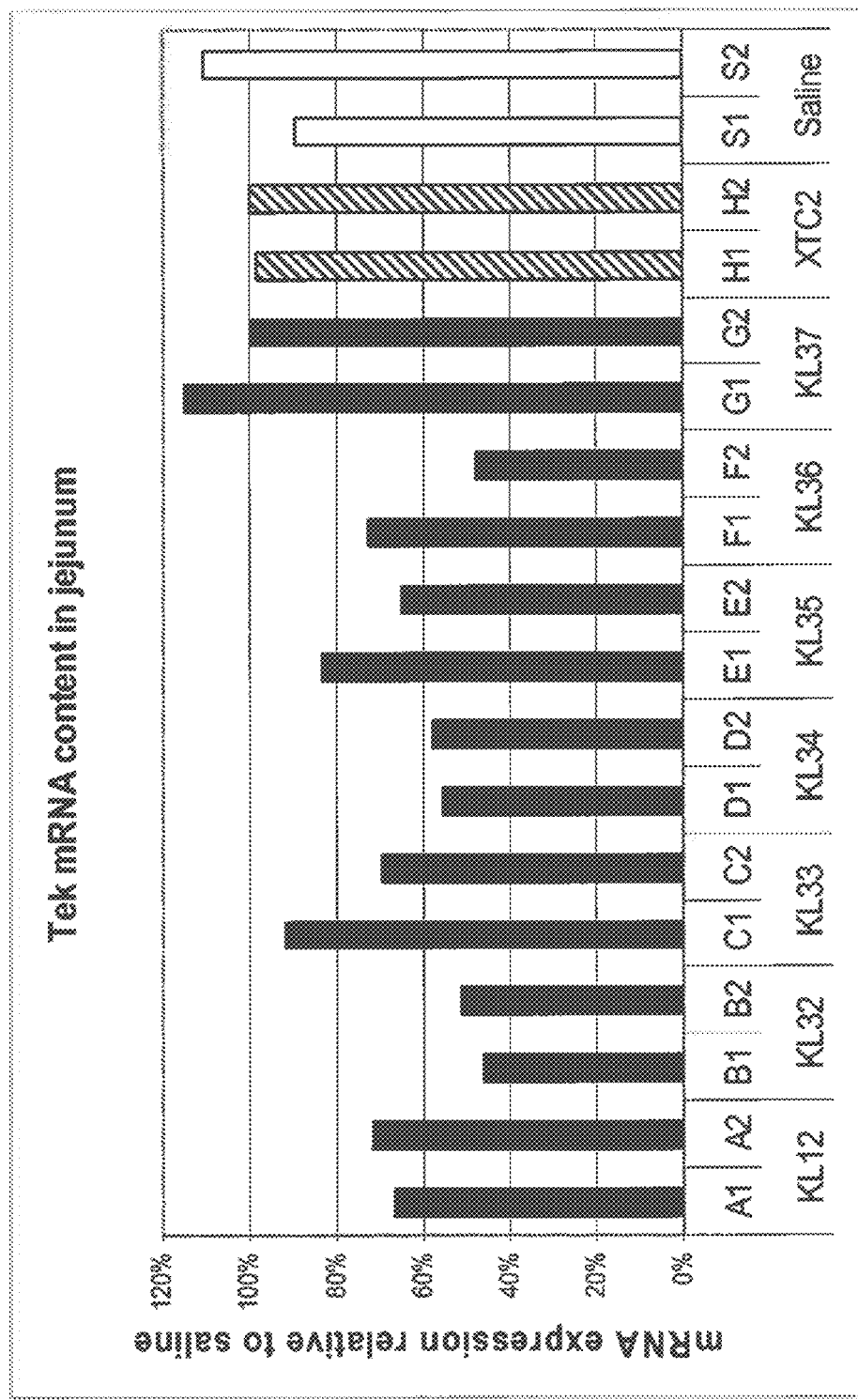
FIG. 17. Graph illustrating Tek mRNA expression levels of 2 individual animals per LNP relative to saline treated animals 48 h post iv dosing. LNPs contained a pool of five different siRNAs directed against FVII, GFP, Rein, Clec4f and Tek each at a dose of 0.5 mg/kg (total siRNA dose 2.5 mg/kg). LNPs were composed of 50 mol % amino-lipid designated by the KL numbers in the graphs below, 10 mol % DSPC, 38.5 mol % cholesterol and 1.5 mol % PEG-c-OMOG. For comparison and shown as hashed bar, a benchmark LNP in which XTC2 substituted the amino-lipid was included.

A. Amino-Lipids and Methods of Producing them

The amino-lipids provided herein are produced by reductive amination of a (poly)amine and an aliphatic carbonyl compound according to the general reaction scheme:

$$R'-NH_2 + R-CHO \rightarrow R'-N(CHR)_2$$

$$R'-NH_2 + R-CO-R \rightarrow R'-N(CR_2)_2$$

The amino-lipids may be prepared by reacting the aliphatic carbonyl compound and the (poly)amine in the presence of a reducing agent.

In certain embodiments the aliphatic carbonyl compound is a ketone. In certain embodiments the aliphatic carbonyl compound is an aldehyde. Typically, the (poly)amine has two to five nitrogen atoms in its structure. In certain embodiments the (poly)amine contains primary and/or secondary and/or tertiary nitrogen atoms. Depending on the structure of the (poly)amine, and the aliphatic carbonyl compound employed regioselective alkylations can be achieved. Particularly, when ketones are reacted with polyamines displaying primary and/or secondary and/or tertiary nitrogens under reductive amination conditions selective alkylations of primary nitrogens van be achieved. The present invention covers procedures of making amino-lipids or the following structures:

$RNH(CH_2)_xNH_2$, $R_2N(CH_2)_xNH_2$, $R_2N(CH_2)_xNHR$, $R_3N(CH_2)_xNR_2$, $RNH[(CH_2)_x(C_wH_{2w}NH)y(CH_2)_z]NH_2$, $RNH[(CH_2)_x(C_wH_{2w}NR)y(CH_2)_z]NH_2$, $RNH[(CH_2)_x(C_wH_{2w}NR)_y(C_vH_{2v}NH)_u(CH_2)_z]NH_2$, $R_2N[(CH_2)_x(C_wH_{2w}NH)_y(CH_2)_z]NH_2$, $R_2N[(CH_2)_x(C_wH_{2w}NR)_y(CH_2)_x]NH_2$, $R_2N[(CH_2)_x(C_wH_{2w}NR)_y(C_vH_{2v}NH)_x(CH_2)_z]NH_2$, $RNH[(CH_2)_x(C_wH_{2w}NH)_y(CH_2)_z]NHR$, $RNH[(CH_2)_x(C_wH_{2w}NR)_y(CH_2)_z]NHR$, $RNH[(CH_2)_x(C_wH_{2w}NR)_y(C_vH_{2v}NH)_u(CH_2)_z]NHR$, $R_2N[(CH_2)_x(C_wH_{2w}NH)_y(CH_2)_z]NHR$, $R_2N[(CH_2)_x(C_wH_{2w}NR)_y(CH_2)_z]NHR$, $R_2N[(CH_2)_x(C_wH_{2w}NR)_y(C_vH_{2v}NH)_u(CH_2)_z]NHR$, $R_2N[(CH_2)_x(C_wH_{2w}NH)_y(CH_2)_z]NR_2$, $R_2N[(CH_2)_x(C_wH_{2w}NR)_y(CH_2)_z]NR_2$, $R_2N[(CH_2)_x(C_wH_{2w}NR)_y(C_vH_{2v}NH)_u(CH_2)_z]NR_2$, $N\{[(CH_2)_x(C_wH_{2w}NH)_y(CH_2)_z]NHR\}_3$, $N\{[(CH_2)_x(C_wH_{2w}NH)_y(CH_2)_z]NR\}_3$, $HN\{[(CH_2)_x(C_wH_{2w}NH)_y(CH_2)_z]NHR\}_2$, and $HN\{[(CH_2)_x(C_wH_{2w}NH)_y(CH_2)_z]NR_2\}_2$, wherein R is selected from alkyl, alkenyl or alkynyl carbon chains ranging from C6 to C20. In certain embodiments these chains comprise at least one, at least two or at least three sites of unsaturation, for example one or more double bonds or triple bonds. In one embodiment, R comprises at least one aromatic cycle, including for example a heterocycle. In yet another embodiment, R may comprise at least one heteroatom in the carbon chain, for example O, NH, NR', S, SS, wherein R' is an acyl, alkyl, alkenyl or alkynyl group consisting of two to 20 carbon atoms. In still another embodiment, at least one hydrogen in the hydrocarbon chain R may be replaced by F, Cl, Br, I. In one embodiment, w and v are independently 2, 3 or 4. In one embodiment, y and u are independently 0, 1, 2, 3 or 4. In one embodiment, x and z are independently 2, 3 or 4.

In one aspect, the present invention provides cyclic amino-lipids of the formula (I):

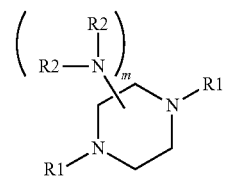

wherein
$R^1$ is independently selected from
—(CH$_2$)$_2$—N(R)$_2$,
—(CH$_2$)$_2$—N(R)—(CH$_2$)$_2$—N(R)$_2$, wherein R is independently selected from —H, C6-40 alkyl, C6-40 alkenyl and C6-40 alkynyl, provided that —N(R)$_2$ is not NH$_2$, and
C6-40 alkyl, and C6-40 alkenyl;
$R^2$ is C6-40 alkyl, C6-40 alkenyl, or C6-40 alkynyl;
m is 0 or 1; and
pharmaceutically acceptable salts thereof.

The term "C6-40 alkyl" as used herein means a linear or branched, saturated hydrocarbon consisting of 6 to 40 carbon atoms, preferably of 6 to 30 carbon atoms, most preferably of 6 to 20 carbon atoms. Especially preferred are alkyl groups containing 10, 14 or 15 carbon atoms.

The term "C6-40 alkenyl" as used herein means a linear or branched, unsaturated hydrocarbon consisting of 6 to 40 carbon atoms, preferably of 6 to 30 carbon atoms, most preferably of 6 to 15 carbon atoms. In one embodiment the C6-40 alkenyl groups comprise 1 to 4 double bonds, preferably between 1 to 3 double bonds, most preferably 1 or 2 double bonds.

The term "C6-40 alkynyl" as used herein means a linear or branched, unsaturated hydrocarbon consisting of 6 to 40 carbon atoms, preferably of 6 to 30 carbon atoms, most preferably of 6 to 20 carbon atoms. In one embodiment the C6-40 alkynyl groups comprise 1 to 4 triple bonds, preferably 1 to 3 triple bonds, most preferably 1 or 2 triple bonds.

In another embodiment there are provided the cyclic amino-lipids selected from

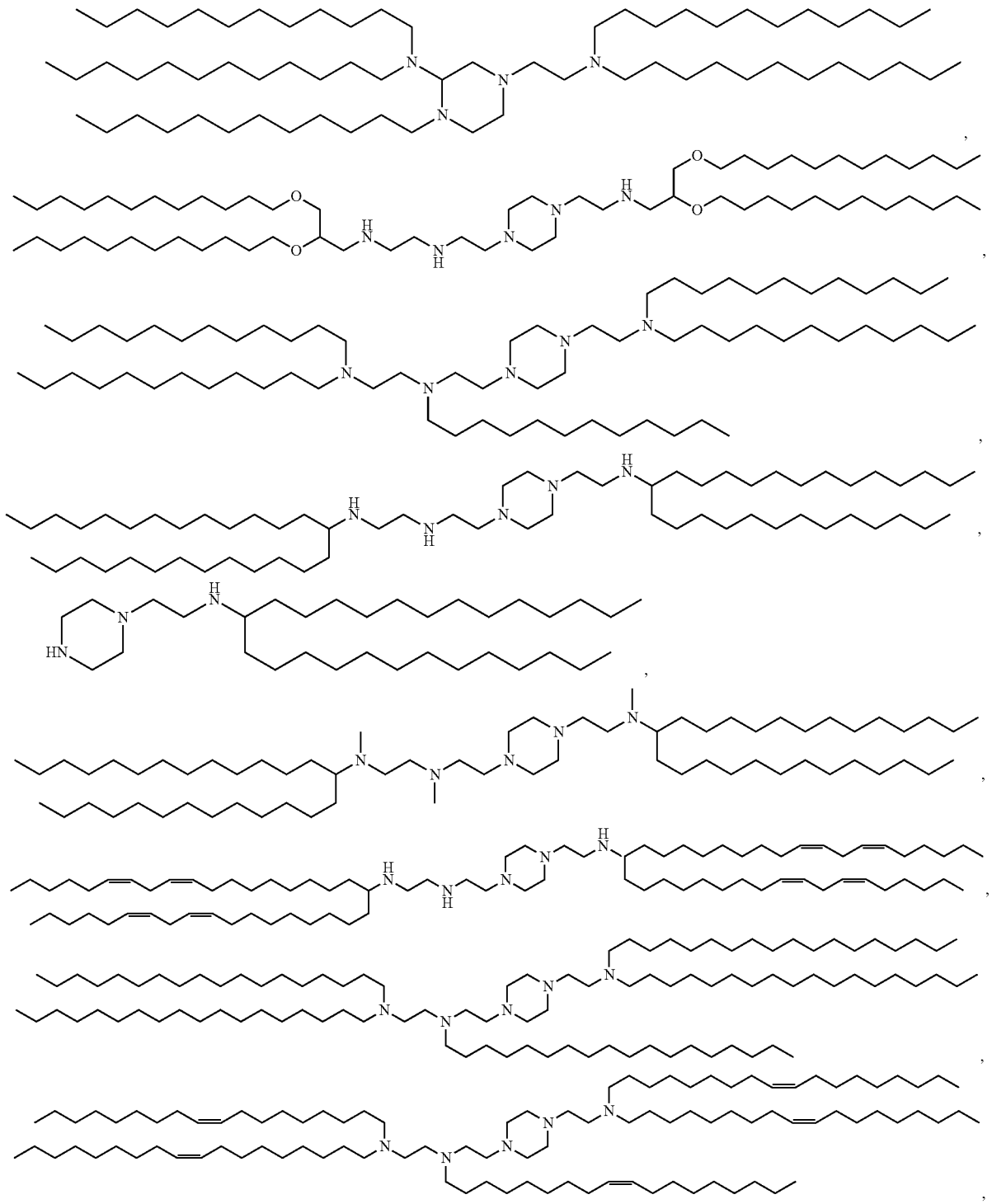

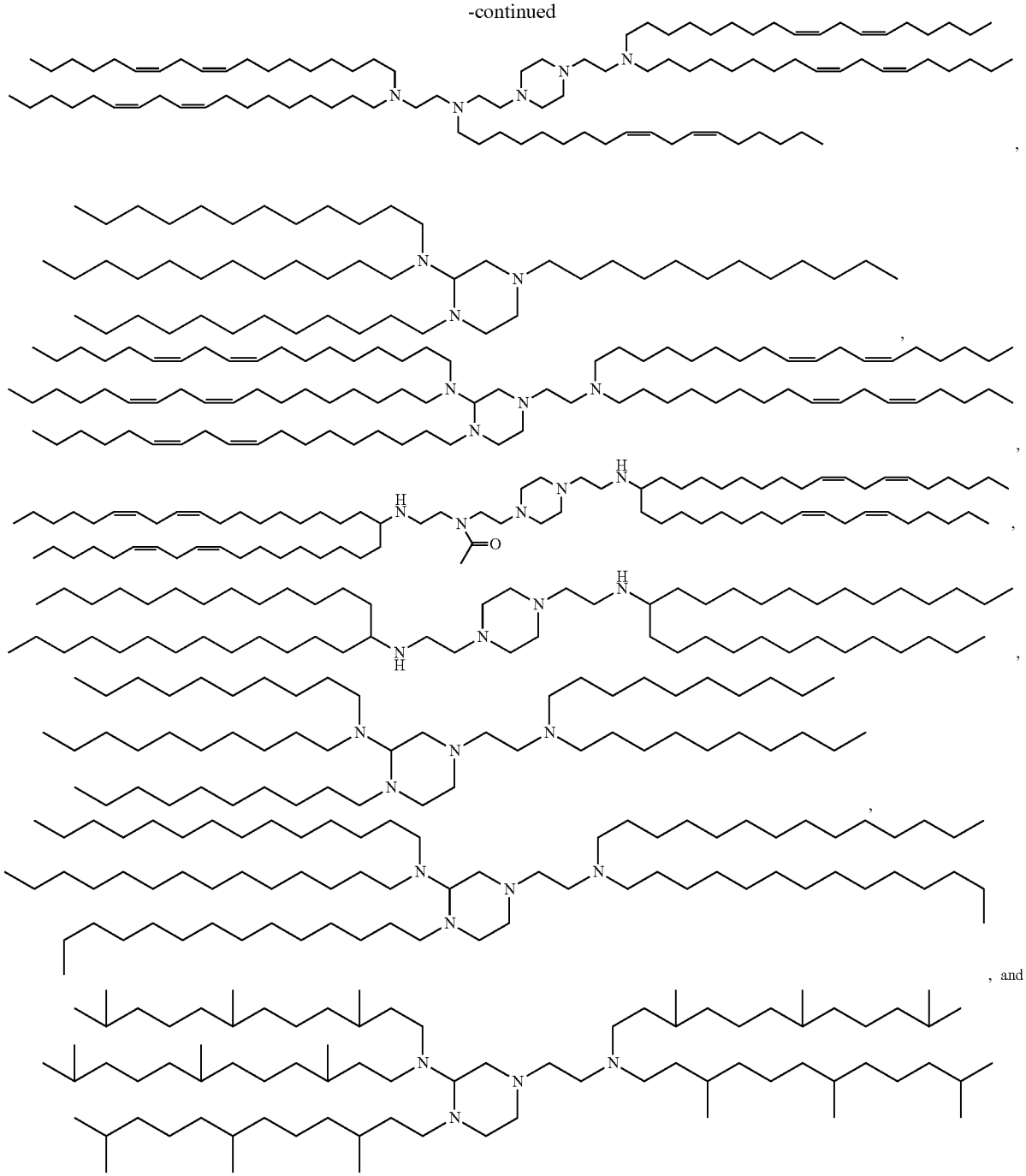
Preferred therein are the cyclic amino-lipids selected from
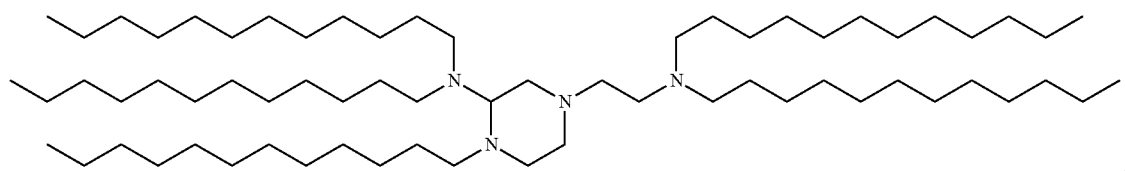

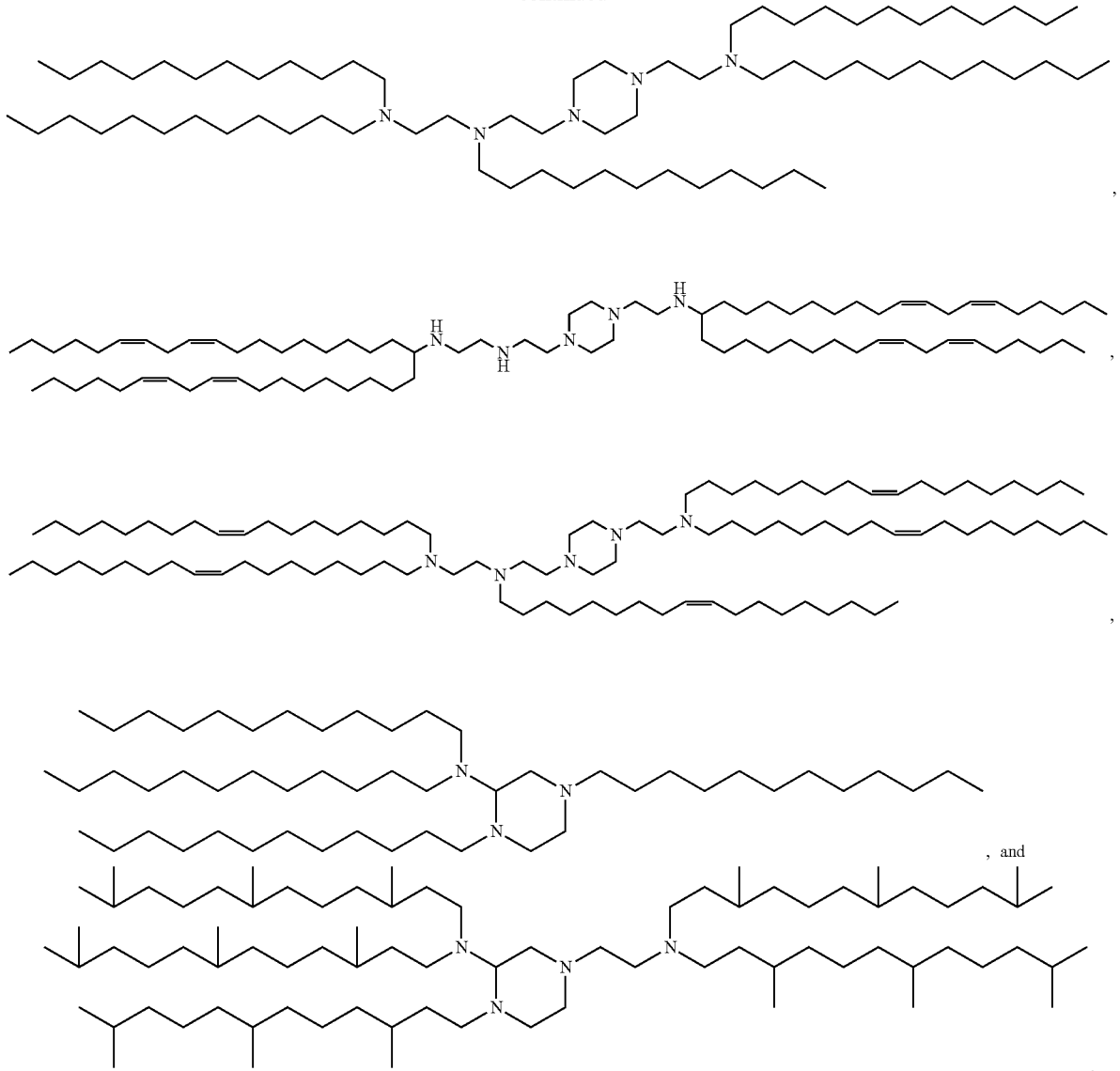

In one aspect, the present invention provides linear amino-lipids of the formula (II):

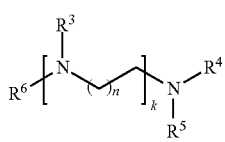

wherein
R$^3$ bis independently selected from C1-40 alkyl or C6-40 alkenyl, wherein up to 4 carbon atoms may be replaced by a heteroatom selected from oxygen or nitrogen;
R$^4$ is selected from C12-40 alkyl or C6-40 alkenyl, wherein up to 4 carbon atoms may be replaced by a heteroatom selected from oxygen or nitrogen;
R$^5$ is selected from hydrogen, C12-30 alkyl and C6-40 alkenyl;
R$^6$ is selected from hydrogen and C1-12 alkyl;
n is 1, 2, or 3; and
k is 1, 2, 3 or 4.

In a preferred embodiment, a linear amino-lipids of the formula (II) is provided wherein
R$^3$ is independently selected from C1-, C12-, C14-, C27-, C30- and C37-alkyl, wherein 1 or 2 carbon atoms can be optionally replaced by an oxygen or a nitrogen atom;
R$^4$ is selected from C12-, C14-, C27-, C30- and C37-alkyl, wherein 1 or 2 carbon atoms can be optionally replaced by an oxygen or a nitrogen atom;
R$^5$ is selected from hydrogen, C12-, C14- and C30-alkyl, in which one carbon atom can be optionally replaced by a nitrogen atom;
R$^6$ is selected from hydrogen, C1- and C12-alkyl; and
n and k have the meanings given in claim 1.

In one embodiment there are provided the linear amino-lipids selected from

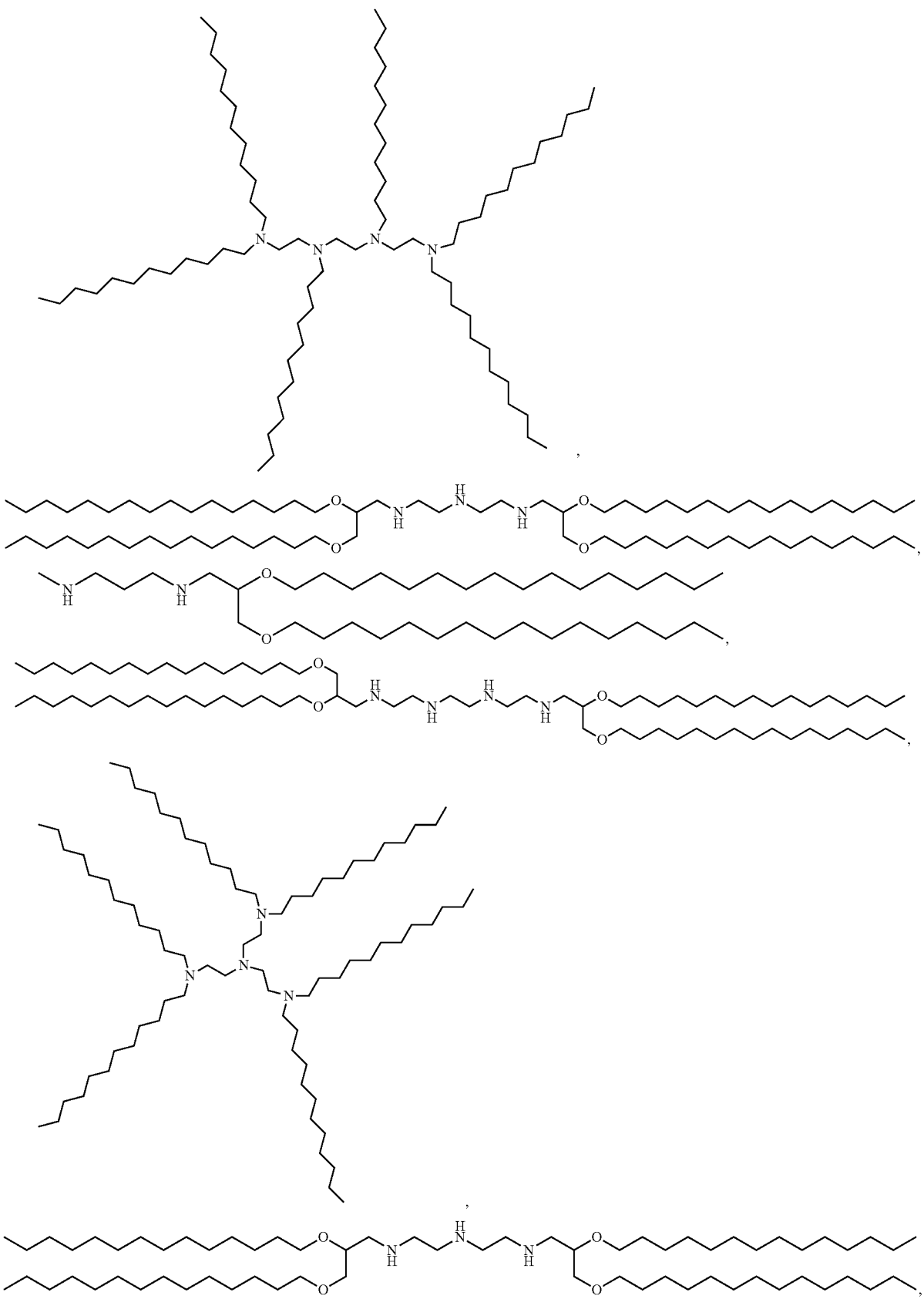

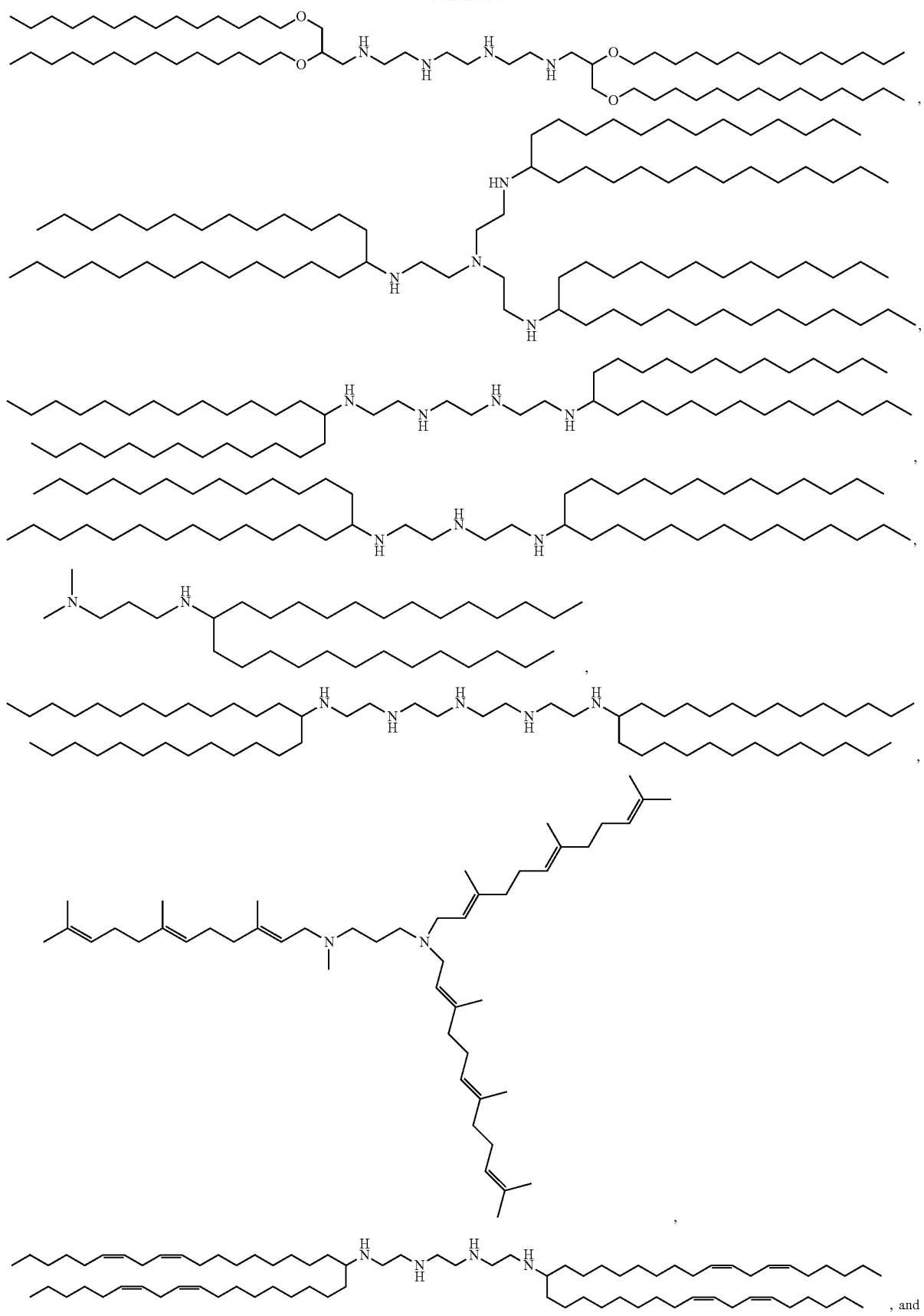

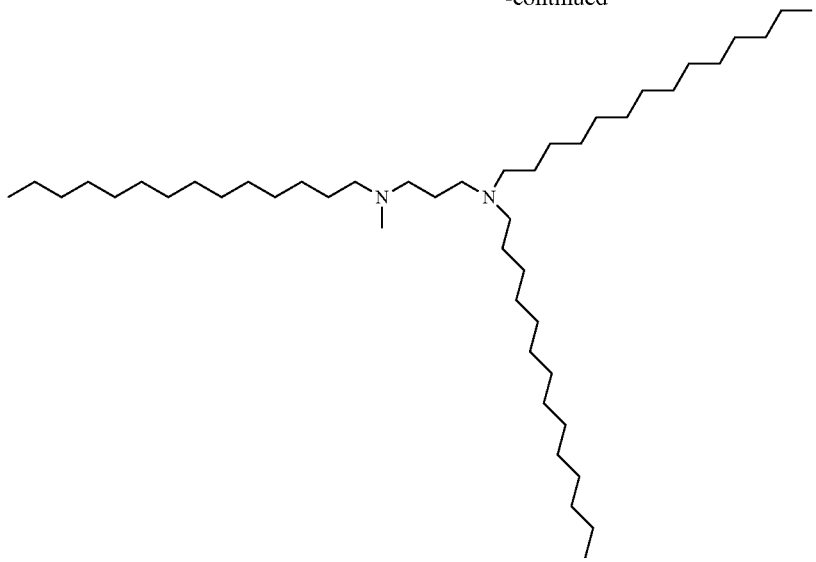
Preferred therein is the linear amino-lipid
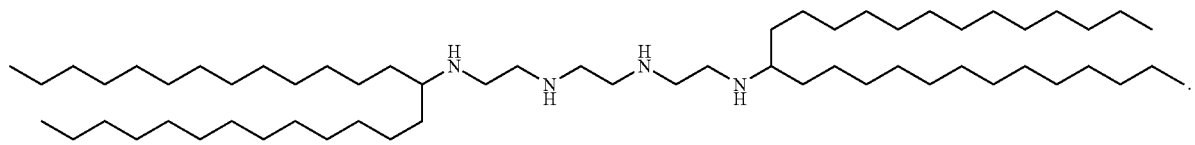 [SMILES: CCCCCCCCCCCCCC(CCCCCCCCCCCCC)NCCNCCNCCNC(CCCCCCCCCCCCC)CCCCCCCCCCCCC]
In yet another embodiment an amino-lipid of formula
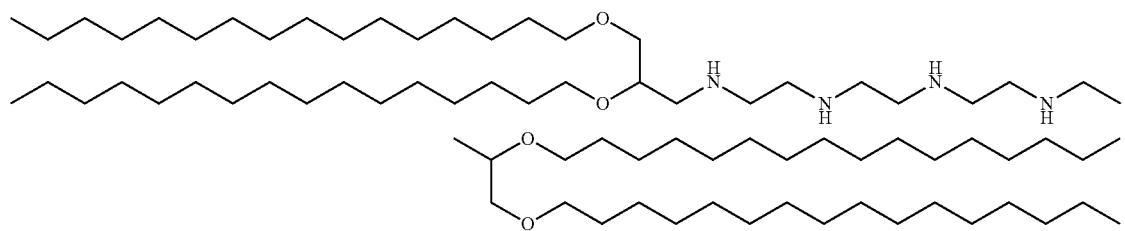
is provided.
In yet another embodiment an amino-lipid of formula
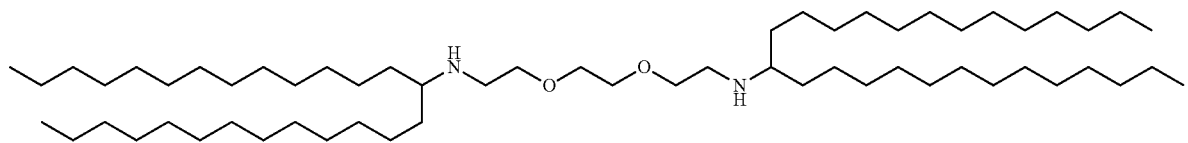 [SMILES: CCCCCCCCCCCCCC(CCCCCCCCCCCCC)NCCOCCOCCNC(CCCCCCCCCCCCC)CCCCCCCCCCCCC]
is provided.
In yet another embodiment an amino-lipid of formula
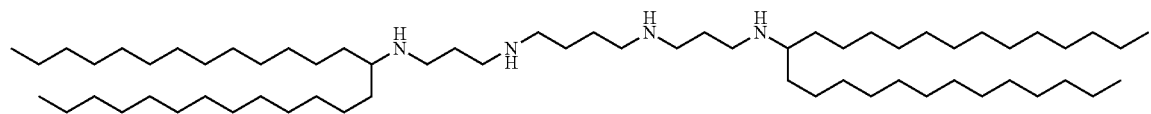 [SMILES: CCCCCCCCCCCCCC(CCCCCCCCCCCCC)NCCCNCCCCNCCCNC(CCCCCCCCCCCCC)CCCCCCCCCCCCC]

is provided.

In particular embodiments the amino-lipids of the present invention comprise Nitrogen atoms that are protonated depending on the pH of the environment, preferably at least one Nitrogen atom is positively charged at physiological pH or below. The extent of pH dependent protonation is effected by an equilibrium reaction and hence not the entire, but only the predominant lipid species is positively charged. At physiological pH at least one of the nitrogen atoms in the lipid structure is protonated.

As used herein, the term "(poly)amine" refers to a saturated hydrocarbon linear or branched wherein 2 to 5 Carbon atoms are replaced by Nitrogen. Preferably said (poly)amine comprises two to five nitrogen atoms. Preferred therein are (poly)amines that comprise amine Nitrogens that are separated by 2 and/or 3 and/or 4 carbon atoms. Non-limiting examples of suitable (poly)amines are ethylenediamine, diethylenetriamine, triethylenetetramine, tetraethylenepentamine, tris-(2-aminoethyl)-amine, 3-dimethylamino-1-propylamine, spermine, spermidine, 2,2'-(ethylenedioxy)-bis (ethylamine). The term "aliphatic carbonyl compound" as used herein refers to a compound R—CO—R', wherein R is a ketone or an aldehyde comprising of alkyl and/or alkenyl and/or alkynyl groups and R' is H or a ketone or an aldehyde comprising of alkyl and/or alkenyl and/or alkynyl groups.

The term "reducing agent" as Used herein refers to a reagent that enables the reduction of the iminium ion intermediate in reductive amination reactions. Examples of such reagents include, but are not limited to hydride reducing reagents such as sodium cyanoborohydride, sodium triacetoxyborohydride and sodium borotetrahydride. Catalytic hydrogenation with metal catalyst such as nickel, palladium or platinum can also be used for this purpose. As used herein, the term "lipid" refers to amphiphilic molecules comprising a polar, water soluble "headgroup" and a hydrophobic "tail". The headgroup preferably consists of a pH dependent charged group such as an amine. The tail preferably comprises aliphatic residues. Lipids can be of natural origin or of synthetic origin. Examples include, but are not limited to, fatty acids (e.g. oleic acid, lineolic acid, stearic acid), glycerolipids (e.g. mono-, di-, triglycrols such as triglycerides), phospholipids (e.g. phosphatidylethanolamine, phosphatidylcholine), and sphingolipids (e.g. sphingomyelin)

As used herein, the term "amino-lipid" refers to lipids having at least one of the Nitrogen atoms incorporated in at last one fatty acid chain. This fatty acid chain may be an alkyl, alkenyl or alkynyl carbon chain. Lipids containing carbon chain lengths in the range from C10 to C20 are preferred. It is understood that the fatty acid portion of the amino-lipid of the present invention is incorporated through the use of suitable carbonyl compounds such as aldehydes (R—CHO) and ketones (R—CO—R). Through the use of asymmetrical ketones (R—CO—R') corresponding unsymmetrical substituted lipids can be prepared. Likewise, through the use of carbonyl ethers, esters, carbamates and amides and suitable reducing agents the corresponding amino-lipids are accessible.

The term "cyclic amino-lipid" as used herein refers to an amino-lipid of the general formula (I).

The term "linear amino-lipid" as used herein refers to an amino-lipid of the general formula (II).

In another aspect, novel amino-lipids can be prepared by reacting a suitable (poly)amine with a carbonyl compound in the presence of a reducing agent to form a cyclic or linear amino-lipid.

In certain embodiments the alkyl, alkenyl and alkynyl groups as covered in the present invention contain 2 to 20 carbon atoms. In certain other embodiments these groups consists of 2 to 10 carbon atoms. In yet other embodiments the alkyl, alkenyl and alkynyl groups employed in this invention contain 2 to 8 carbon atoms. In still other embodiments these groups contain two to six carbon atoms. In yet other embodiments the alkyl, alkenyl and alkynyl groups of the invention contain 2 to four carbon atoms.

The term "alkyl" as used herein means a chain of saturated hydrocarbons that is aliphatic, branched or cycloaliphatic. Saturated aliphatic hydrocarbons include methyl, ethyl, n-propyl, n-butyl and the like. Saturated branched alkyls include isopropyl, isobutyl, tert-butyl and the like. Representative cyclo-aliphatic alkyls include cyclopropyl, cyclobutyl, cyclopentyl, cyclohexyl and the like.

The term "alkenyl" denotes a chain of hydrocarbons that has at least one carbon-carbon double bond. For example alkenyl groups include ethenyl, propenyl, butenyl, isopropylidene and the like. The term also covers cyclic alkenyls such as cyclopropenyl, cyclobutenyl, cyclopentenyl and the like.

The term "alkynyl" denotes a chain of hydrocarbons that has at least one carbon-carbon triple bond. Exemplary alkynyl groups include ethynyl, propynyl, butynyl and the like. The ten also covers cyclic alkynyls such as cyclopentynyl, cyclohexynyl, and the like.

The term "acyl" refers to any alkyl, alkenyl or alkynyl group that is linked through a carbonyl group. For example, acyl groups are —(CO)-alkyl, —(CO)-alkenyl and —(CO)-alkynyl.

B. Lipid Nanoparticles (LNPs) Comprising the Inventive Amino-Lipids

Also provided herein are compositions comprising the amino-lipids of the invention that form lipid nanoparticles (LNPs). As used herein, the term "lipid nanoparticles" includes liposomes irrespective of their lamellarity, shape or structure and lipoplexes as described for the introduction of pDNA into cells (PNAS, 1987, 84, 7413). These lipid nanoparticles can be complexed with biologically active compounds such as nucleic acids and are useful as in vivo delivery vehicles. Preferably said in vivo delivery is cell-type specific.

In one embodiment, said lipid nanoparticles comprise one or more amino-lipids of the invention described above and may furthermore comprise additional lipids and other hydrophobic compounds such as sterol derivatives, e.g. cholesterol. Those additional components of a lipid nanoparticle of the present invention serve various purposes such as aiding manufacturing and storage stability as well as modulation of the biodistribution. Biodistribution may also be modulated by incorporation of targeting ligands conjugated to the lipids part of the lipid nanoparticle. Specific examples of additional components of the lipid nanoparticles are given below.

In one embodiment, lipid nanoparticles are provided that comprise the amino-lipids described above and one or more additional lipids. Additional lipids suitable to be incorporated into the lipid nanoparticles of the invention comprise cationic lipids, helper lipids and PEG lipids. Hence in one embodiment lipid nanoparticles are provided that comprise the amino-lipids described above and one or more additional lipids selected from the group of cationic lipid, helper lipid and PEG lipid. "Cationic lipids" as used herein refers to any lipid comprising a quaternary amine and are consequently permanently positively charged. The term "quaternary amine" as used herein refers to a nitrogen atom having four organic substituents. For example, the nitrogen atom in Tetramethylammonium chloride is a quaternary amine.

Examples of cationic lipids comprising a quaternary amine include, but are not limited to, N-(2,3-dioleyloxy) propyl)-N,N,N-trimethylammonium chloride ("DOTAP"), N,N,-Distearyl-N,N-dimethylammonium bromide ("DDBA"), 1-methyl-4-(cis-9-dioleyl)-methylpyridinium-chloride ("SAINT-solid"), N-(2,3-dioleyloxy)propyl)-N,N,N-triethylammonium chloride ("DOTMA"), N,N-dioleyl-N,N-dimethylammonium chloride ("DODAC"), (1,2-dimyristyloxyprop-3-yl)-N,N-dimethyl-N-hydroxyethyl ammonium bromide ("DIMRIE") and the like.

"Helper lipids", as used herein are preferably neutral zwitterionic lipids. Examples of preferred helper lipids used in this invention are 1,2-distearoyl-sn-glycero-3-phosphocholine ("DSPC"), 1,2-dipalmitoyl-sn-glycero-3-phosphocholine ("DPPC"), or any related phosphatidylcholine such as natural sphingomyelin ("SM") and synthetic derivatives thereof such as 1-oleoyl-2-cholesteryl-hemisuccinoyl-sn-glycero-3-phosphocholine ("OChemsPC"). Other preferred helper lipids include 1,2-dileoyl-sn-3-phosphoethanolamine ("DOPE"), 1,2-diphytanoyl-sn-glycero-3-phosphoethanol-amine ("ME 16.0 PE").

In one embodiment, LNPs contain uncharged lipids modified with hydrophilic polymers, e.g. polyethylene glycol (herein also referred to as "PEG-lipids") to stabilize the lipid nanoparticle and to avoid aggregation. The polyethylene glycol (PEG) size can vary from approximately 1 to 5 approximately kDa. Depending on the relative amounts of these molecules in the formulation and the length of the hydrocarbon chain, the PEG-lipid can influence the pharmacokinetic characteristics, biodistribution, and efficacy of a formulation. PEG lipids having relatively short lipid hydrocarbon chains of about 14 carbons dissociate from the LNP in vivo in plasma with a half-life of less than 1 h. In contrast, a PEG lipid with a relatively long lipid hydrocarbon chain length of about 18 carbons circulates fully associated with the formulation for several days. Hence, in one preferred embodiment, said PEG lipid comprises a lipid hydrocarbon chain of 12 to 20 carbon atoms, 14 to 18 carbon atoms, preferably of 14 carbon atoms.

Typically, the concentration of the PEG-lipid is about 0.5 to 10 mol %. Examples of suitable PEG modified lipids include pegylated ceramide conjugates, pegylated distearoylphosphatidyl-ethanolamine (PEG-DSPE). Other compounds that can be used to stabilize lipid nanoparticles include gangliosides (GMt, GM3, etc.). Preferred PEG lipids have a PEG size ranging from about 1 to about 2 KDa. Specific examples me methoxy-polyethyleneglycol-carbamoyl-dimyristyloxy-propylamine (PEG2000-c-DMA), and (α-(3'-(1,2-dimyristoyl-3-propanoxy)carboxamide-propyl]-ω-methoxy-polyoxyethylene (PEG2000-c-DOMG).

In one embodiment lipid nanoparticles are provided that comprise the amino-lipids described above and one or more hydrophobic small molecule. The term "hydrophobic small molecule" as used herein refers to a compound with a molecular weight of about 300 to about 700 Da comprising 2 or more carbon- or heterocycles providing a rigid core structure. Preferably said hydrophobic small molecule is selected from the group of sterols such as cholesterol or stigmasterol or a hydrophobic vitamin such as tocopherol. In a preferred embodiment said hydrophobic small molecule is cholesterol.

In one embodiment the lipid nanoparticle comprises an amino-lipid of the present invention, one or more additional lipids selected from the group of cationic lipid, helper lipid and PEG lipid. and a hydrophobic small molecule selected from the group of a sterol or a hydrophobic vitamin. In one embodiment said lipid nanoparticle comprises an amino-lipid of the present invention, a helper lipid selected from DSPC or DPPC, PEG-DOMG and a hydrophobic small molecule selected from the group of a sterol or a hydrophobic vitamin.

In one embodiment the lipid nanoparticle comprises an amino-lipid of the present invention, a helper lipid, a PEG modified lipid and cholesterol. In preferred embodiments the molar ratios of these components are 30-70% amino-lipid, 0-60% helper lipid, 0.1-10% PEG lipid and 0-50% cholesterol. More preferred lipid nanoparticle compositions comprise the above mentioned components in a molar ratio of about 40% to 60% amino-lipid, 0 to 20% helper lipid, 0.1% to 5% PEG lipid and 30 to 50% cholesterol. In certain other embodiments lipid nanoparticles are provided that do not comprise cholesterol. These formulations contain up to about 60 mol % of at least one helper lipid. Preferred helper lipids in these lipid nanoparticles are DSPC, SM, DOPE, 4ME16:0PE.

In one embodiment the lipid nanoparticle comprises a cyclic amino-lipid of the present invention, DSPC or SM, PEG-c-DOMG and cholesterol. Preferably, said cyclic amino-lipid has the structure of

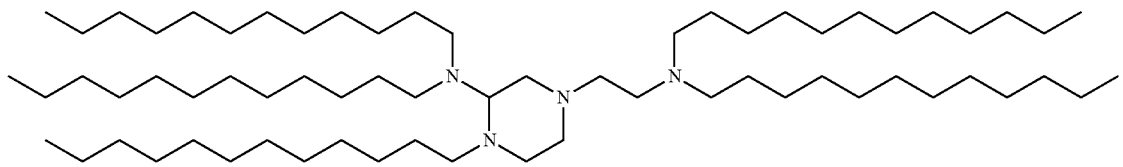

Preferred molar ratios of these components are about 50% of said cyclic amino-lipid, about 10% helper lipid, about 38% cholesterol and about 2% of the PEG lipid. Preferred N/P ratios range from approximately 6.9 to approximately 8.4.

In another embodiment cholesterol free lipid nanoparticles are provided. These comprise a cyclic amino-lipid, the helper lipids DSPC and DOPE, as well as the PEG-lipid PEG-c-DMOG. LNPs comprising these components are not taken up by Kupffer cells in the liver, but mediate functional drug delivery to hepatocytes, stellate cells and endothelial cells. Preferably said cyclic amino-lipid has the structure of

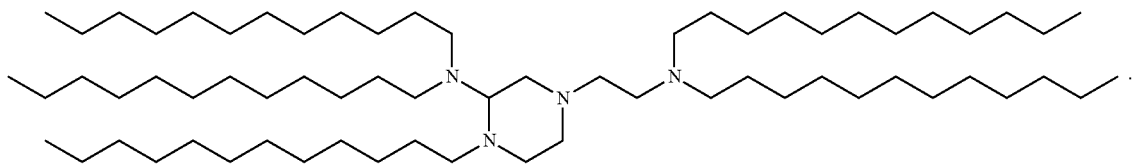 [SMILES: CCCCCCCCCCCCN(CCCCCCCCCCCC)CCN1CCN(CCCCCCCCCCCC)C(N(CCCCCCCCCCCC)CCCCCCCCCCCC)C1]

In yet another embodiment cholesterol free lipid nanoparticles comprise just one helper lipid. In this case a preferred lipid nanoparticle contains a cyclic amino-lipid, the helper lipid 4ME 16:0PE and PEG-c-DMOG. LNPs comprising these components are barely taken up by hepatocytes, but mediate functional drug delivery to Kupffer cells, stellate cells and endothelial cells.

Preferably said cyclic amino-lipid has the structure of

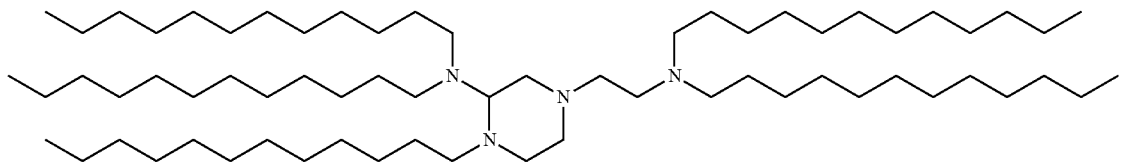

In one embodiment the lipid nanoparticle comprises an amino-lipid of the present invention, DSPC, a PEG lipid such as PEG-c-DOMG and cholesterol. Preferably, said amino-lipid has the structure of

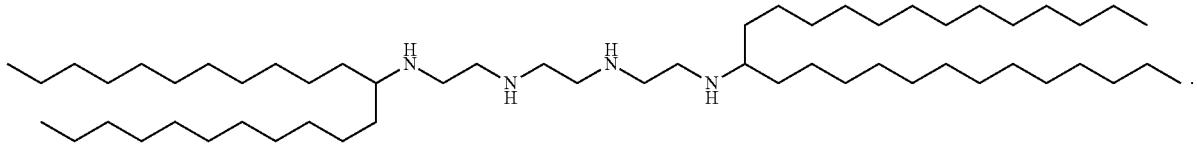 [SMILES: CCCCCCCCCCCCCC(CCCCCCCCCCCCC)NCCNCCNCCNC(CCCCCCCCCCC)CCCCCCCCCCC]

Preferred molar ratios of these components are 40% to 60% of said amino-lipid, about 0% to 20% helper lipid, about 38% cholesterol and approximately 2% of a PEG 2000 lipid. The N/P ratio preferably is at least about 15:1, more preferably at least about 10:1, even more preferably at least about 7:1, and most preferably at least about 5:1. LNPs comprising these compositions are particularly well suited to functional deliver nucleic acids into endothelial cells of various organs.

In another embodiment the lipid nanoparticle comprises an amino-lipid of the present invention, DSPC, a PEG lipid such as PEG-c-DOMG and cholesterol. Said amino-lipid has the structure of

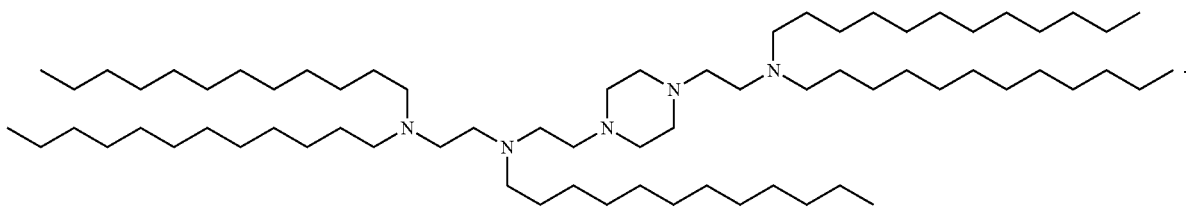 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

Preferred molar ratios of these components are 40% to 60% of said amino-lipid, about 0% to 20% helper lipid, about 30% to 40% cholesterol and about 0.5% to about 2% of a PEG 2000 lipid. The N/P ratio preferably is at least about 8:1, more preferably at least about 15:1 and most preferably at least about 10:1.

In another preferred embodiment the lipid nanoparticle comprises an amino-lipid of the present invention, DSPC, a PEG lipid such as PEG-c-DOMG and cholesterol. Said amino-lipid has the structure of

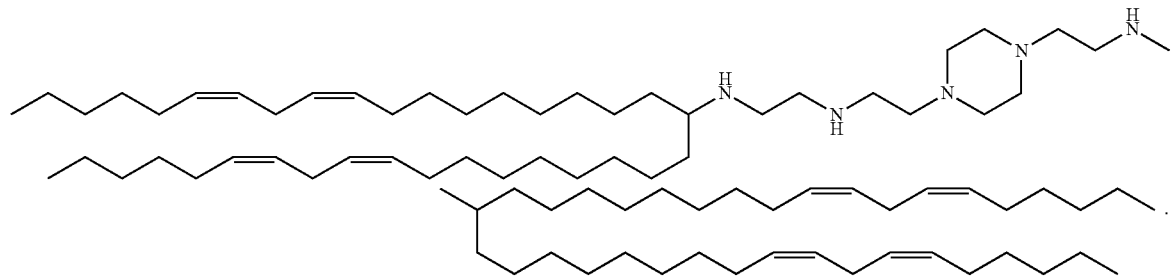

In another preferred embodiment the lipid nanoparticle comprises a cyclic amino-lipid of the present Invention, DSPC, a PEG lipid such as PEG-c-DOMG and cholesterol. Said amino-lipid has the structure of

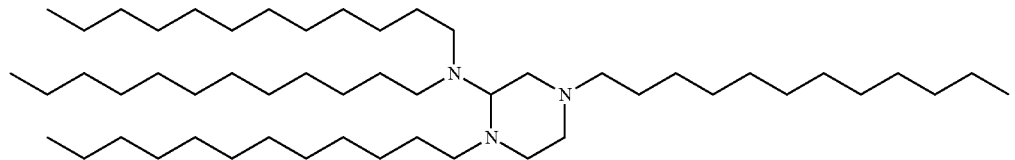

In another preferred embodiment the lipid nanoparticle comprises a cyclic amino-lipid of the present invention, DSPC, a PEG lipid such as PEG-c-DOMG and cholesterol. Said amino-lipid has the structure of

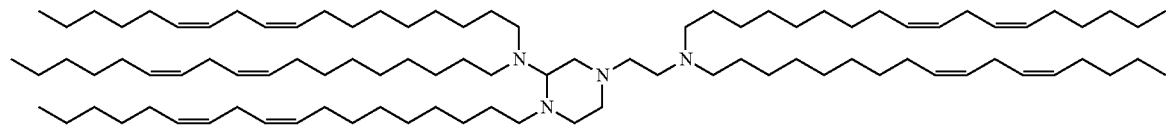

In one embodiment, the lipid nanoparticles described above are complexed with a biologically active compound. The term "complexed" as used herein relates to the non-covalent interaction of the biologically active compound with specific components of the lipid nanoparticle. In case of a nucleic acid as the biologically active compound the negatively charged phosphate backbone of the nucleic acid interacts with the positively charged amino-lipid. This interaction supports the stable entrapment of the nucleic acid into the LNP.

The term "biologically active compound" as used herein refers to an inorganic or organic molecule including a small molecule, peptide (e.g. cell penetrating peptides), carbohydrate (including monosaccharides, oligosaccharides, and polysaccharides), protein (including nucleoprotein, mucoprotein, lipoprotein, synthetic polypeptide, or a small molecule linked to a protein, glycoprotein), steroid, nucleic acid, lipid, hormone, or combination thereof, that causes a biological effect when administered in vivo to an animal, including but not limited to birds and mammals, including humans. Preferably said biologically active compound is negatively charged.

In one embodiment the lipid nanoparticles described above are complexed with a biologically active compound selected from the group of small molecule, peptide, protein, carbohydrate, nucleic acid, or lipid. Preferably said biologically effect is a therapeutic effect.

The term "nucleic acid" as used herein means an oligomer or polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Non-naturally occurring nucleic acids are oligomers or polymers which contain nucleobase sequences which do not occur in nature, or species which contain functional equivalents of naturally occurring nucleobases, sugars, or inter-sugar linkages, like peptide nucleic acids (PNA), threose nucleic acids (A), locked nucleic acids (LNA), or glycerol nucleic acids (GNA). This term includes oligomers that contain the naturally occurring nucleic acid nucleobases adenine (A), guanine (G), thymine (T), cytosine (C) and uracil (U), as well as oligomers that contain base analogs or modified nucleobases. Nucleic acids can derive from a variety of natural sources such as viral, bacterial and eukaryotic DNAs and RNAs. Other nucleic acids can be derived from synthetic sources, and include any of the multiple oligonucleotides that are being manufactured for use as research reagents, diagnostic agents or potential and definite therapeutic agents. The term includes oligomers comprising a single strand nucleic acid or a double strand nucleic acid. Examples of nucleic acids useful therein are miRNA, antisense oligonucleotides, siRNA, immune-stimulatory oligonucleotides, aptamers, ribozymes, or plasmids encoding a specific gene or siRNA.

As used herein, the term "peptide" is used to refer to a natural or synthetic molecule comprising two or more amino acids linked by an amide bond consisting of the carboxylic acid group of one amino acid and the amino group by the other amino acid. A peptide is not limited by the number of amino acids and thus it can include polypeptides and proteins.

Below embodiments are exemplified for the complexation and delivery of nucleic acids. It is understood that these embodiments are also applicable for any other biologically active compound.

The complex comprising lipid nanoparticles and one or more nucleic acid are characterized by the following parameters: (1) nucleic acid to total lipid ratio; (2) nucleic acid to amino-lipid ratio; (3) encapsulation efficacy; (4) particle size; (5) particle size distribution and (6) zeta potential.

The nucleic acid to total lipid ratio is the amount of the nucleic acid in a defined volume divided by the amount of total lipid in the same volume. Total lipid refers to all components in the particle formulations except for the nucleic acid. The ratio may be expressed on a mole per mole or weight by weight basis.

The nucleic acid so amino-lipid ratio is the amount of the nucleic acid in a defined volume divided by the amount of amino-lipid in the same volume. The ratio may be expressed on a mole per mole or weight by weight basis; but is usually expressed as nitrogen to phosphorus (N/P) ratio. The (N/P) ratio is characterized by the number of positively charged nitrogen atoms present in the amino-lipid divided by the number of negatively charged phosphorus atoms present in the nucleic acid. Encapsulation efficacy is defined as the percentage of nucleic acid that is encapsulated or otherwise associated with the lipid nanoparticle. The encapsulation efficiency is usually determined by quantifying the amount of the nucleic acid in solution before and alter breaking up the lipid nanoparticle by suitable organic solvents or detergents. A high encapsulation efficiency is a desirable feature of nucleic acid lipid nanoparticles particularly because of considerations regarding cost of goods.

The particle size of lipid nanoparticles is typically measured by dynamic light scattering. Sizes of lipid nanoparticles in a given formulation are typically distributed over a certain range The size of lipid nanoparticles is typically expressed as the mean particle size or the $Z_{average}$ value. The particle size distribution of lipid nanoparticles is expressed as the polydispersity index (PI). Particles in the size range of 30 to 300 nm are considered advantageous for in vivo applications. Lipid nanoparticles with a mean particle size less than approximately 150 nm are advantageous, in particular to assess tissues characterized by a leaky vasculature as is the case for tumor tissue or liver. Lipid nanoparticles with a mean particle size greater than approximately 150 nm are advantageous, in particular to assess macrophages.

Nucleic acid lipid nanoparticles are also characterized by their surface charge as measured by the zeta (0-potential. The basis of the measurement is the movement of particles in an electrical field as measured by dynamic light scattering. Particles with a near to neutral surface charge are advantageous for in vivo applications and are thus preferred herein.

Particularly because of cost of goods and manufacturing reasons a high encapsulation efficiency of the nucleic acids complexed with the lipid nanoparticles is desirable. Particles in the size range of 30 to 300 nm with near to neutral surface charge are known to be advantageous for in vivo applications.

C. Methods of Producing Lipid Nanoparticles (LNPs) Comprising the Inventive Amino-Lipids and Complexes Thereof with Biologically Active Compounds In general, any method known in the art can be applied to prepare the lipid nanoparticles comprising one or more amino-lipids of the present invention and to prepare complexes of biologically active compounds and said lipid nanoparticles. Examples of such methods are widely disclosed, e.g. in *Biochimica et Biophysica Acta* 1979, 557:9; *Biochimica et Biophysica Acta* 1980, 601:559; *Liposomes: A practical approach* (Oxford University Press, 1990); *Pharmaceutica Acta Helvetiae* 1995, 70:95; *Current Science* 1995, 68:715; *Pakistan Journal of Pharmaceutical Sciences* 1996, 19:65; *Methods in Enzymology* 2009, 464:343.

Below embodiments are exemplified for the complexation and delivery of nucleic acids. It is understood that these embodiments are also applicable for any other biologically active compound.

In one embodiment, the components of the lipid nanoparticles as outlined above are mixed in a solvent that is miscible with water, such as methanol, ethanol isopropanol or acetone. Preferred solvents are alcohols, most preferable ethanol. In most preferred embodiments the solvent is commercially available ethanol. In certain embodiments the lipid mixture consists of the above components in a molar ratio of about 30 to 70% amino-lipid:0 to 60% helper lipid:0.1 to 10% PEG-lipid and 0 to 50% cholesterol. More preferred lipid nanoparticle compositions comprise the above mentioned components in a molar ratio of about 40% to 60% amino-lipid, 0 to 20% helper lipid, 0.1% to 5% PEG lipid and 30 to 50% cholesterol. In certain other embodiments lipid nanoparticles lack cholesterol. These formulations contain up to about 60 mol % of a least one helper lipid. Preferred helper lipids in these lipid nanoparticles are DSPC, SM, DOPE, 4ME16-0PE.

In one embodiment, the nucleic acid is dissolved in an aqueous buffer. The pH of the buffer is such that at least one of the nitrogen atoms of the amino-lipids of the present invention will become protonated upon mixing the aqueous nucleic acid solution with the solution comprising the components of the lipid nanoparticles. Examples of appropriate buffers include, but are not limited to acetate, phosphate, citrate, EDTA and MES. Preferred concentration of the buffers are in the range of about 1 to about 500 mM. Typically the concentration of the nucleic acid in the aqueous buffer is in the range of about 0.1 to about 250 mg/mL, more preferably from about 0.5 to about 150 mg/mL.

The solution comprising the components of the lipid nanoparticles is then combined with the buffered aqueous solution of the nucleic acid. Acidic pH is preferred, particularly a pH below 6.8, more preferably a pH below 5.4 and most preferably about 4.0. Optionally, the entire mixture may be sized according to known methods, e.g. by extrusion. Particles with a mean diameter of preferably 40 to 170 nm, most preferably of about 50 to 120 nm are generated.

Subsequently, the pH is neutralized yielding an at least partially surface-neutralized nucleic acid lipid nanoparticle complex. Due to the fact that amino-lipids of the present invention have at least two nitrogen atoms, pKa values can differ substantially. Formation of complexes with nucleic acids is most supported at low pH in the range of about 3 to about 5. At a pH of about 7, at least partial surface neutralization is achieved.

In one embodiment, the ratio of lipid:nucleic acid is at least about 2:1, at least about 3:1, at least about 4:1, at least about 5:1, at least about 6:1, at least about 7:1, at least about 8:1, at least about 10:1, at least about 15:1.

Techniques to combine the solutions comprising the components of the lipid nanoparticles and the buffered aqueous solution of the nucleic acid can vary widely and may be dependent on the scale of production. Preparations in the range of a few mL may be made by pipetting one solution into the other followed by mixing with e.g. a vortex mixture. Larger volumes can be preferentially prepared by a continuous mixing method using pumps, e.g. a piston pump such as Pump 33 (Harvard Apparatus) or most preferably HPLC pumps such as AKTA pumps (GE Healthcare). With the aid of such pumps the two solutions are pumped out of their individual reservoirs and combined by delivering the fluids through a suitable connector piece or mixing chamber. By varying the concentrations of the two solutions and their flow rates, the mean size of the resulting lipid nanoparticles can be controlled within a certain range. Preferably, the compositions provided herein are sized to a mean diameter from about 50 nm to about 200 nm, more preferably about 50 nm to about 150 nm and most preferably about 50 nm to 120 nm.

In certain embodiments, methods of the present invention further comprise a processing step that ensures the substantial removal of the solvent that was used to dissolve the lipid mixture and to exchange the buffer used to dissolve the therapeutically active agent. Suitable techniques to carry out this processing step include, but are not limited to diafiltration or tangential flow filtration. For buffer exchange a physiologically compatible buffer such as phosphate or HEPES buffered saline with a pH of about 7.4 or 5% dextrose solution (DSW) is used.

Optionally, nucleic acid lipid nanoparticles can be produced using the lipid film hydration method followed by extrusion. In this case, the components of the lipid nanoparticle, i.e. one of the amino-lipids as described in the present invention, a helper lipid, a PEG-lipid (e.g. PEG-c-DOMG) and a sterol, e.g. cholesterol, are dissolved in an organic solvent such as chloroform. The solvent is evaporated yielding a thin lipid film, which is subsequently hydrated with an aqueous buffer containing the therapeutically active agent to form the desired lipid nanoparticle. Alternatively, the lipid film is hydrated with buffer and the nucleic acid is added in a subsequent incubation step.

D. Pharmaceutical Compositions and Medical Uses

In another object the present invention relates to a pharmaceutical composition comprising the amino-lipids of the invention. Preferably said pharmaceutical composition comprises the lipid nanoparticles of the present invention and a biologically active compound. In one embodiment said biologically active compound is selected from the group of a small molecule, a peptide, a protein or a nucleic acid. In a preferred embodiment, said biologically active compound is a nucleic acid. Examples of nucleic acids useful therein are miRNA, antisense oligonucleotides, siRNA, immune-stimulatory oligonucleotides, aptamers, ribozymes, or plasmids encoding a specific gene or siRNA.

The pharmaceutical compositions provided herein may additionally contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the lipid nanoparticles of the present invention, which may be used in a suitable hydrated form, and/or the pharmaceutical compositions of the present invention, are formulated into pharmaceutically acceptable dosage forms by conventional methods known to those of skill in the art.

The phrases "administration" and "administered" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition must b sterile and fluid to the extent that the composition is deliverable through syringe or infusion techniques. In addition to water, the carrier is preferably an isotonic sugar solution and most preferably an isotonic buffered saline solution.

Proper fluidity can be maintained, for example, by use of costing such as lecithin, by maintenance of required particle size and by use of surfactants. In many cases, it is preferable to include isotonic agents, for example, sugars, polyalcohols such as mannitol or sorbitol, and sodium chloride in the composition.

In another object the present invention relates to the use of the lipid nanoparticles of the invention complexed to a biologically active compound as a medicament for treatment of a disease. In one embodiment the biologically active compound is a nucleic acid that may comprise a single strand or a double strand DNA or RNA which may or may not be chemically modified. Examples of nucleic acids useful therein are miRNA, short interfering RNA (siRNA), antisense oligonucleotides, immune-stimulatory oligonucleotides, aptamers, ribozymes, or plasmids encoding a specific gene or a siRNA. In particular embodiments the biologically active compound is a short interfering RNA (siRNA) and is complexed with the lipid nanoparticles of the present invention, thus enabling intracellular delivery of said biologically active compound.

In one embodiment the present invention provides a method of treating a disease that is caused by the overexpression of one or several proteins in a subject, said method comprising administration of the a pharmaceutical composition of the present invention to said subject. The pharmaceutical composition comprises the LNP of the invention and a biologically active compound selected from the group of siRNA, miRNA, antisense oligonucleotides, ribozyme or a plasmid encoding for an siRNA, all being able to interfere with the expression of the disease causing protein(s).

In another embodiment, the present invention provides a method of treating a disease that is caused by a reduced expression or a suppressed expression of one or several proteins in a subject, said method comprising administration the pharmaceutical composition of the present invention to the subject. The pharmaceutical composition comprises the LNP of the invention and a biologically active compound selected from the group of a plasmid encoding for the corresponding protein(s) or a nucleic acid that interferes with the suppressor molecule.

In yet another embodiment, the present invention provides for a method of generating an immune response in a subject upon administration of a pharmaceutical composition of the present invention to said subject. The pharmaceutical composition comprises the LNP of the invention and a biologically active compound, wherein the biologically active compound is an immune-stimulatory nucleic acid such as a CpG oligonucleotide. As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

EXAMPLES

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1

Amino-Lipids

Examples of amino-lipids of the present invention synthesized by reaction of an amine and a carbonyl compound under reductive amination conditions are listed in Table 1. Solvents and reagents were purchased from Sigma Aldrich (Taufkirchen, Germany) or TCI Europe (Eschborn, Germany) and were used as received (FIG. 1).

A) General Synthesis Procedure for Amino-Lipids Generated by Reaction of Amines and Aldehydes.

The aldehydes needed for the preparation of KL5, KL6 KL7, KL8, KL12, KL15, KL16, KL34, KL35, KL37 were prepared by oxidation of the corresponding alcohols using 2-Iodoxybenzoic acid (IBX) according to the following general procedure:

The alcohol was dissolved in anhydrous ethyl acetate (EtOAc, 10 mL/1.0 mmol). IBX (1.1 eq) was added to form a suspension. The mixture was stirred briskly and refluxed at 80° C. under Argon. DMSO (2.2 eq.) was added via a syringe and the suspension was refluxed for 1.5 h. The insoluble o-iodobenzoic acid by-product was filtered off. The solvent was removed under reduced pressure and the crude product purified by flash-chromatography (Hexan-Hexcan/EtOAc=10:1, Rf=0.35 in Hexan/EtOAc=5:1). The final products were characterized by HPLC and mass spectrometry.

Ether containing alcohols were prepared following a published procedure (*Bioconjugate Chemistry* 2006, 19:1283). The subsequent oxidation to the corresponding aldehyde was spin accomplished with IBX according to the procedure given above.

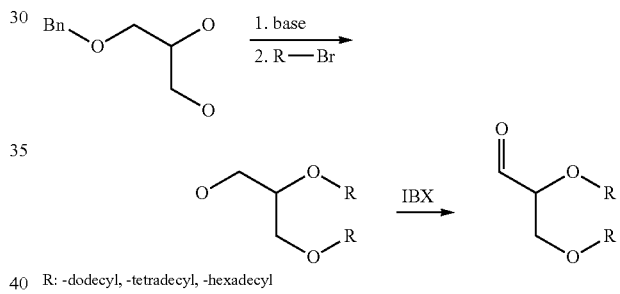

R: -dodecyl, -tetradecyl, -hexadecyl

The aldehydes needed for the preparation of KL52 and KL56 were synthesized by oxidation of the corresponding alcohols employing pyridinium chlorochromate (PCC) in Dichloromethane according to standard procedures (*Synthesis*, 1982, 245). Other aldehydes are commercially available. The amine in KL12, KL22, KL33, KL34 and KL35 was made pursuing a published synthesis route (*PNAS* 2010, 5:1864).

B) Preparation of N-Peralkylated Amino-Lipids.

KL4, KL9, KL22, KL33, KL34, KL35, KL36, KL37, KL51, KL52, KL53, and KL56 were prepared by combining the corresponding aldehyde and corresponding amine in dichloroethane (DCE) in a ratio of 1.75 equivalents per amino function of the amine. To this solution was added at room temperature sodium triacetoxyborohydride (NaBH(OAc)$_3$) (1.3 equivalents per aldehyde) and acetic acid (HOAc, 1.3 equivalents per aldehyde). The reaction mixture was stirred at ambient temperature until thin layer chromatography indicated completion of reaction. After hydrolysis with 2N NaOH, the reaction mixture was extracted twice with dichloromethane (DCM). The combined organic layers were washed with saturated NaCl solution and dried over Na$_2$SO$_4$. The solvent was removed under reduced pressure and the crude product was subject to flash chromatography or reversed phase (RP) HPLC.

Amino-lipids were analyzed for purity using analytical reversed phase HPLC. For this purpose, an XBridge C4 column (2.1×50 mm, 3.5 μm) from Waters (Eschborn, Germany) was used. Eluent was A 0.1% TFA in water and eluent B was 0.1% TFA in 90% Acetonitrile (ACN). Elution was achieved at a column temperature of 60° C. running a gradient from 50% to 100% B in 20 min at a flow rate of 0.5 mL/min. Amino-lipids were detected using an evaporative light scattering detector (PL-ELS 2100, Agilent, Waldbronn, Germany) with evaporation temperature set to 90° C., nebulizer temperature set to 40° C. and a nitrogen flow of 1 mL/sec. Identity was established by electrospray ionization (ESI) mass spectrometry (MS) and direct infusion technique.

1) Synthesis of KL22.

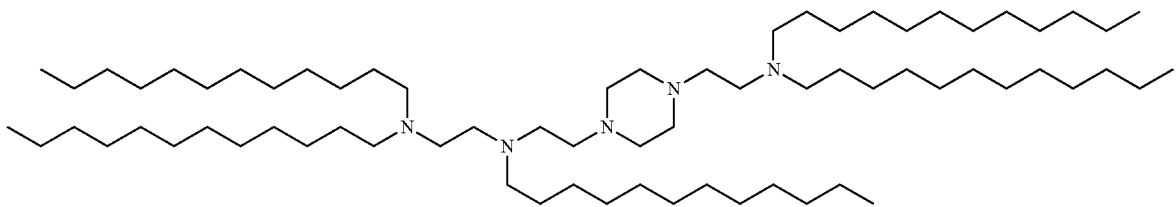

To a solution of Dodecanal (11.6 g 62.8 mmol, 9.0 eq, 1.75 eq/amine function) and 2-[4-(2-Amino-ethyl)-piperazin-1-yl]-ethyl)-ethane-1,2-diamine (1.5 g, 7.0 mmol. 1.0 eq) in 100 mL dichloroethane (DCE) was added sodium triacetoxyborohydride (NaBH(OAc)$_3$) (17.3 g, 81.6 mmol, 11.7 eq) and acetic acid (HOAc) (81.6 mmol, 5.0 mL) at room temperature. The reaction mixture was stirred for 16 h at ambient temperature. After hydrolysis with 2N NaOH the reaction mixture was extracted twice with dichloromethane (DCM). The combined organic layers were washed with saturated NaCl-solution and dried over Na$_2$SO$_4$. The solvent was removed under reduced pressure and the crude product was subject to flash chromatography (DCM-DCM/CH$_3$OH=100:6, Rf=0.05 in DCM/CH$_3$OH=100:1 (0.5% NEt$_3$)) to afford the title compound as a pale yellow oil.

ESI-MS (direct infusion): [M+H]+: 1058.5

A comparison of crude synthesis products obtained by an alternate peralkylation procedure (ring opening reaction of terminal epoxides by amines) detailed in WO2010/053572A2 and PNAS 2010, 5:1864 underscores the high efficiency of the chemistry disclosed herein allowing for high isolated yields (FIG. 1).

2) Synthesis of KL10.

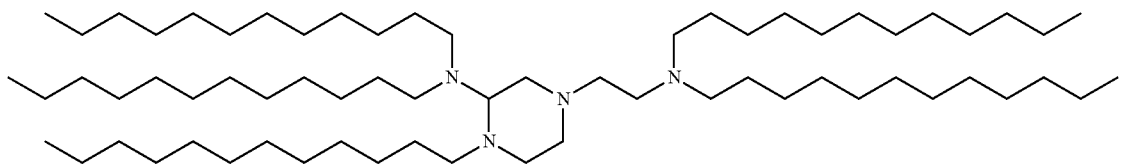 [SMILES: CCCCCCCCCCCCN(CCCCCCCCCCCC)CCN1CCN(CCCCCCCCCCCC)C(N(CCCCCCCCCCCC)CCCCCCCCCCCC)C1]

To a solution of Dodecanal (15.1 g, 82.1 mmol, 6.0 eq) and Tris-(2-aminoethyl)-amine (2.0 g 13.7 mmol. 1.0 eq) in 100 mL DCE was added NaBH(OAc)$_3$ (26.1 g, 123.1 mmol, 9.0 eq) and HOAc (123.1 mmol, 7.0 mL) at room temperature. The reaction mixture was stirred for 16 h at ambient temperature. After hydrolysis with 2N NaOH the reaction mixture was extracted twice with DCM. The combined organic layers were washed with saturated NaCl-solution and dried over Na$_2$SO$_4$. The solvent was removed under reduced pressure and the crude product was subject to flash chromatography (DCM-DCM/CH$_3$OH=10:1-DCM/CH$_3$OH=5:1, Rf=0.01 in DCM (0.5% NEt$_3$)) to concentrate the title compound as a pale yellow oil. KL10 was further purified to homogeneity using RP HPLC. ESI-MS (direct infusion): [M+H]+: 986.1

3) Synthesis of KL36.

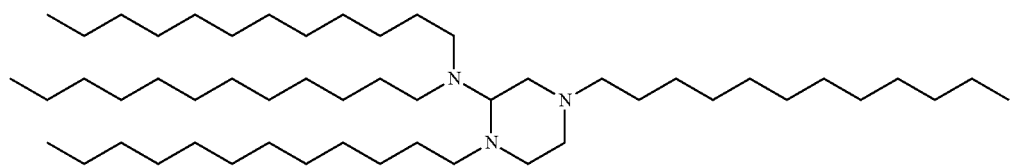 [SMILES: CCCCCCCCCCCCN1CCN(CCCCCCCCCCCC)C(N(CCCCCCCCCCCC)CCCCCCCCCCCC)C1]

To a solution of Dodecanal (3.22 g, 17.5 mmol, 4.5 eq) and Diethylentriamine (0.40 g, 3.88 mmol. 1.0 eq) in 50 mL DCE was added NaBH(OAc)$_3$ (5.56 g, 26.3 mmol, 6.75 eq) and HOAc (26.3 mmol, 1.6 mL) at room temperature. The reaction mixture was stirred for 16 h at ambient temperature. After hydrolysis with 2N NaOH the reaction mixture was extracted twice with DCM. The combined organic layers were washed with saturated NaCl-solution and dried over Na$_2$SO$_4$. The solvent was removed under reduced pressure and the crude product was subject to flash chromatography (DCM-DCM/CH$_3$OH=10:1-DCM/CH$_3$OH=5:1, Rf=0.01 in DCM (0.5% NEt$_3$)) to concentrate the tide compound as a pale yellow oil and to remove the excess aldehyde. The crude product was finally purified by HPLC employing a C4 reversed phase column (YMC-Pack C4, 150×20 mm, 10 µm. Dienslaken, Germany). Eluent A was HO containing 0.1% Trifluoroacetic acid (TF A) and eluent B was 90% ACN containing 0.1% TFA. For elution at room temperature, a gradient from 70-100% Eluent B and a flow rate of 45 mL/min was used. 5 ESI-MS (direct infusion): [M+H]+: 776.7

4) Synthesis of KL37.

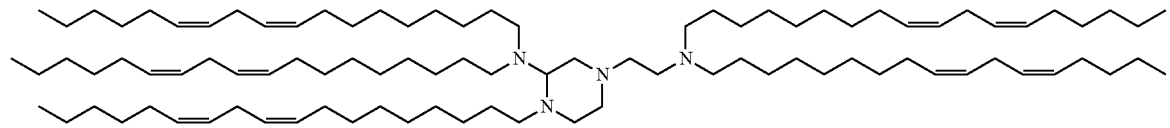

To a solution of octadecanal (1.20 g, 4.51 mmol, 5.5 eq) and Tris-(2-aminoethyl)-amine (0.12 g, 0.82 mmol. 1.0 eq) in 50 mL DCE was added NaBH(OAc)$_3$ (1.43 g, 6.77 mmol, 6.75 eq) and HOAc (6.77 mmol, 0.4 mL) at room temperature. The reaction mixture was stirred for 16 h at ambient temperature. After hydrolysis with 2N NaOH, the reaction mixture was extracted twice with DCM. The combined organic layers were washed with saturated NaCl-solution and dried over Na$_2$SO$_4$. The solvent was removed under reduced pressure and the crude product was subject to flash chromatography (DCM-DCM/CH$_3$OH=10:1-DCM/CH$_3$OH=5:1, Rf=0.01 in DCM (0.5% NEt$_3$)) to concentrate the tide compound as a pale yellow oil and to remove the excess aldehyde. The crude product was finally purified by HPLC on a C4 reversed phase column (YMC-Pack C4, 150×20 mm, 10 µm). Eluent A was H$_2$O containing 0.1% Trifluoroacetic acid (TFA) and eluent B was 90% ACN containing 0.1% TFA. For elution at room temperature, a gradient from 70-100% Eluent Band a flow rate of 45 mL/min was used.

ESI-MS (direct infusion): [M+H]+: 1386.2

C) Preparation of Selectively Alkylated Amino-Lipids.

Amino-lipids KL5, KL6, KL7, KL8, KL42, KL15, KL16, were generated by a stepwise synthetic protocol published in *J Org Chem.* 1996, 61:3849-3862:

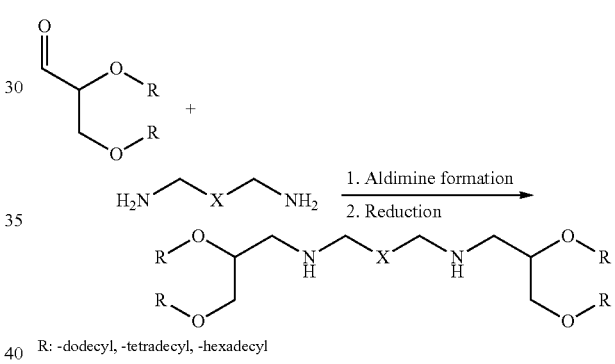

R: -dodecyl, -tetradecyl, -hexadecyl

The corresponding aldehyde (2.0 eq) and amine (1.0 eq) were mixed in MeOH (20 mL/1.0 mmol) at room temperature under an Argon atmosphere. The mixture was stirred at ambient temperature for 3 h, until the aldimine formation was completed. The solvent was removed under reduced pressure and the crude product was dissolved in DCE (20 mL/1.0 mmol) and treated with NaBH(OAc)$_3$ (3.0 eq) and AcOH (3.0 eq) and stirred under Argon for 3 h. The reaction was quenched with 2M NaOH and the product was extracted with EtOAc. The combined organic layers were dried over Mg$_2$SO$_4$ and the solvent was evaporated under reduced pressure. The crude product was subject to flash chromatography (DCM-DCM/MeOH=9:1, Rf 0.25 in DCM/MeOH=0:1 (0.5% NEt$_3$)) to afford the desired compound as a pale yellow oil. The final product was characterized by HPLC and mass spectrometry.

D. General Synthesis Procedure for Amine-Lipids Derived from Amines and Ketones.

The ketone needed for the preparation of KL32 and KL39 was prepared in 4 steps according to a published synthesis route (*Nature Biotechnology* 2010, 28:172). Other ketones are commercially available. The amine in KL23, KL30 and KL39 was made pursuing a published synthesis route (PNAS 2010, 5:1864).

The amino-lipids KL23, KL24, KL25, KL26, KL27, KL28, KL30, KL32, KL39, KL43, KL49 and KL58 were prepared by combining the corresponding ketone and the corresponding amine in DCE in a ratio of one equivalent of ketone per mine group. Subsequently, NaBH(OAc)$_3$ (3.0 eq) and HOAc was added and stirred at room temperature until thin layer chromatography indicated completion of reaction. The reaction mixture was worked up by addition of 2N NaOH and extraction with DCM. The organic phase was dried and the solvent removed under reduced pressure. The amino-lipids were purified by flash column chromatography and analyzed by analytical reversed phase HPLC and direct infusion ESI-MS.

1) Preparation of KL25.

RNA and 2'-O-Methyl RNA phosphoramidites were obtained from SAFC Proligo (Hamburg, Germany). Specifically, 5'-O-(4,4'-dimethoxytrityl)-3'-O-(2-cyanoethyl-N,N-diisopropyl) phosphoramidite monomers of uridine (U), 4-N-acetylcytidine ($C^{Ac}$), 6-N-benzoyladenosine ($A^{bz}$) and 2-N-isobutyrlguanosine ($G^{iBu}$) with 2'-O-t-butyldimethylsilyl were used to build the oligomers sequence. 2'-O-Methyl modifications were introduced employing the corresponding phosphoramidites carrying the same nucleobase protecting groups as the regular RNA building blocks. Coupling time for all phosphoramidites (100 mM in Acetonitrile) was 6 min employing 5-Ethylthio-1H-tetrazole (ETT) as activator (0.5 M in Acetonitrile). Phosphorothioate linkages were introduced using 50 mM 3-((Dimethylamino-methylidene) amino)-3H-1,2,4-dithiazole-3-thione (DDTT, AM Chemicals, Oceanside, Calif., USA) in a 1:1 (v/v) mixture of pyridine and Acetonitrile. Upon completion of the solid phase synthesis oligoribonucleotides were cleaved from the solid support and deprotected using slight modification of published methods (Wincott F. et al. "Synthesis, deprotection, analysis and purification of RNA and ribozymes." *Nucleic Acids Res* 1995, 23:2677-2684).

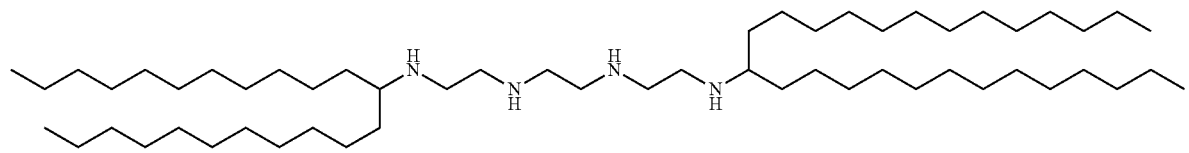 [SMILES: CCCCCCCCCCCCCC(CCCCCCCCCCCCC)NCCNCCNCCNC(CCCCCCCCCCC)CCCCCCCCCCC]

To a solution of Heptacosan-14-one (11.0 g. 27.9 mmol, 2.0 eq, 1.0 eq/amine function) and Triethylenetetraamine (2.03 g, 13.9 mmol. 1.0 eq) in 200 mL DCE was added NaBH(OAc)$_3$ (8.90 g, 41.9 mmol, 3.0 eq) and HOAc (41.9 mmol, 2.5 mL) at room temperature. The reaction mixture was stirred for 72 h at ambient temperature. After hydrolysis with 2N NaOH the reaction mixture was extracted twice with DCM. The combined organic layers were washed with saturated NaCl solution and dried over Na$_2$SO$_4$. The solvent was removed under reduced pressure and the crude product was subject to flash chromatography (DCM-DCM/CH$_3$OH=10:1-DCM/CH$_3$OH 5:1, Rf=0.3 in DCM/CH$_3$OH=4:1 (0.1% aq. NH$_3$)) to afford the title compound as a pale yellow wax.

ESI-MS (direct infusion): [M+H]+: 904.0

Example 2 siRNA Synthesis siRNAs were synthesized by standard solid phase RNA oligomerization using the phosphoramidite technology. Depending on the scale either an ABI 394 synthesizer (Applied Biosystems) or an Äkta oligopilot 100 (GE Healthcare, Freiburg, Germany) was used. In order to increase siRNA stability and abrogate immune responses, 2'-O-methyl modified nucleotides were placed within certain positions in the siRNA duplex. Ancillary synthesis reagents, Crude oligomers were purified by anionic exchange HPLC using a column packed with Source Q15 (GE Healthcare) and an Äkta Explorer system (GE Healthcare). Buffer A was 10 mM sodium perchlorate, 20 mM Tris, 1 mM EDTA, pH 7.4 (Fluka, Buchs, Switzerland) and contained 20% Acetonitrile. Buffer B was the same as buffer A with the exception of 500 mM sodium perchlorate. A gradient of 22% B to 42% B within 32 column volumes (CV) was employed. UV traces at 280 em were recorded. Appropriate fractions were pooled and precipitated with 3M NaOAc, pH 5.2 and 70% ethanol. Finally, the pellet was washed with 70% ethanol.

Isolated RNAs were shown to be at least 85% pure by analytical strong anion exchange chromatography. Identity of the RNA single strands was confirmed by LC-ESI-MS.

siRNAs were prepared by combining equimolar amounts of the complementary RNA strands in sodium citrate buffer (10 mM Na-Citrate, 30 mM NaCl, pH 6), heating to 70° C. for 5 min and slow cooling to room temperature over a time period of 2 h. siRNAs were further characterized by capillary gel electrophoresis and were stored frozen until use.

siRNA sequences are listed in Table 2. As indicated in the table, these siRNAs are directed against gene targets that are exclusively expressed in certain cells in the liver. In certain embodiments the individual sIRNAs were employed in the inventive formulations. In certain other embodiments a mixture of all the indicated siRNAs were incorporated into the inventive formulations to address siRNA delivery to other cell types than hepatocytes. Those additional cell types are listed in Table 2 as well.

TABLE 2 siRNAs employed in LNPs of the present invention.

| Duplex-ID | ssRNA ID | Sequence 5'-3' | type | Target | Cell type |
|---|---|---|---|---|---|
| 1/2 | 1 | GcAAAGGcGuGccAAcucAdTsdT | s | Factor VII | hepatocytes |
| 1/2 | 2 | UGAGUUGGcACGCCUUUGCdTsdT | as | | |
| 3/4 | 3 | AcGucuAuAucAuGGccGAdTsdT | s | EGFP | ubiquitous |
| 3/4 | 4 | UCGGCcAUGAuAuAGACGUdTsdT | as | | |
| 7/8 | 7 | cuuuucucGuGAcAAGAAGAdTsdT | s | CLEC4F | Kupffer cells |
| 7/8 | 8 | CUUCUUGUcACGAGAAAAGdTsdT | as | | |
| 9/10 | 9 | GGucucAAGccAcucGuuudTsdT | s | RELN | Stellate cells |
| 9/10 | 10 | AAACGAGUGGCUUGAGACCdTsdT | as | | |
| 11/12 | 11 | GAAGAuGcAGuGAuuuAcAdTsdT | s | TEK | endothelial cells |
| 11/12 | 12 | UGuAAAUcACUGcAUCUUCdTsdT | as | | |
| 13/14 | 13 | GcGcAGAAuucAucucuucdTsdT | s | CD68 | Macrophages |
| 13/14 | 14 | GAAGAGAUGAAUUCUGCGCdTsdT | as | | |
| 15/16 | 15 | cuGGcuGAAuuucAGAGcAdTsdT | s | CD45 | Leukocytes |
| 15/16 | 16 | UGCUCUGAAAUUcAGCcAGdTsdT | as | | |
| 5/6 | 5 | AAcGAGAAGcGcGAucAcAdTsdT | s | EGFP | Ubiquitous |
| 5/6 | 6 | UGUGAUCGCGCUUCUCGUUdTsdT | as | | |
| 17/18 | 17 | agAuGGAuAuAcucAAuuAdTsdT | s | Clec7a | Macrophages |
| 17/18 | 18 | uAAUUGAGuAuAUCcAUCUdTsdT | as | | |

Key:
Upper case letters A, C, G, U represent RNA nucleotides;
lower case letters a, c, g, u, are 2'-O-Methyl nucleotides.
A phosphorothioate linkage is symbolized with a lower case "s".
dT is deoxythimidine.

Example 3

Lipid Nanoparticles

A. siRNA Lipid Nanoparticle Preparation.

Helper lipids were purchased from Avanti Polar Lipids (Alabaster, Ala., USA). PEGylated lipids were obtained from NOF (Bouwelven, Belgium). Small molecules such as cholesterol were purchased from Sigma-Aldrich (Taufkirchen, Germany).

Lipid nanoparticles containing siRNAs as described in the section below were compared against a standard formulation containing the lipid 2,2-dilinoleyl-4-dimethylaminoethyl-[1,3]-dioxolane (XTC2) discovered by Tekmira Pharmaceuticals. XTC2 was synthesized according to published procedures (Nature Biotechnology, 2010, 28:172). The corresponding standard formulation was prepared, unless otherwise stated, according to a published composition (PNAS, 2010, 107:1854). For this purpose, stock solutions of 1,2-distearoyl-3-phosphatidylcholine (DSPC, 10%), XTC2 (50%), cholesterol (38.5%), and α-[3'-(1,2-dimyristoyl-3-propanoxy)-carboxamide-propyl]-ω-methoxy-polyoxyethylene (PEG-c-DOMG 1.5%) were prepared at concentrations of 50 mM in ethanol.

The inventive lipid nanoparticle formulations of the present invention contain the amino-lipids disclosed herein instead of XTC2. Initially, the other components were kept unchanged.

siRNA stock solutions at a concentration of 10-20 mg/mL in 10 mM sodium citrate buffer, 30 mM NaCl, pH 6 were diluted in 50 mM citrate buffer, pH 4 to the desired total siRNA concentration (~1 mg/mL).

siRNA lipid nanoparticles were manufactured at a total lipid to siRNA mass ratio of 7 by combining the lipid solution in ethanol with the buffered siRNA solution in a mixing tee (e.g. CM1XPK, VICI AG International, Schenkon, Switzerland) by using either a Harvard Pump 33 Syringe Pump (Harvard Apparatus Holliston, Mass.) or for larger batches (>15 mL) an Äkta 900 HPLC Pump (GE Healthcare Bio-Sciences Corp., Piscataway, N.J.). Flow rates ranged from (17 mL/min to 67 mL/min for the siRNA solution and from 8 mL/min to 33 mL/min for the lipid solution.

Subsequent to the initial testing in mice efficacious siRNA lipid nanoparticle formulations were further optimized. Formulation variations were generated by variation of the compositions. Differences between formulations reflect differences in the lipid species or differences in the molar percentages of the lipid components, or differences in the ratio between positively and negatively charged components of the formulation.

The primary product, i.e. the product resulting by combining the two input solutions, was dialyzed 2× against phosphate buffered saline (PBS), pH 7.4 at volumes 100× of that of the primary product using Spectra/Por dialysis tubing (Spectrum Europe B.V., Bred, The Netherlands) with a MWCO of 100 or 250 kDa (CE, or PVDF membrane) or using Slide-A-Lyzer cassettes (Thermo Fisher Scientific Inc. Rockford, Ill.) with a MWCO of 10 kD (RC membrane).

If desired siRNA lipid nanoparticles were concentrated at a 4° C. by using Vivaspin 20 centrifugation tubes (Sartorius AG, Gottingen, Germany) with a MWCO of 50 kD at 700 g using a table-top centrifuge.

The lipid nanoparticle suspension was filtered through a Filtropur S 0.2 filter with a pore size of 0.2 µm (Sarstedt, Numbrecht, Germany) and filled into glass vials with a crimp closure.

B. siRNA Lipid Nanoparticle Characterization.

To determine the siRNA concentration, formulations were diluted to a theoretical siRNA concentration of approximately 0.02 mg/mL in phosphate buffered saline (PBS). A volume of 100 μL of the diluted formulation was added to 900 μL of a 4:1 (vol/vol) mixture of methanol and chloroform. After vigorous mixing for 1 min, the absorbance spectrum of the solution was recorded at wavelengths between 230 nm and 330 nm on a DU 800 spectrophotometer (Beckman Coulter, Beckman Coulter, Inc., Brea, Calif.). The siRNA concentration in the liposomal formulation was determined based on the extinction coefficient of the siRNA used in the formulation. If extinction coefficient was not known, an average value of 22 OD/mg was used. The siRNA concentration was calculated based on the difference between the absorbance maximum at a wavelength of ~260 nm and the baseline value at a wavelength of 330 nm.

To determine the mean size of siRNA lipid nanoparticles, formulations were diluted in PBS to a concentration of approximately 0.05 mg/mL siRNA in a disposable polystyrene cuvette. The mean particle size was determined by using a Zetasizer Nano ZS (Malvern Instruments Ltd, Malvern, Worcestershire, UK).

To determine the zeta potential of siRNA lipid nanoparticles, formulations were diluted in PBS, pH 7.4 and in citrate buffer, pH 4 to a concentration of approximately 0.01 mg/mL siRNA in a disposable zeta cell (DTS1060C, Malvern Instruments Ltd, Malvern, Worcestershire, UK). The zeta potential was determined by using a Zetasizer Nano ZS (Malvern Instruments Ltd, Malvern, Worcestershire, UK).

To determine the percentage of siRNA entrapped in lipid nanoparticles the Quant-iT™ RiboGreen® RNA assay (invitrogen Corporation Carlsbad, Calif.) was used according to the manufacturer's instructions. In brief, samples were diluted to a concentration of approximately 5 μg/mL in TE buffer (10 mM Tris-HCl, 1 mM EDTA, pH 7.5). Volumes of 50 μL of the diluted samples were transferred to a polystyrene 96 well plate. To the samples, either 50 μL of TE buffer or 50 μL of a 2% Triton X-100 solution was added. The plate was incubated as 35° C. for 15 min. The RiboGreen reagent was diluted 1:100 in TE buffer and a volume of 100 μL of was added to each well. The fluorescence intensity in each well was determined using a fluorescence plate reader (Wallac Victor 1420 Multilabel Counter Perkin Elmer, Waltham, Mass.) at an excitation wavelength of ~480 nm and an emission wavelength of ~520 nm. The fluorescence values of the reagent blank were subtracted from that of each of the samples and siRNA concentrations were determined based on a standard curve of fluorescence intensities versus RNA concentrations. The percentage of free siRNA was determined by dividing the fluorescence intensity of the intact sample (without addition of Triton X-100) by the fluorescence value of the disrupted sample (with addition of Triton X-100).

Example 4

Animal Experiments

Mice (strain C57BL/6) were obtained from Charles River (Sulzfeld, Germany) or were bred in house (EGFP transgenic mice in C57Bl/6 background) and were between 6 and 8 weeks 30 old at the time of the experiments. Intravenously administered LNPs were injected by infusion of 200 μL into the tail vein. LNPs administered to the lung were orotracheally instilled by applying 50 μL into the pharynx of isoflurane anaesthetized mice and making mice breathe in the LNP solution while blocking their obligate nose breathing. 48 h post administration, mice were anaesthetized by $CO_2$ inhalation and sacrificed by cervical dislocation. Blood was collected during the experiment by submandibular vein bleed or—after sacrificing the animals—by cardiac puncture and serum isolated with serum separation tubes (Greiner Bio-One, Frickenhausen, Germany). Factor VII protein levels were analyzed by a chromogenic assay (see below). For preparation of bronchoalveolar lavage (BAL) fluid, the lungs were flushed 3× with 1 ml PBS via a intratracheally inserted canula and cells were pelleted by centrifugation. For quantitation of mRNA levels, organs were harvested and organ homogenates were prepared. Tissues were snap frozen in liquid nitrogen and powdered with mortar and pestle on dry ice. 30-50 mg of tissue was transferred to a chilled 1.5 mL reaction tube. 1 mL Lysis Mixture (Epicenter Biotechnologies, Madison, USA) and 3.3 μL Proteinase K (50 μg/μL) (Epicenter Biotechnologies, Madison, USA) was added and tissues were lysed by sonication for several seconds using a sonicator (HD2070, Bandelin, Berlin, Germany) and digested with Proteinase K for 15 min at 65° C. in a thermomixer (Thermomixer comfort, Eppendorf, Hamburg Germany). BAL lysates were obtained by resuspending BAL cells in 200 μL Lysis Mixture, followed by incubation at 53° C. for 30 min. Lysates were stored at −80° C. until analysis. For mRNA analyses, lysates were thawed and mRNA levels were measured using either QuantiGene 1.0 or Quantigene 2.0 branched DNA (bDNA) Assay Kit (Panomics, Fremont, Calif., USA, Cat-No: QG0004) according to the manufacturer's recommendations. In order to assess the FVII, EGFP, Clec4f, RELN, TEK, CD45, CD68, Clec7a and GAPDH mRNA content, the following probe sets were employed:

TABLE 3

Quantigene 1.0 probe sets.

| Oligo Name | Sequence 5' → 3' | SEQ ID No. | mRNA |
|---|---|---|---|
| mGAP 2001 | gagagcaatgccagccccTTTTTctcttggaaagaaagt | 19 | mouse GAPDH |
| mGAP 2002 | ggtccagggtttcttactccttgTTTTTctcttggaaagaaagt | 20 | mouse GAPDH |
| mGAP 2003 | ccctaggccctcctgttattTTTTTctcttggaaagaaagt | 21 | mouse GAPDH |
| mGAP 2004 | tgcagcgaactttattgatggTTTTTctcttggaaagaaagt | 22 | mouse GAPDH |
| mGAP 2005 | gcacgtcagatccacgacgTTTTTaggcataggacccgtgtct | 23 | mouse GAPDH |
| mGAP 2006 | ggcaggtttctccaggcgTTTTTaggcataggacccgtgtct | 24 | mouse GAPDH |

TABLE 3-continued

Quantigene 1.0 probe sets.

| Oligo Name | Sequence 5' → 3' | SEQ ID No. | mRNA |
|---|---|---|---|
| mGAP 2007 | gccctcagatgcctgcttcaTTTTTaggcataggacccgtgtct | 25 | mouse GAPDH |
| mGAP 2008 | gccgtattcattgtcataccaggTTTTTaggcataggacccgtgtct | 26 | mouse GAPDH |
| mGAP 2009 | gtccaccaccctgttgctgtaTTTTTaggcataggacccgtgtct | 27 | mouse GAPDH |
| mGAP 2010 | aattgtgagggagatgctcagtTTTTTaggcataggacccgtgtct | 28 | mouse GAPDH |
| mGAP 2011 | ccaccttcttgatgtcatcatactt | 29 | mouse GAPDH |
| mGAP 2012 | cccaagatgcccttcagtgg | 30 | mouse GAPDH |
| mGAP 2013 | gagacaacctggtcctcagtgtag | 31 | mouse GAPDH |
| mGAP 2014 | ggagttgctgttgaagtcgcag | 32 | mouse GAPDH |
| mGAP 2015 | ggcatcgaaggtggaagagtg | 33 | mouse GAPDH |
| mGAP 2016 | aaatgagcttgacaaagttgtcatt | 34 | mouse GAPDH |
| mGAP 2017 | gaggccatgtaggccatgag | 35 | mouse GAPDH |
| mGAP 2018 | gtccttgctggggtgggt | 36 | mouse GAPDH |
| mGAP 2019 | tagggcctctcttgctcagt | 37 | mouse GAPDH |
| mGAP 2020 | gttgggggccgagttggga | 39 | mouse GAPDH |
| mGAP 2021 | atgggggtctgggatgga | 39 | mouse GAPDH |
| mGAP 2022 | tattcaagagagtagggagggct | 40 | mouse GAPDH |
| mmFak7 001 | gagaagcagcagcccatgcTTITTctcttggaaagaaagt | 41 | mouse Factor VII |
| mmFak7 002 | tggagctggagcagaaagcaTTTTTctcttggaaagaaagt | 42 | mouse Factor VII |
| mmFak7 003 | tgcttcctcctgggttatgaaaTTTTTctcttggaaagaaagt | 43 | mouse Factor VII |
| mmFak7 004 | ccgggccaaagctcctccTTTTTctcttggaaagaaagt | 44 | mouse Factor VII |
| mmFak7 005 | cttgaagatctcccgggccTTTTTctcttggaaagaaagt | 45 | mouse Factor VII |
| mmFak7 006 | ctgcttggtcctctcagggctTTTTTctcttggaaagaaagt | 46 | mouse Factor VII |
| mmFak7 007 | actgcagtccctagaggtcccTTTTTaggcataggacccgtgtct | 47 | mouse Factor VII |
| mmFak7 008 | tttgcctgtgtaggacaccatgTTTTTaggcataggacccgtgtct | 48 | mouse Factor VII |
| mmFak7 009 | tcctcaaaggagcactgttccTTTTTaggcataggacccgtgtct | 49 | mouse Factor VII |
| mmFak7 010 | ccccatcactgtaaacaatccagaaTTTTTaggcataggacccgtgtct | 50 | mouse Factor VII |
| mmFak7 011 | tggattcgaggcacactggtTTTTTaggcataggacccgtgtct | 51 | mouse Factor VII |
| mmFak7 012 | tggcaggtacctacgttctgacaTTTTTaggcataggacccgtgtct | 52 | mouse Factor VII |
| mmFak7 013 | cttgcttttctcacagttccgaTTTTTaggcataggacccgtgtct | 53 | mouse Factor VII |
| mmFak7 014 | aggagtgagttggcacgcc | 54 | mouse Factor VII |
| mmFak7 015 | tcattgcactctctctccagagag | 55 | mouse Factor VII |
| mmFak7 016 | gcagacgtaagacttgagatgatcc | 56 | mouse Factor VII |
| mmFak7 017 | ccctcaaagtctaggaggcagaa | 57 | mouse Factor VII |
| mmFak7 018 | ttgcacagatcagctgctcatt | 58 | mouse Factor VII |
| EGFP 001 | ggcacgggcagcttgcTTTTTctcttggaaagaaagt | 59 | EGFP |
| EGFP 002 | ggtagcggctgaagcactgTTTTTctcttggaaagaaagt | 60 | EGFP |
| EGFP 003 | cctggacgtagccttcgggTTTTTctcttggaaagaaagt | 61 | EGFP |

TABLE 3-continued

Quantigene 1.0 probe sets.

| Oligo Name | Sequence 5' → 3' | SEQ ID No. | mRNA |
|---|---|---|---|
| EGFP 004 | ccttgaagaagatggtgcgctTTTTTctcttggaaagaaagt | 62 | EGFP |
| EGFP 005 | cgaacttcacctcggcgcTTTTTctcttggaaagaaagt | 63 | EGFP |
| EGFP 006 | ccttcagctcgatgcggtTTTTTctcttggaaagaaagt | 64 | EGFP |
| EGFP 007 | gtcacgagggtgggccagTTTTTaggcataggacccgtgtct | 65 | EGFP |
| EGFP 008 | cacgccgtaggtcagggtgTTTTTaggcataggacccgtgtct | 66 | EGFP |
| EGFP 009 | gtgctgcttcatgtggtcggTTTTTaggcataggacccgtgtct | 67 | EGFP |
| EGFP 010 | tcaccagggtgtcgccctTTTTTaggcataggacccgtgtct | 68 | EGFP |
| EGFP 011 | cggtggtgcagatgaacttca | 69 | EGFP |
| EGFP 012 | catggcggacttgaagaagtc | 70 | EGFP |
| EGFP 013 | cgtcctccttgaagtcgatgc | 71 | EGFP |
| mmClec4f 001 | ggtcccttctcagggtctgtaaTTTTTctcttggaaagaaagt | 72 | mouse Clec4f |
| mmClec4f 002 | tctgtcttggccctctgaagatTTTTTctcttggaaagaaagt | 73 | mouse Clec4f |
| mmClec4f 003 | ccccaggcgattctgctcTTTTTctcttggaaagaaagt | 74 | mouse Clec4f |
| mmClec4f 004 | tctgctcctgcttctgtgcagTTTTTctcttggaaaeaaagt | 75 | mouse Clec4f |
| mmClec4f 005 | cagaacttctcagcctcccgTTTTTctcttggaaagaaagt | 76 | mouse Clec4f |
| mmClec4f 006 | tgcgctccctgggacgtaTTTTTctcttggaaagaaagt | 77 | mouse Clec4f |
| mmClec4f 007 | gacttcaaagctgagacatcactcaTTTTTaggcataggacccgtgtct | 78 | mouse Clec4f |
| mmClec4f 008 | gatctgccttcaaactctgcatcTTTTTaggcataggacccgtgtct | 79 | mouse Clec4f |
| mmClec4f 009 | ggctttggtcgcctgcaTTTTTaggcataggacccgtgtct | 80 | mouse Clec4f |
| mmClec4f 010 | ttccagttctgcgcgatcaTTTTTaggcataggacccgtgtct | 81 | mouse Clec4f |
| mmClec4f 011 | agaggtcaccgaagccaggTTTTTaggcataggacccgtgtct | 82 | mouse Clec4f |
| mmClec4f 012 | tgctctgtagcatctggacattg | 83 | mouse Clec4f |
| mmClec4f 013 | cccctgaatcttggcagtgag | 84 | mouse Clec4f |
| mmClec4f 014 | ccacagcttcctgcagggc | 85 | mouse Clec4f |
| mmClec4f 015 | gctggagaacctgattctgagtct | 86 | mouse Clec4f |
| mmClec4f 016 | aaaagtaataaaagtttccattgaagtac | 87 | mouse Clec4f |
| mmClec4f 017 | ccacggcttcttgtcacgag | 88 | mouse Clec4f |
| mmReln 001 | cagagatcttgaactgcatgatccTTTTTctcttggaaagaaagt | 89 | mouse Reln |
| mmReln 002 | tcggcgggtaagcactgaTTTTTctcttggaaagaaagt | 90 | mouse Reln |
| mmReln 003 | cgcttccagaacactttgggTTTTTctcttggaaagaaagt | 91 | mouse Reln |
| mmReln 004 | ttcaggaagcgggtaggtgaTTTTTctcttggaaagaaagt | 92 | mouse Reln |
| mmReln 005 | gtccatcatggctgccacaTTTTTaggcataggacccgtgtct | 93 | mouse Reln |
| mmReln 006 | tcatgagtcactgcatacacctctcTTTTTaggcataggacccgtgtct | 94 | mouse Reln |
| mmReln 007 | ttcaggcactttgcatccaaTTTTTaggcataggacccgtgtct | 95 | mouse Reln |
| mmReln 008 | tgaatttgattctgggcaattttTTTTTaggcataggacccgtgtct | 96 | mouse Reln |
| mmReln 009 | gggactaaataactccagctcacgTTTTTaggcataggacccgtgtct | 97 | mouse Reln |
| mmReln 010 | tccttttccacccttcagttgTTTTTaggcataggacccgtgtct | 98 | mouse Reln |
| mmReln 011 | ttacaggattccccgttaagctTTTTTaggcataggacccgtgtct | 99 | mouse Reln |

TABLE 3-continued

Quantigene 1.0 probe sets.

| Oligo Name | Sequence 5' → 3' | SEQ ID No. | mRNA |
|---|---|---|---|
| mmReln 012 | gggtcacagatacactgttcctttTTTTTaggcataggacccgtgtct | 100 | mouse Reln |
| mmReln 013 | agtcacagaatctttccactgtacag | 101 | mouse Reln |
| mmReln 014 | gagcatgacaccatctggcg | 102 | mouse Reln |
| mmReln 015 | agttctcagtgggcgtcagg | 103 | mouse Reln |
| mmReln 016 | ccaaagtcagtagaaaactgcacg | 104 | mouse Reln |
| mmReln 017 | ggaagaacacagacggttgagaaa | 105 | mouse Reln |
| mmReln 018 | tctgagtacttttggtagaacctaaatc | 106 | mouse Reln |
| mmTek 001 | tgagtccctgggaagcttTcaTTTTTctcttggaaagaaagt | 107 | mouse Tek |
| mmTek 002 | acttccccagatctccccatTTTTTctcttggaaagaaagt | 108 | mouse Tek |
| mmTek 003 | taagccggctaaagagtccatTTTTTctcttggaaagaaagt | 109 | mouse Tek |
| mmTek 004 | aatgcaggtgagggatgtttTTTTTctcttggaaagaaagt | 110 | mouse Tek |
| mmTek 005 | tcctatggtgatgggctcatggTTTTTctcttggaaagaaagt | 111 | mouse Tek |
| mmTek 006 | ccgctcgcatggtccacgTTTTTaggcataggacccgtgtct | 112 | mouse Tek |
| mmTek 007 | acaactcacaactttgcgacttcTTTTTaggcataggacccgtgtct | 113 | mouse Tek |
| mmTek 008 | ccagcgtccacagatgagcaTTTTTaggcataggacccgtgtct | 114 | mouse Tek |
| mmTek 009 | agcaagctgactccacagagaacTTTTTaggcataggacccgtgtct | 115 | mouse Tek |
| mmTek 010 | gcgccttctactactccataaaggTTTTTaggcataggacccgtgtct | 116 | mouse Tek |
| mmTek 011 | cggcatcagacacaagaggtaggTTTTTaggcataggacccgtgtct | 117 | mouse Tek |
| mmTek 012 | gggtgccacccagaggcTTTTTaggcataggacccgtgtct | 118 | mouse Tek |
| mmTek 013 | gcaaggagaaacaccacagaag | 119 | mouse Tek |
| mmTek 014 | cgctcttgtttacaagttggcg | 120 | mouse Tek |
| mmTek 015 | gaattgatcaagatcaggtccatg | 121 | mouse Tek |

TABLE 4

Quantigene 2.0 probe sets.

| Oligo Name | Sequence 5' → 3' | SEQ ID No. | mRNA |
|---|---|---|---|
| Q2 mCD45 1 | tgacgagttttacaccgcgatTTTTTgaagttaccgtttt | 122 | mouse CD45 |
| Q2 mCD45 2 | aatctgtctgcacatttataacattttTTTTTctgagtcaaagcat | 123 | mouse CD45 |
| Q2 mCD45 3 | ggcgtttctggaaatccccaTTTTTctcttggaaagaaagt | 124 | mouse CD45 |
| Q2 mCD45 4 | tggatccccacaactaggcttaTTTTTgaagttaccgtttt | 125 | mouse CD45 |
| Q2 mCD45 5 | agagactaacgttttcttgcagcTTTTTctgagtcaaagcat | 126 | mouse CD45 |
| Q2 mCD45 6 | gtttagatacaggctcaggccaTTTTTctcttggaaagaaagt | 127 | mouse CD45 |
| Q2 mCD45 7 | tggggtttagatgcagactcagTTTTTgaagttaccgtttt | 128 | mouse CD45 |
| Q2 mCD45 8 | attgttcttatagcataaaacatatccaTTTTTctgagtcaaagcat | 129 | mouse CD45 |
| Q2 mCD45 9 | taggcaaacttttacatttttctgaTTTTTctcttggaaagaaagt | 130 | mouse CD45 |
| Q2 mCD45 10 | ccacctcaaaactggtcacattatTTTTTgaagttaccgtttt | 131 | mouse CD45 |

TABLE 4-continued

Quantigene 2.0 probe sets.

| Oligo Name | Sequence 5' → 3' | SEQ ID No. | mRNA |
|---|---|---|---|
| Q2 mCD45 11 | tcatagtatttataaggtttcaagctttTTTTTctgagtcaaagcat | 132 | mouse CD45 |
| Q2 mCD45 12 | ttgacataggcaagtagggacact | 133 | mouse CD45 |
| Q2 mCD45 13 | cccatttctttgaatcttcccaTTTTTctcttggaaagaaagt | 134 | mouse CD45 |
| Q2 mCD45 14 | tgaaaattgcacttctcagcagtTTTTTgaagttaccgtttt | 135 | mouse CD45 |
| Q2 mCD45 15 | ccggacgatctgcttttgtgTTTTTctgagtcaaagcat | 136 | mouse CD45 |
| Q2 mCD45 16 | ggttttcattccattgaccttgtTTTTTctcttggaaagaaagt | 137 | mouse CD45 |
| Q2 mCD45 17 | ttgtctgtcggccgggaTTTTTgaagttaccgtttt | 138 | mouse CD45 |
| Q2 mCD45 18 | ggaggaccacatgtaacatttatactaTTTTTctgagtcaaagcat | 139 | mouse CD45 |
| Q2 mCD45 19 | ggttttagggccattagtttcataaTTTTTctcttggaaagaaagt | 140 | mouse CD45 |
| mGAPDH QG2 1 | cgaggctggcactgcacaaTTTTTctcttggaaagaaagt | 141 | mouse GAPDH |
| mGAPDH QG2 2 | cttcaccattttgtctacgggaTTTTTgaagttaccgtttt | 142 | mouse GAPDH |
| mGAPDH QG2 3 | ccaaatccgttcacaccgacTTTTTctgagtcaaagcat | 143 | mouse GAPDH |
| mGAPDH QG2 4 | ccaggcgcccaatacggTTTTTctcttggaaagaaagt | 144 | mouse GAPDH |
| mGAPDH QG2 5 | caatggcagccctggtgaTTTTTgaagttaccgtttt | 145 | mouse GAPDH |
| mGAPDH QG2 6 | aacaatctccactttgccactgTTTTTctgagtcaaagcat | 146 | mouse GAPDH |
| mGAPDH QG2 7 | tgaaggggtcgttgatggc | 147 | mouse GAPDH |
| mGAPDH QG2 8 | catgtagaccatgtagttgaggtcaa | 148 | mouse GAPDH |
| mGAPDH QG2 9 | ccgtgagtggagtcatactggaaTTTTTctcttggaaagaaagt | 149 | mouse GAPDH |
| mGAPDH QG2 10 | ttgactgtgccgttgaatttgTTTTTctcttggaaagaaagt | 150 | mouse GAPDH |
| mGAPDH QG2 11 | agcttcccattctcggccTTTTTgaagttaccgtttt | 151 | mouse GAPDH |
| mGAPDH QG2 12 | gggcttcccgttgatgacaTTTTTctgagtcaaagcat | 152 | mouse GAPDH |
| mGAPDH QG2 13 | cgctcctggaagatggtgatTTTTTctcttggaaagaaagt | 153 | mouse GAPDH |
| mGAPDH QG2 14 | cccatttgatagttagtggggtct | 154 | mouse GAPDH |
| mGAPDH QG2 15 | atactcagcaccggcctcacTTTTTctcttggaaagaaagt | 155 | mouse GAPDH |
| QG2 mCD68 1 | ctgggagccgttggccTTTTTctcttggaaagaaagt | 156 | mouse CD68 |
| QG2 mCD68 2 | ggcttggagctgaacacaaggTTTTTgaagttaccgtttt | 157 | mouse CD68 |
| QG2 mCD68 3 | ggtataggattcggatttgaatttgTTTTTctgagtcaaagcat | 158 | mouse CD68 |
| QG2 mCD68 4 | acctttcttccaccctgaattgTTTTTctcttggaaagaaagt | 159 | mouse CD68 |
| QG2 mCD68 5 | tctttaagccccactttagctttTTTTTgaagttaccgtttt | 160 | mouse CD68 |
| QG2 mCD68 6 | acagatatgccccaagcccTTTTTctgagtcaaagcat | 161 | mouse CD68 |
| QG2 mCD68 7 | cttggttttgttgggattcaaaTTTTTgaagttaccgtttt | 162 | mouse CD68 |
| QG2 mCD68 8 | ccgtcacaacctccctggacTTTTTctgagtcaaagcat | 163 | mouse CD68 |
| QG2 mCD68 9 | agagacaggtggggatgggtaTTTTTctcttggaaagaaagt | 164 | mouse CD68 |
| QG2 mCD68 10 | ggtaagctgtccataaggaaatgagTTTTTgaagttaccgtttt | 165 | mouse CD68 |
| QG2 mCD68 11 | tgtaggtcctgtttgaatcaaaTTTTTctgagtcaaagcat | 166 | mouse CD68 |
| QG2 mCD68 12 | ggtagactgtactcgggctctgaTTTTTctcttggaaagaaagt | 167 | mouse CD68 |
| QG2 mCD68 13 | tccaccgccatgtagtccaTTTTTgaagttaccgtttt | 168 | mouse CD68 |
| QG2 mCD68 14 | cctgtgggaaggacacattgtatTTTTTctgagtcaaagcat | 169 | mouse CD68 |

TABLE 4-continued

Quantigene 2.0 probe sets.

| Oligo Name | Sequence 5' → 3' | SEQ ID No. | mRNA |
|---|---|---|---|
| QG2 mCD68 15 | ccatgaatgtccactgtgctgTTTTTgaagttaccgtttt | 170 | mouse CD68 |
| QG2 mCD68 16 | tctcgaagagatgaattctgcgTTTTTctgagtcaaagcat | 171 | mouse CD68 |
| QG2 mCD68 17 | cccaagggagcttggagcTTTTTctcttggaaagaaagt | 172 | mouse CD68 |
| QG2 mCD68 18 | tttccacagcagaagctttgg | 173 | mouse CD68 |
| QG2 mCD68 19 | ctggagaaagaactatgcttgca | 174 | mouse CD68 |
| QG2 mCD68 20 | agagagcaggtcaaggtgaacagTTTTTctcttggaaagaaagt | 175 | mouse CD68 |
| QG2 eGFP 1 | ggctgaagcactgcacgcTTTTgaagttaccgtttt | 176 | EGFP |
| QG2 eGFP 2 | gaagtcgatgcccttcagctTTTTTctgagtcaaa.e;cat | 177 | EGFP |
| QG2 eGFP 3 | ggatgttgccgtcctccttTTTTTgaagttaccgtttt | 178 | EGFP |
| QG2 eGFP 4 | tactccagcttgtgccccaTTTTTctgagtcaaagcat | 179 | EGFP |
| QG2 eGFP 5 | agacgttgtggctgttgtagttgTTTTTgaagttaccgtttt | 180 | EGFP |
| QG2 eGFP 6 | tctgcttgtcggccatgatatTTTTTctgagtcaaagcat | 181 | EGFP |
| QG2 eGFP 7 | aagttcaccttgatgccgttctTTTTTgaagttaccgtttt | 182 | EGFP |
| QG2 eGFP 8 | cgatgttgtggcggatcttgTTTTTctgagtcaaagcat | 183 | EGFP |
| QG2 eGFP 9 | ctgcacgctgccgtcctTTTTctcttggaaagaaagt | 184 | EGFP |
| QG2 eGFP 10 | gctggtagtggtcggcgag | 185 | EGFP |
| QG2 eGFP 11 | cgccgatggggtgttct | 186 | EGFP |
| QG2 eGFP 12 | cttcatgtggtcggggtagcTTTTTctgagtcaaagcat | 187 | EGFP |
| QG2 eGFP 13 | gcagcacggggccgt | 188 | EGFP |
| QG2 eGFP 14 | caggtagtggttgtcgggca | 189 | EGFP |
| QG2 eGFP 15 | agggcggactgggtgctTTTTctcttggaaagaaagt | 190 | EGFP |
| QG2 eGFP 16 | tctcgttggggtctttgctc | 191 | EGFP |
| QG2 eGFP 17 | aggaccatgtgatcgcgctTTTTTctcttggaaagaaagt | 192 | EGFP |
| QG2 eGFP 18 | gcggtcacgaactccagcTTTTTctcttggaaagaaagt | 193 | EGFP |
| QG2 eGFP 19 | cggacttgaagaagtcgtgctg | 194 | EGFP |
| QG2 eGFP 20 | cgtagccttcgggcatggTTTTTctcttggaaagaaagt | 195 | EGFP |
| QG2 eGFP 21 | aagatggtgcgctcctggaTTTTTgaagttaccgtttt | 196 | EGFP |
| QG2 eGFP 22 | agttgccgtcgtccttgaagTTTTTctgagtcaaagcat | 197 | EGFP |
| QG2 eGFP 23 | tcggcgcgggtcttgt | 198 | EGFP |
| QG2 eGFP 24 | gtcgccctcgaacttcaccTTTTTctcttggaaagaaagt | 199 | EGFP |
| QG2 eGFP 25 | cgatgcggttcaccagggtTTTTTgaagttaccgtttt | 200 | EGFP |
| QG2 mClec7a 1 | tttctctgatccccctgggcTTTTTgaagttaccgtttt | 201 | mouse Clec7a |
| QG2 mClec7a 2 | gaagatggagcctggcttccTTTTTctgagtcaaagcat | 202 | mouse Clec7a |
| QG2 mClec7a 3 | gcaatgggcctccaaggtTTTTTctcttggaaagaaagt | 203 | mouse Clec7a |
| QG2 mClec7a 4 | gcacaggattcctaaacccactTTTTTgaagttaccgtttt | 204 | mouse Clec7a |
| QG2 mClec7a 5 | gcagcaaccactactaccacaaaTTTTTctgagtcaaagcat | 205 | mouse Clec7a |
| QG2 mClec7a 6 | tgctagggcacccagcactTTTTTctcttggaaagaaagt | 206 | mouse Clec7a |

TABLE 4-continued

Quantigene 2.0 probe sets.

| Oligo Name | Sequence 5' → 3' | SEQ ID No. | mRNA |
|---|---|---|---|
| QG2 mClec7a 7 | cctgaattgtgtcgccaaaaTTTTgaagttaccgtttt | 207 | mouse Clec7a |
| QG2 mClec7a 8 | ttgtctttctcctctggatttctcTTTTTctgagtcaaagcat | 208 | mouse Clec7a |
| QG2 mClec7a 9 | tggttctctttatttcttgataggaagTTTTTctcttggaaagaaagt | 209 | mouse Clec7a |
| QG2 mClec7a 10 | ctaaagatgattctgtgggcttgTTTTTgaagttaccgtttt | 210 | mouse Clec7a |
| QG2 mClec7a 11 | ggagggagccaccttctcatTTTTTctgagtcaaagcat | 211 | mouse Clec7a |
| QG2 mClec7a 12 | ctcctgtagtttgggatgccttTTTTTctcttggaaagaaagt | 212 | mouse Clec7a |
| QG2 mClec7a 13 | ggaaggcaaggctgagaaaaacTTTTTgaagttaccgtttt | 213 | mouse Clec7a |
| QG2 mClec7a 14 | cttccatgcatgatccaattaTTTTTctgagtcaaagcat | 214 | mouse Clec7a |
| QG2 mClec7a 15 | cctgagaagctaaataggtaacagctTTTTTctcttggaaagaaagt | 215 | mouse Clec7a |
| QG2 mClec7a 16 | tctcttacttccataccaggaatttTTTTTgaagttaccgtttt | 216 | mouse Clec7a |
| QG2 mClec7a 17 | gcacctagctgggagcagtgTTTTTctgagtcaaagcat | 217 | mouse Clec7a |
| QG2 mClec7a 18 | ttttgagttgtctatcttcagtagatga | 218 | mouse Clec7a |
| QG2 mClec7a 19 | tggctttcaatgaactcaaattcTTTTTctcttggaaagaaagt | 219 | mouse Clec7a |
| QG2 mClec7a 20 | gcattaatacggtgagacgatgttTTTTTgaagttaccgtttt | 220 | mouse Clec7a |
| QG2 mClec7a 21 | cgggaaaggcctatccaaaatTTTTTctgagtcaaagcat | 221 | mouse Clec7a |
| QG2 mClec7a 22 | catggcccttcactctgattgTTTTTctcttggaaagaagt | 222 | mouse Clec7a |
| QG2 mClec7a 23 | gctgatccatcctcccagaacTTTTTctcttggaaagaaagt | 223 | mouse Clec7a |
| QG2 mClec7a 24 | ttgaaacgattggggaagaatTTTTTctcttggaaagaaagt | 224 | mouse Clec7a |
| QG2 mClec7a 25 | cctggggagctgtatttctgacTTTTTgaagttaccgtttt | 225 | mouse Clec7a |
| QG2 mClec7a 26 | catacacaattgtgcagtaagctttTTTTTctgagtcaaagcat | 226 | mouse Clec7a |

The bDNA assay was performed using 20 μL lysate and the corresponding gene specific probe sets. For normalization purposes GAPDH mRNA expression was analyzed using 40 μL lysate and *Rattus norvegicus* probe sets shown to be cross-react with mice (sequences of probe sets see above). As assay readout the chemiluminescence signal was measured in a Victor 2 Light luminescence counter (Perkin Elmer, Wiesbaden, Germany) as relative light units (RLU). The signal for the corresponding mRNA was divided by the signal for GAPDH mRNA from the same lysate. Values are reported as mRNA expression normalized to GAPDH.

For measurement of FVII activity, plasma samples from mice were prepared by collecting blood (9 volumes) by submandibular bleeding into microcentrifuge tubes containing 0.109 mol/L sodium citrate anticoagulant (1 volume) following standard procedures. FVII activity in plasma was measured with a chromogenic method using a BIOPHEN VII kit (Hyphen BioMed/Aniara, Mason, Ohio) following manufacturers recommendations. Absorbance of colorimetric development was measured using a Tecan Safire2 microplate reader (Tecan, Crailsheim, Germany) at 405 nm. Results are shown in FIGS. 2-17.

TABLE 5

Composition and physico-chemical parameters of the benchmark formulation RLX-165 and the LNP RLK-044 containing lipid KL22 of the present invention. The benchmark formulation was prepared according to a published protocol (*Nature Biotechnology* 2010, 28:172) with the exception of a slightly different PEG-lipid. Instead of PEG2000-c-DMA (methoxypolyethyleneglycol-carbamoyl-dimyristyloxy-propylamine), PEG2000-c-DMOG (α-[3'-(1,2-dimyristoyl-3-propanoxy )-carboxamide-propyl ]-ω-methoxy-polyoxyethylene) was used.

| LNP | Amino-lipid mol % | | Helper lipid mol % | | Chol mol % | PEG2000-lipid mol % | | N/P | Size (nm) | Encap % |
|---|---|---|---|---|---|---|---|---|---|---|
| RLX-165 | 57.1 | XTC2 | 7.1 | DPPC | 34.4 | 1.4 | DMOG | 2.2 | 92 | 92 |
| RLK-044 | 50 | KL22 | 10 | DSPC | 38.5 | 1.5 | DMOG | 7.6 | 92 | 80 |

TABLE 6

LNPs based on the amino-lipid KL10. Compositions, physico-chemical properties and serum FVII activity upon treatment with 0.1 mg/kg siRNA directed against FVII.

| No | KL10 mol % | DSPC mol % | Chol mol % | PEG2000-c-DOMG mol % | N/P | Size (nm) | Encap (%) | FVII (%) |
|---|---|---|---|---|---|---|---|---|
| 1 | 50 | 10 | 38.5 | 1.5 | 4.9 | 106 | 74 | 81 |
| 2 | 50 | 10 | 38.5 | 1.5 | 6.9 | 108 | 78 | 55 |
| 3 | 60 | 0 | 38.5 | 1.5 | 5.9 | 79 | 36 | 54 |
| 4 | 50 | 10% C16 Diether PC | 38.5 | 1.5 | 5.9 | 110 | 84 | 69 |
| 5 | 50 | 10 | 38.5 | 1.5 | 8.4 | 80 | 83 | 23 |
| 6 | 65 | 3.5 | 30 | 1.5 | 6.9 | 83 | 56 | 107 |
| 7 | 60 | 8.5 | 30 | 1.5 | 6.9 | 93 | 71 | 52 |
| 8 | 50 | 9.5 | 30 | 0.5 | 6.9 | 121 | 75 | 60 |
| 9 | 60 | 0 | 30 | 10 | 6.9 | 49 | 36 | 84 |
| 10 | 65 | 0 | 30 | 5 | 6.9 | 64 | 29 | 129 |
| 11 | 98.5 | 0 | 0 | 1.5 | 6.9 | 122 | 53 | 110 |
| 12 | 50 | 10% DMPC | 38.5 | 1.5 | 6.9 | 99 | 79 | 78 |
| 13 | 50 | 10% DPPC | 38.5 | 1.5 | 6.9 | 100 | 81 | 43 |
| 14 | 50 | 10% DOPC | 38.5 | 1.5 | 6.9 | 90 | 75 | 122 |
| 15 | 50 | 10% DUPC | 38.5 | 1.5 | 6.9 | 89 | 74 | 128 |
| 16 | 50 | 10% POPC | 38.5 | 1.5 | 6.9 | 86 | 76 | 128 |
| 17 | 50 | 10% C18 Diether PC | 38.5 | 1.5 | 6.9 | 96 | 86 | 46 |
| 18 | 50 | 10% C16 Lyso-PC | 38.5 | 1.5 | 6.9 | 91 | 75 | 77 |
| 19 | 50 | 10% DOPE | 38.5 | 1.5 | 6.9 | 88 | 69 | 124 |
| 20 | 50 | 10% DOPG | 38.5 | 1.5 | 6.9 | 92 | 39 | 77 |
| 21 | 50 | 10% SM | 38.5 | 1.5 | 6.9 | 101 | 90 | 27 |
| 22 | 50 | 10 | 38.5% OChemsPC | 1.5 | 6.9 | 75 | 89 | 140 |
| 23 | 50 | 10 | 38.5% DOPE | 1.5 | 6.9 | 99 | 89 | 153 |
| 24 | 50 | 10 | 38.5 | 1.5% mPEG-1000 DM | 6.9 | 129 | 88 | 97 |
| 25 | 50 | 10 | 38.5 | 1.5% mPEG-2000 DS | 6.9 | 120 | 88 | 108 |
| 26 | 50 | 10 | 38.5 | 1.5% PEG-2000 Chol | 6.9 | 109 | 88 | 91 |
| 29 | 50 | 0 | 48.5% 4ME16:0PE | 1.5 | 6.9 | 111 | 86 | 81 |
| XTC2 | 57.1 | 7.1% DPPC | 34.4 | 1.4 | 2.2 | 95 | 92 | 65 |

TABLE 7

LNPs based on the amino-lipid KL22. Compositions, physico-chemical properties and serum FVII activity upon treatment with 0.1 mg/kg siRNA directed against FVII.

| No | KL22 mol % | DSPC mol % | Chol mol % | PEG2000-c-DOMG mol % | N/P | Size (nm) | Encap % | FVII % |
|---|---|---|---|---|---|---|---|---|
| 1 | 50 | 10 | 38.5 | 1.5 | 5.5 | 78 | 46 | 68 |
| 2 | 50 | 10 | 38.5 | 1.5 | 10 | 76 | 63 | 45 |
| 3 | 50 | 10 | 38.5 | 1.5 | 15 | 81 | 69 | 61 |
| 4 | 50 | 10 | 39.5 | 0.5 | 7.6 | 126 | 84 | 64 |
| 5 | 50 | 10 | 40 | 0 | 7.6 | 736 | 40 | 78 |
| 6 | 50 | 20 | 30 | 0 | 7.6 | 414 | 9 | nd |
| 7 | 60 | 0 | 38.5 | 1.5 | 7.6 | 84 | 28 | nd |
| 8 | 60 | 8.5 | 30 | 1.5 | 7.6 | 92 | 36 | 80 |
| 9 | 40 | 20 | 38.5 | 1.5 | 7.6 | 93 | 82 | 79 |
| 10 | 65 | 0 | 30 | 5 | 7.6 | 59 | 5 | nd |
| 11 | 98.5 | 0 | 0 | 1.5 | 7.6 | 95 | 0 | nd |
| 12 | 50 | 10% DMPC | 38.5 | 1.5 | 7.6 | 78 | 57 | 92 |
| 13 | 50 | 10% DPPC | 38.5 | 1.5 | 7.6 | 90 | 47 | 73 |
| 14 | 50 | 10% DOPC | 38.5 | 1.5 | 7.6 | 71 | 62 | 57 |
| 15 | 50 | 10% DUPC | 38.5 | 1.5 | 7.6 | 84 | 59 | 63 |
| 16 | 50 | 10% POPC | 38.5 | 1.5 | 7.6 | 74 | 55 | 81 |
| 17 | 50 | 10% C18 Diether PC | 38.5 | 1.5 | 7.6 | 96 | 61 | 103 |
| 18 | 50 | 10% C16 Lyso-PC | 38.5 | 1.5 | 7.6 | 75 | 38 | 75 |
| 19 | 50 | 10% DOPE | 38.5 | 1.5 | 7.6 | 75 | 49 | 59 |
| 20 | 50 | 10% DOPG | 38.5 | 1.5 | 7.6 | 80 | 48 | 131 |
| 21 | 50 | 10% SM | 38.5 | 1.5 | 7.6 | 92 | 64 | 68 |
| 22 | 50 | 10 | 38.5% | 1.5 | 7.6 | 76 | 84 | 107 |

TABLE 7-continued

LNPs based on the amino-lipid KL22. Compositions, physico-chemical properties and serum FVII activity upon treatment with 0.1 mg/kg siRNA directed against FVII.

| No | KL22 mol % | DSPC mol % | Chol mol % | PEG2000-c-DOMG mol % | N/P | Size (nm) | Encap % | FVII % |
|---|---|---|---|---|---|---|---|---|
| 23 | 50 | 10 | OChemsPC 38.5% DOPE | 1.5 | 7.6 | 93 | 75 | 127 |
| 24 | 50 | 10 | 38.5% DSPC | 1.5 | 7.6 | 246 | 1 | nd |
| 25 | 50 | 10 | 38.5 | 1.5% mPEG-1000 DM | 7.6 | 122 | 86 | 112 |
| 26 | 50 | 10 | 38.5 | 1.5% mPEG-5000 DM | 7.6 | 91 | 36 | nd |
| 27 | 50 | 10 | 38.5 | 1.5% mPEG-1000 DS | 7.5 | 119 | 86 | 106 |
| 28 | 50 | 10 | 38.5 | 1.5% mPEG-2000 DS | 7.6 | 106 | 68 | 107 |
| 29 | 50 | 10 | 38.5 | 1.5% PEG-1000 Chol | 7.6 | 147 | 90 | 110 |
| 30 | 50 | 10 | 38.5 | 1.5 % PEG 2000 Chol | 7.6 | 101 | 64 | 134 |
| XTC2 | 57.1 | 7.1% OPPC | 34.4 | 1.4 | 2.2 | 95 | 92 | 44 |

TABLE 8

LNPs based on the amino-lipid KL25. Compositions, physico-chemical properties and FVII mRNA levels upon treatment with 0.1 mg/kg siRNA directed against FVII

| No | KL25 mol % | DSPC mol % | Cholesterol mol % | PEG2000c-DOMG mol % | N/P | Size (nm) | Encap % | FVII % |
|---|---|---|---|---|---|---|---|---|
| Std | 50 | 10 | 38.5 | 1.5 | 6.7 | 142 | 90 | 81 |
| 1 | 50 | 10 | 38.5% DOPE | 1.5 | 6.7 | nd | — | nd |
| 2 | 50 | 10 | 40 | 0 | 6.7 | nd | — | nd |
| 3 | 50 | 10 | 38.5 | 1.5 | 5 | 109 | 31 | nd |
| 4 | 50 | 10 | 38.5 | 1.5 | 10 | 128 | 68 | 35 |
| 5 | 50 | 10 | 38.5 | 1.5 | 15 | 120 | 72 | 34 |
| 6 | 40 | 20 | 38.5 | 1.5 | 6.7 | 111 | 47 | 39 |
| 7 | 60 | 0 | 38.5 | 1.5 | 6.7 | 113 | 34 | 40 |
| 8 | 50 | 10% C16 Diether PC | 38.5 | 1.5 | 6.7 | 132 | 65 | 67 |
| 9 | 50 | 10% SM | 38.5 | 1.5 | 6.7 | 123 | 58 | 51 |
| 10 | 50 | 10 | 38.5 | 1.5% mPEG-1000 DM | 6.7 | 177 | 59 | 47 |
| 11 | 50 | 10 | 38.5 | 1.5% mPEG-1000 DS | 6.7 | 122 | 80 | 50 |
| 12 | 50 | 10 | 38.5 | 1.5% mPEG-2000 DS | 6.7 | 123 | 49 | 74 |
| 13 | 50 | 10 | 38.5 | 1.5% PEG-1000 Chol | 6.7 | 207 | 9 | nd |
| 14 | 50 | 10 | 38.5 | 1.5% PEG-2000 Chol | 6.7 | 141 | 46 | 68 |

TABLE 9

LNPs based on the amino-lipid KL25. Compositions and physico-chemical properties.

| No | KL25 mol % | DSPC mol % | Chol mol % | PEG2000-c-DOMG mol % | N/P | Size (nm) | Encap % |
|---|---|---|---|---|---|---|---|
| std | 50 | 10 | 38.5 | 1.5 | 6.7 | 142 | 90 |
| 1 | 50 | 10 | 38.5% DOPE | 1.5 | 6.7 | nd | — |
| 2 | 50 | 10 | 40 | 0 | 6.7 | nd | — |
| 3 | 50 | 10 | 38.5 | 1.5 | 5 | 109 | 31 |
| 4 | 50 | 10 | 38.5 | 1.5 | 10 | 128 | 68 |
| 5 | 50 | 10 | 38.5 | 1.5 | 15 | 120 | 72 |
| 6 | 40 | 20 | 38.5 | 1.5 | 6.7 | 111 | 47 |
| 7 | 60 | 0 | 38.5 | 1.5 | 6.7 | 113 | 34 |
| 8 | 50 | 10% C16 Diether PC | 38.5 | 1.5 | 6.7 | 132 | 65 |
| 9 | 50 | 10% SM | 38.5 | 1.5 | 6.7 | 123 | 58 |
| 10 | 50 | 10 | 38.5 | 1.5% mPEG-1000 DM | 6.7 | 177 | 59 |
| 11 | 50 | 10 | 38.5 | 1.5% mPEG-1000 DS | 6.7 | 122 | 80 |

TABLE 9-continued

LNPs based on the amino-lipid KL25. Compositions and physico-chemical properties.

| No | KL25 mol % | DSPC mol % | Chol mol % | PEG2000-c-DOMG mol % | N/P | Size (nm) | Encap % |
|---|---|---|---|---|---|---|---|
| 12 | 50 | 10 | 38.5 | 1.5 % mPEG-2000 DS | 6.7 | 123 | 49 |
| 13 | 50 | 10 | 38.5 | 1.5% PEG-1000 Chol | 6.7 | 207 | 9 |
| 14 | 50 | 10 | 38.5 | 1.5% PEG-2000 Chol | 6.7 | 141 | 46 |

TABLE 10

Tek mRNA levels in various organs upon treatment with LNPs based on amino-lipid KL25. LNPs contained a pool of 5 siRNA of which one was directed against Tek (0.2 mg/kg of each siRNA, total siRNA dose 1 mg/kg). Values are given as the mean of two treated animals relative to saline treated animals.

| No | Kidney % Tek | Lung % Tek | Jejunum % Tek | Spleen % Tek | Muscle % Tek |
|---|---|---|---|---|---|
| std | 41 | 43 | 72 | 47 | 77 |
| 3 | 20 | 21 | 25 | 31 | 34 |
| 4 | 18 | 17 | 27 | 25 | 38 |
| 5 | 35 | 35 | 58 | 32 | 40 |
| 6 | 22 | 18 | 41 | 28 | 25 |
| 7 | 38 | 33 | 57 | 31 | 48 |
| 8 | 42 | 43 | 47 | 40 | 65 |
| 9 | 51 | 48 | 39 | 32 | 43 |
| 10 | 40 | 42 | 26 | 27 | 47 |
| 11 | 45 | 37 | 67 | 60 | 88 |
| 12 | 54 | 49 | 60 | 62 | 56 |
| 13 | 54 | 64 | 47 | 48 | 73 |
| 14 | 53 | 52 | 54 | 51 | 68 |
| saline | 100 | 100 | 100 | 100 | 100 |

TABLE 11 mRNA levels in liver after treatment with LNPs based on amino-lipid KL25. LNPs contained a pool of 5 siRNAs directed against the targets listed in the table (0.2 mg/kg of each siRNA, total siRNA dose 1 mg/kg). Values are given as the mean of two treated animals relative to saline treated animals.

| No | % FVII | % Clec4f | % Rein | % Tek | % GFP |
|---|---|---|---|---|---|
| Std | 81 | 51 | 32 | 51 | 80 |
| 3 | 35 | 29 | 28 | 57 | 61 |
| 4 | 34 | 29 | 23 | 60 | 58 |
| 5 | 39 | 31 | 51 | 91 | 75 |
| 6 | 40 | 27 | 58 | 66 | 72 |
| 7 | 67 | 44 | 41 | 64 | 80 |
| 8 | 51 | 36 | 40 | 59 | 84 |
| 9 | 47 | 36 | 57 | 58 | 74 |
| 10 | 50 | 33 | 30 | 61 | 80 |
| 11 | 74 | 46 | 43 | 65 | 82 |
| 12 | 68 | 59 | 55 | 66 | 89 |
| 13 | 65 | 63 | 55 | 59 | 72 |
| 14 | 55 | 42 | 17 | 67 | 70 |
| saline | 100 | 100 | 100 | 100 | 100 |

TABLE 12

Composition and physico-chemical properties of selected LNPs based on amino-lipid KL10

| No | KL10 mol % | DSPC mol % | Chol mol % | PEG2000-c-DOMG mol % | N/P | Size (nm) | Encap % |
|---|---|---|---|---|---|---|---|
| 21 | 50 | 10% SM | 38.5 | 1.5 | 6.9 | 92 | 64 |
| 23 | 50 | 10 | 38.5 DOPE | 1.5 | 6.9 | 93 | 75 |
| 29 | 50 | 0 | 48.5% 4ME16:0PE | 1.5 | 6.9 | 111 | 86 |

TABLE 13 mRNA levels of targets expressed in the liver upon treatment with LNPs based on amino-lipid KL10. LNPs contained a pool of 5 siRNA directed against the targets, in the table below (0.5 mg/kg of each siRNA).

| LNP | Animal | Rein | GFP | Tek | Clec4f | FVII |
|---|---|---|---|---|---|---|
| KL 10-21 | K1 | 13% | 82% | 25% | 19% | 102% |
|  | K2 | 15% | 104% | 30% | 13% | 106% |
| KL 10-23 | L1 | 17% | 10% | 46% | 136% | 28% |
|  | L2 | 14% | 8% | 35% | 113% | 22% |
| KL 10-29 | H1 | 12% | 77% | 33% | 5% | 88% |
|  | H2 | 13% | 65% | 33% | 12% | 86% |
| Saline | S1 | 95% | 101% | 100% | 97% | 101% |
|  | S2 | 105% | 99% | 100% | 103% | 99% |

What is claimed is:

1. A cyclic amino-lipid of the formula:

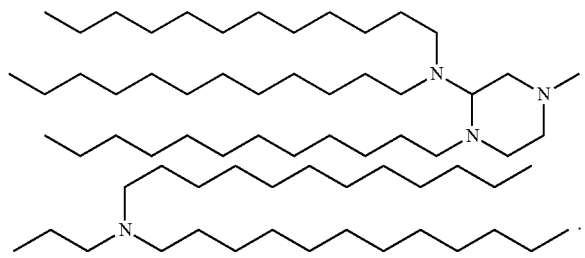

2. A lipid nanoparticle comprising a cyclic amino-lipid of claim 1.

3. The lipid nanoparticle of claim 2, further comprising an additional lipid selected from the group consisting of: cationic lipid, helper lipid, and PEG-lipid.

4. The lipid nanoparticle of claim 2, further comprising a hydrophobic small molecule.

5. The lipid nanoparticle of claim 2, further comprising a biologically active compound.

6. The lipid nanoparticle of claim 5, wherein the biologically active compound is selected from the group consisting of: a small molecule, a peptide, a protein, a carbohydrate, a nucleic acid; and a lipid.

7. The lipid nanoparticle of claim 3, wherein the cationic lipid is a lipid comprising a quaternary amine with a nitrogen atom having four organic substituents.

8. The lipid nanoparticle of claim 3, wherein the helper lipid is a neutral zwitterionic lipid.

9. The lipid nanoparticle of claim 4, wherein the hydrophobic small molecule is selected from the group consisting of a sterol and a hydrophobic vitamin.

10. The lipid nanoparticle of claim 9, wherein the hydrophobic small molecule is cholesterol.

11. The lipid nanoparticle of claim 7, wherein the protein is selected from the group consisting of a nucleoprotein, a mucoprotein, a lipoprotein, a synthetic polypeptide, a small molecule linked to a protein, and a glycoprotein.

12. The lipid nanoparticle of claim 6, wherein the nucleic acid is in the form of a single stranded or partially double stranded oligomer or a polymer composed of ribonucleotides.

13. The lipid nanoparticle of claim 6, wherein the nucleic acid is selected from the group consisting of an miRNA, an antisense oligonucleotide, an siRNA, an immune-stimulatory oligonucleotide, an aptamer, a ribozyme, and a plasmid encoding a specific gene or siRNA.

14. A pharmaceutical composition comprising a cyclic amino-lipid according to claim 1.

15. A pharmaceutical composition comprising a lipid nanoparticle according to claim 2.

16. The pharmaceutical composition of claim 15, further comprising a biologically active compound.

17. The pharmaceutical composition of claim 16, wherein the biologically active compound is a nucleic acid.

18. The pharmaceutical composition of claim 17, wherein the nucleic acid is in the form of a single stranded or partially double stranded oligomer or a polymer composed of ribonucleotides.

19. A method of treating a disease that is caused by the over-expression of one or several proteins in a subject, said method comprising the administration of a lipid nanoparticle according to claim 5 to the subject, wherein the biologically active compound is a nucleic acid, and wherein treatment refers to alleviation of symptoms, decreasing the rate of disease progression, amelioration or palliation of the disease state, remission or improved prognosis, or slowing the progression of the disease.

20. A method of treating a disease that is caused by a reduced, suppressed or missing expression of one or several proteins in a subject, said method comprising administration of a lipid nanoparticle according to claim 5 to the subject, wherein the biologically active compound is a nucleic acid, and wherein treatment refers to alleviation of symptoms, decreasing the rate of disease progression, amelioration or palliation of the disease state, remission or improved prognosis, or slowing the progression of the disease.

21. A method for generating an immune response in a subject, said method comprising the administration of a lipid nanoparticle according to claim 5 to the subject, wherein the biologically active compound is an immune-stimulatory nucleic acid.

* * * * *

SEQUENCE LISTING

<160> NUMBER OF SEQ ID NOS: 226

<210> SEQ ID NO 1
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA targeting mouse Factor 7
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:

```
<221> NAME/KEY: modified_base
<222> LOCATION: 2, 8, 10, 12, 13, 16, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 9, 11, 14, 15, 19
<223> OTHER INFORMATION: /mod_base = "2'-hydroxy corresponding
      nucleoside"

<400> SEQUENCE: 1
gcaaaggcgu gccaacucat t                                              21

<210> SEQ ID NO 2
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA targeting mouse Factor 7
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 9
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 12, 13, 14, 15, 16, 17,
      18, 19
<223> OTHER INFORMATION: /mod_base = "2'-hydroxy corresponding
      nucleoside"

<400> SEQUENCE: 2
ugaguuggca cgccuuugct t                                              21

<210> SEQ ID NO 3
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA targeting EGFP
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 5, 6, 8, 10, 11, 13, 16, 17
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 7, 9, 12, 14, 15, 18, 19
<223> OTHER INFORMATION: /mod_base = "2'-hydroxy corresponding
      nucleoside"
```

<400> SEQUENCE: 3
acgucuauau cauggccgat t                                              21

<210> SEQ ID NO 4
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA targeting EGFP
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 6, 11, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 12, 14, 15, 16, 17, 18, 19
<223> OTHER INFORMATION: /mod_base = "2'-hydroxy corresponding
      nucleoside"

<400> SEQUENCE: 4
ucggccauga uauagacgut t                                              21

<210> SEQ ID NO 5
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA targeting EGFP
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 10, 12, 15, 16, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 11, 13, 14, 17, 19
<223> OTHER INFORMATION: /mod_base = "2'-hydroxy corresponding
      nucleoside"

<400> SEQUENCE: 5
aacgagaagc gcgaucacat t                                              21

<210> SEQ ID NO 6
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA targeting EGFP
<220> FEATURE:
<221> NAME/KEY: modified_base
<222> LOCATION: 1

```
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 6
ugugaucgcg cuucucguut t                                             21

<210> SEQ ID NO 7
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA targeting mouse Clec4f
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 3, 4, 5, 6, 7, 8, 10, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 9, 11, 12, 14, 15, 16, 17, 18, 19
<223> OTHER INFORMATION: /mod_base = "2'-hydroxy corresponding
      nucleoside"

<400> SEQUENCE: 7 cuuucucgu gacaagaagt t                                              21

<210> SEQ ID NO 8
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA targeting mouse Clec4f
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 9
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 12, 13, 14, 15, 16, 17,
      18, 19
<223> OTHER INFORMATION: /mod_base = "2'-hydroxy corresponding
      nucleoside"

<400> SEQUENCE: 8
```
cuucuuguca cgagaaaagt t                                              21

<210> SEQ ID NO 9
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA targeting mouse Reln
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 4, 5, 6, 10, 11, 13, 14, 15, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 7, 8, 9, 12, 16
<223> OTHER INFORMATION: /mod_base = "2'-hydroxy corresponding
      nucleoside"

<400> SEQUENCE: 9
ggucucaagc cacucguuut t                                              21

<210> SEQ ID NO 10
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA targeting mouse Reln
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 10
aaacgagugg cuugagacct t                                              21

<210> SEQ ID NO 11
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA targeting mouse Tek
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 6, 8, 11, 14, 15, 16, 18
<223> OTHER INFORMATION: /mod_base = "2'-O-methyl corresponding
      nucleoside"

```
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 9, 10, 12, 13, 17, 19
<223> OTHER INFORMATION: /mod_base = "2'-hydroxy corresponding
      nucleoside"

<400> SEQUENCE: 11
gaagaugcag ugauuuacat t                                              21

<210> SEQ ID NO 12
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA targeting mouse Tek
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 3, 8, 13
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 9, 10, 11, 12, 14, 15, 16, 17, 18,
      19
<223> OTHER INFORMATION: /mod_base = "2'-hydroxy corresponding
      nucleoside"

<400> SEQUENCE: 12
uguaaaucac ugcaucuuct t                                              21

<210> SEQ ID NO 13
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA targeting mouse CD68
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 9, 10, 11, 13, 14, 15, 16, 17, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 5, 6, 7, 8, 12
<223> OTHER INFORMATION: /mod_base = "2'-hydroxy corresponding
      nucleoside"

<400> SEQUENCE: 13
gcgcagaauu caucucuuct t                                              21
```

```
<210> SEQ ID NO 14
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA targeting mouse CD68
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
      nucleoside"

<400> SEQUENCE: 14
gaagagauga auucugcgct t                                              21

<210> SEQ ID NO 15
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA targeting mouse CD45
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 10, 11, 12, 13, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 7, 8, 9, 14, 15, 16, 17, 19
<223> OTHER INFORMATION: /mod_base = "2'-hydroxy corresponding
      nucleoside"

<400> SEQUENCE: 15
cuggcugaau uucagagcat t                                              21

<210> SEQ ID NO 16
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA targeting mouse CD45
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 13, 17
<223> OTHER INFORMATION: /mod_base = "2'-O-methyl corresponding
      nucleoside"
<220> FEATURE:
<221> NAME/KEY: modified_base
```

```
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 14, 15, 16, 18,
      19
<223> OTHER INFORMATION: /mod_base = "2'-hydroxy corresponding
      nucleoside"

<400> SEQUENCE: 16
ugcucugaaa uucagccagt t                                              21

<210> SEQ ID NO 17
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA targeting mouse Clec7A
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 4, 8, 10, 12, 13, 14, 17, 18
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 6, 7, 9, 11, 15, 16, 19
<223> OTHER INFORMATION: /mod_base = "2'-hydroxy corresponding
      nucleoside"

<400> SEQUENCE: 17
agauggauau acucaauuat t                                              21

<210> SEQ ID NO 18
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA targeting mouse Clec7A
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 9, 11, 15
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 8, 10, 12, 13, 14, 16, 17, 18, 19
<223> OTHER INFORMATION: /mod_base = "2'-hydroxy corresponding
      nucleoside"

<400> SEQUENCE: 18
uaauugagua uauccaucut t                                              21

<210> SEQ ID NO 19
```

```
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 19
gagagcaatg ccagcccctt tttctcttgg aaagaaagt                              39

<210> SEQ ID NO 20
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 20
ggtccagggt ttcttactcc ttgttttct cttggaaaga aagt                         44

<210> SEQ ID NO 21
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 21
ccctaggccc ctcctgttat ttttttctct tggaaagaaa gt                          42

<210> SEQ ID NO 22
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 22
tgcagcgaac tttattgatg gttttttctct tggaaagaaa gt                         42

<210> SEQ ID NO 23
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 23
gcacgtcaga tccacgacgt ttttaggcat aggacccgtg tct                         43

<210> SEQ ID NO 24
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 24
ggcaggtttc tccaggcgtt tttaggcata ggacccgtgt ct                          42

<210> SEQ ID NO 25
<211> LENGTH: 44
```

```
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 25
gccctcagat gcctgcttca tttttaggca taggacccgt gtct                    44

<210> SEQ ID NO 26
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 26
gccgtattca ttgtcatacc aggtttttag gcataggacc cgtgtct                 47

<210> SEQ ID NO 27
<211> LENGTH: 45
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 27
gtccaccacc ctgttgctgt attttaggc ataggacccg tgtct                    45

<210> SEQ ID NO 28
<211> LENGTH: 46
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 28
aattgtgagg gagatgctca gttttttagg cataggaccc gtgtct                  46

<210> SEQ ID NO 29
<211> LENGTH: 25
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 29
ccaccttctt gatgtcatca tactt                                         25

<210> SEQ ID NO 30
<211> LENGTH: 20
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 30
cccaagatgc ccttcagtgg                                               20

<210> SEQ ID NO 31
<211> LENGTH: 24
<212> TYPE: DNA
```

```
<213> ORGANISM: Artificial sequence
<220> FEATURE:
<223> OTHER INFORMATION: Description of the artificial sequence: bDNA
      probes for mouse GAPDH

<400> SEQUENCE: 31
gagacaacct ggtcctcagt gtag                                         24

<210> SEQ ID NO 32
<211> LENGTH: 22
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 32
ggagttgctg ttgaagtcgc ag                                           22

<210> SEQ ID NO 33
<211> LENGTH: 21
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 33
ggcatcgaag gtggaagagt g                                            21

<210> SEQ ID NO 34
<211> LENGTH: 25
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 34
aaatgagctt gacaaagttg tcatt                                        25

<210> SEQ ID NO 35
<211> LENGTH: 20
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 35
gaggccatgt aggccatgag                                              20

<210> SEQ ID NO 36
<211> LENGTH: 18
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 36
gtccttgctg gggtgggt                                                18

<210> SEQ ID NO 37
<211> LENGTH: 20
<212> TYPE: DNA
<213> ORGANISM: Artificial sequence
```

```
<220> FEATURE:
<223> OTHER INFORMATION: Description of the artificial sequence: bDNA
      probes for mouse GAPDH

<400> SEQUENCE: 37
tagggcctct cttgctcagt                                                    20

<210> SEQ ID NO 38
<211> LENGTH: 19
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 38
gttgggggcc gagttggga                                                     19

<210> SEQ ID NO 39
<211> LENGTH: 18
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 39 atggggtct gggatgga                                                       18

<210> SEQ ID NO 40
<211> LENGTH: 23
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 40
tattcaagag agtagggagg gct                                                23

<210> SEQ ID NO 41
<211> LENGTH: 40
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 41
gagaagcagc agcccatgct tttctcttg gaaagaaagt                                40

<210> SEQ ID NO 42
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 42
tggagctgga gcagaaagca ttttctctt ggaaagaaag t                              41

<210> SEQ ID NO 43
<211> LENGTH: 43
<212> TYPE: DNA
<213> ORGANISM: Artificial sequence
<220> FEATURE:
```

```
<223> OTHER INFORMATION: Description of the artificial sequence: bDNA
      probes for mouse Factor VII

<400> SEQUENCE: 43
tgcttcctcc tgggttatga aatttttctc ttggaaagaa agt                    43

<210> SEQ ID NO 44
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 44
ccgggccaaa gctcctcctt tttctcttgg aaagaaagt                         39

<210> SEQ ID NO 45
<211> LENGTH: 40
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 45
cttgaagatc tcccgggcct ttttctcttg gaaagaaagt                        40

<210> SEQ ID NO 46
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 46
ctgcttggtc ctctcagggc ttttttctct tggaaagaaa gt                     42

<210> SEQ ID NO 47
<211> LENGTH: 45
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 47
actgcagtcc ctagaggtcc cttttaggc ataggacccg tgtct                   45

<210> SEQ ID NO 48
<211> LENGTH: 46
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 48
tttgcctgtg taggacacca tgttttagg cataggaccc gtgtct                  46

<210> SEQ ID NO 49
<211> LENGTH: 45
<212> TYPE: DNA
<213> ORGANISM: Artificial sequence
<220> FEATURE:
<223> OTHER INFORMATION: Description of the artificial sequence: bDNA
``` probes for mouse Factor VII

<400> SEQUENCE: 49
tcctcaaagg agcactgttc cttttttaggc ataggacccg tgtct         45

<210> SEQ ID NO 50
<211> LENGTH: 49
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 50
ccccatcact gtaaacaatc cagaattttt aggcatagga cccgtgtct     49

<210> SEQ ID NO 51
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 51
tggattcgag gcacactggt tttttaggca taggacccgt gtct          44

<210> SEQ ID NO 52
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 52
tggcaggtac ctacgttctg acatttttag gcataggacc cgtgtct        47

<210> SEQ ID NO 53
<211> LENGTH: 46
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 53
cttgcttttc tcacagttcc gatttttagg cataggaccc gtgtct         46

<210> SEQ ID NO 54
<211> LENGTH: 19
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 54
aggagtgagt tggcacgcc                                       19

<210> SEQ ID NO 55
<211> LENGTH: 24
<212> TYPE: DNA
<213> ORGANISM: Artificial sequence
<220> FEATURE:
<223> OTHER INFORMATION: Description of the artificial sequence: bDNA
      probes for mouse Factor VII

```
<400> SEQUENCE: 55
tcattgcact ctctctccag agag                                          24

<210> SEQ ID NO 56
<211> LENGTH: 25
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 56
gcagacgtaa gacttgagat gatcc                                         25

<210> SEQ ID NO 57
<211> LENGTH: 23
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 57
ccctcaaagt ctaggaggca gaa                                           23

<210> SEQ ID NO 58
<211> LENGTH: 22
<212> TYPE: DNA
<213> ORGANISM: Artificial sequence
<220> FEATURE:
<223> OTHER INFORMATION: Description of the artificial sequence: bDNA
      probes for mouse Factor VII

<400> SEQUENCE: 58
ttgcacagat cagctgctca tt                                            22

<210> SEQ ID NO 59
<211> LENGTH: 37
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 59
ggcacgggca gcttgctttt tctcttggaa agaaagt                            37

<210> SEQ ID NO 60
<211> LENGTH: 40
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 60
ggtagcggct gaagcactgt ttttctcttg gaaagaaagt                         40

<210> SEQ ID NO 61
<211> LENGTH: 40
<212> TYPE: DNA
<213> ORGANISM: Artificial sequence
<220> FEATURE:
<223> OTHER INFORMATION: Description of the artificial sequence: bDNA
      probes for EGFP
```

```
<400> SEQUENCE: 61
cctggacgta gccttcgggt ttttctcttg gaaagaaagt                          40

<210> SEQ ID NO 62
<211> LENGTH: 42
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 62
ccttgaagaa gatggtgcgc tttttctct tggaaagaaa gt                        42

<210> SEQ ID NO 63
<211> LENGTH: 39
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 63
cgaacttcac ctcggcgctt tttctcttgg aaagaaagt                           39

<210> SEQ ID NO 64
<211> LENGTH: 39
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 64
ccttcagctc gatgcggttt tttctcttgg aaagaaagt                           39

<210> SEQ ID NO 65
<211> LENGTH: 42
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 65
gtcacgaggg tgggccagtt tttaggcata ggacccgtgt ct                       42

<210> SEQ ID NO 66
<211> LENGTH: 43
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 66
cacgccgtag gtcagggtgt ttttaggcat aggacccgtg tct                      43

<210> SEQ ID NO 67
<211> LENGTH: 44
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 67
```
gtgctgcttc atgtggtcgg tttttaggca taggacccgt gtct                44

<210> SEQ ID NO 68
<211> LENGTH: 42
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 68
tcaccagggt gtcgcccttt tttaggcata ggacccgtgt ct                  42

<210> SEQ ID NO 69
<211> LENGTH: 21
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 69
cggtggtgca gatgaacttc a                                         21

<210> SEQ ID NO 70
<211> LENGTH: 21
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 70
catggcggac ttgaagaagt c                                         21

<210> SEQ ID NO 71
<211> LENGTH: 21
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 71
cgtcctcctt gaagtcgatg c                                         21

<210> SEQ ID NO 72
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse
      Clec4f

<400> SEQUENCE: 72
ggtcccttct cagggtctgt aattttctc ttggaaagaa agt                  43

<210> SEQ ID NO 73
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 73
tctgtcttgg ccctctgaag attttttctc ttggaaagaa agt         43

<210> SEQ ID NO 74
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 74
ccccaggcga ttctgctctt tttctcttgg aaagaaagt              39

<210> SEQ ID NO 75
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 75
tctgctcctg cttctgtgca gttttctct tggaaagaaa gt           42

<210> SEQ ID NO 76
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 76
cagaacttct cagcctcccg ttttctctt ggaaagaaag t            41

<210> SEQ ID NO 77
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 77
tgcgctccct gggacgtatt tttctcttgg aaagaaagt              39

<210> SEQ ID NO 78
<211> LENGTH: 49
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 78
gacttcaaag ctgagacatc actcattttt aggcatagga cccgtgtct   49

<210> SEQ ID NO 79
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 79

```
gatctgcctt caaactctgc atcttttag gcataggacc cgtgtct         47
```

<210> SEQ ID NO 80
<211> LENGTH: 41
<212> TYPE: DNA
<213> ORGANISM: Artificial sequence
<220> FEATURE:
<223> OTHER INFORMATION: Description of the artificial sequence: bDNA
       probes for mouse Clec4f

<400> SEQUENCE: 80

```
ggctttggtc gcctgcattt ttaggcatag gacccgtgtc t             41
```

<210> SEQ ID NO 81
<211> LENGTH: 43
<212> TYPE: DNA
<213> ORGANISM: Artificial sequence
<220> FEATURE:
<223> OTHER INFORMATION: Description of the artificial sequence: bDNA
       probes for mouse Clec4f

<400> SEQUENCE: 81

```
ttccagttct gcgcgatcat ttttaggcat aggacccgtg tct           43
```

<210> SEQ ID NO 82
<211> LENGTH: 43
<212> TYPE: DNA
<213> ORGANISM: Artificial sequence
<220> FEATURE:
<223> OTHER INFORMATION: Description of the artificial sequence: bDNA
       probes for mouse Clec4f

<400> SEQUENCE: 82

```
agaggtcacc gaagccaggt ttttaggcat aggacccgtg tct           43
```

<210> SEQ ID NO 83
<211> LENGTH: 23
<212> TYPE: DNA
<213> ORGANISM: Artificial sequence
<220> FEATURE:
<223> OTHER INFORMATION: Description of the artificial sequence: bDNA
       probes for mouse Clec4f

<400> SEQUENCE: 83

```
tgctctgtag catctggaca ttg                                 23
```

<210> SEQ ID NO 84
<211> LENGTH: 21
<212> TYPE: DNA
<213> ORGANISM: Artificial sequence
<220> FEATURE:
<223> OTHER INFORMATION: Description of the artificial sequence: bDNA
       probes for mouse Clec4f

<400> SEQUENCE: 84

```
cccctgaatc ttggcagtga g                                   21
```

<210> SEQ ID NO 85
<211> LENGTH: 19
<212> TYPE: DNA
<213> ORGANISM: Artificial sequence
<220> FEATURE:
<223> OTHER INFORMATION: Description of the artificial sequence: bDNA
       probes for mouse Clec4f

<400> SEQUENCE: 85

```
ccacagcttc ctgcagggc                                      19
```

<210> SEQ ID NO 86
<211> LENGTH: 24
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 86
gctggagaac ctgattctga gtct                                          24

<210> SEQ ID NO 87
<211> LENGTH: 29
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 87
aaaagtaata aaagtttcca ttgaagtac                                     29

<210> SEQ ID NO 88
<211> LENGTH: 20
<212> TYPE: DNA
<213> ORGANISM: Artificial sequence
<220> FEATURE:
<223> OTHER INFORMATION: Description of the artificial sequence: bDNA
      probes for mouse Clec4f

<400> SEQUENCE: 88
ccacggcttc ttgtcacgag                                               20

<210> SEQ ID NO 89
<211> LENGTH: 45
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 89
cagagatctt gaactgcatg atcctttttc tcttggaaag aaagt                   45

<210> SEQ ID NO 90
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 90
tcggcgggta agcactgatt tttctcttgg aaagaaagt                          39

<210> SEQ ID NO 91
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 91
cgcttccaga acactttggg tttttctctt ggaaagaaag t                       41

<210> SEQ ID NO 92
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 92
ttcaggaagc gggtaggtga tttttctctt ggaaagaaag t                41

<210> SEQ ID NO 93
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 93
gtccatcatg gctgccacat ttttaggcat aggacccgtg tct              43

<210> SEQ ID NO 94
<211> LENGTH: 49
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 94
tcatgagtca ctgcatacac ctctctttt aggcatagga cccgtgtct         49

<210> SEQ ID NO 95
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 95
ttcaggcact ttgcatccaa tttttaggca taggaccccgt gtct            44

<210> SEQ ID NO 96
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 96
tgaatttgat tctgggcaat ttttttttag gcataggacc cgtgtct          47

<210> SEQ ID NO 97
<211> LENGTH: 48
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 97
gggactaaat aactccagct cacgttttta ggcataggac ccgtgtct         48

```
<210> SEQ ID NO 98
<211> LENGTH: 45
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 98 tcctttcca cccttcagtt gttttaggc ataggacccg tgtct                45

<210> SEQ ID NO 99
<211> LENGTH: 46
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 99
ttacaggatt ccccgttaag cttttttagg cataggaccc gtgtct              46

<210> SEQ ID NO 100
<211> LENGTH: 48
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 100
gggtcacaga tacactgttc ctttttttta ggcataggac ccgtgtct            48

<210> SEQ ID NO 101
<211> LENGTH: 26
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 101
agtcacagaa tctttccact gtacag                                    26

<210> SEQ ID NO 102
<211> LENGTH: 20
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 102
gagcatgaca ccatctggcg                                           20

<210> SEQ ID NO 103
<211> LENGTH: 20
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 103
agttctcagt gggcgtcagg                                           20

<210> SEQ ID NO 104
```

```
<211> LENGTH: 24
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 104
ccaaagtcag tagaaaactg cacg                                              24

<210> SEQ ID NO 105
<211> LENGTH: 24
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 105
ggaagaacac agacggttga gaaa                                              24

<210> SEQ ID NO 106
<211> LENGTH: 28
<212> TYPE: DNA
<213> ORGANISM: Artificial sequence
<220> FEATURE:
<223> OTHER INFORMATION: Description of the artificial sequence: bDNA
      probes for mouse Reln

<400> SEQUENCE: 106
tctgagtact tttggtagaa cctaaatc                                          28

<210> SEQ ID NO 107
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 107
tgagtccctg ggaagctttc attttctct tggaaagaaa gt                           42

<210> SEQ ID NO 108
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 108
acttccccag atctccccat tttttctctt ggaaagaaag t                           41

<210> SEQ ID NO 109
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 109
taagccggct aaagagtcca tttttctct tggaaagaaa gt                           42

<210> SEQ ID NO 110
<211> LENGTH: 41
```

```
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 110
aatgcaggtg agggatgttt tttttctctt ggaaagaaag t                           41

<210> SEQ ID NO 111
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 111
tcctatggtg atgggctcat ggttttctc ttggaaagaa agt                          43

<210> SEQ ID NO 112
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 112
ccgctcgcat ggtccacttt tttaggcata ggacccgtgt ct                          42

<210> SEQ ID NO 113
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 113
acaactcaca actttgcgac ttcttttag gcataggacc cgtgtct                      47

<210> SEQ ID NO 114
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 114
ccagcgtcca cagatgagca ttttttaggca taggacccgt gtct                       44

<210> SEQ ID NO 115
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 115
agcaagctga ctccacagag aactttttag gcataggacc cgtgtct                     47

<210> SEQ ID NO 116
<211> LENGTH: 48
<212> TYPE: DNA
```

<213> ORGANISM: Artificial sequence
<220> FEATURE:
<223> OTHER INFORMATION: Description of the artificial sequence: bDNA
      probes for mouse Tek

<400> SEQUENCE: 116
gcgccttcta ctactccata aaggtttta ggcataggac ccgtgtct                    48

<210> SEQ ID NO 117
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 117
cggcatcaga cacaagaggt aggttttag gcataggacc cgtgtct                     47

<210> SEQ ID NO 118
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 118
gggtgccacc cagaggcttt ttaggcatag gacccgtgtc t                          41

<210> SEQ ID NO 119
<211> LENGTH: 22
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 119
gcaaggagaa acaccacaga ag                                               22

<210> SEQ ID NO 120
<211> LENGTH: 22
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 120
cgctcttgtt tacaagttgg cg                                               22

<210> SEQ ID NO 121
<211> LENGTH: 24
<212> TYPE: DNA
<213> ORGANISM: Artificial sequence
<220> FEATURE:
<223> OTHER INFORMATION: Description of the artificial sequence: bDNA
      probes for mouse Tek

<400> SEQUENCE: 121
gaattgatca agatcaggtc catg                                             24

<210> SEQ ID NO 122
<211> LENGTH: 40
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 122
tgacgagttt tacaccgcga tttttgaag ttaccgtttt                               40

<210> SEQ ID NO 123
<211> LENGTH: 46
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 123
aatctgtctg cacatttata acatttttt ttctgagtca aagcat                        46

<210> SEQ ID NO 124
<211> LENGTH: 40
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 124
ggcgtttctg gaatccccat ttttctcttg gaaagaaagt                              40

<210> SEQ ID NO 125
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 125
tggatcccca caactaggct tatttttgaa gttaccgttt t                            41

<210> SEQ ID NO 126
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 126
agagactaac gtttttcttg cagcttttc tgagtcaaag cat                           43

<210> SEQ ID NO 127
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 127
gtttagatac aggctcaggc cattttctc ttggaaagaa agt                           43

<210> SEQ ID NO 128
<211> LENGTH: 41
<212> TYPE: DNA
<213> ORGANISM: Artificial sequence
<220> FEATURE:

```
<223> OTHER INFORMATION: Description of the artificial sequence: bDNA
      probes for mouse CD45

<400> SEQUENCE: 128
tggggtttag atgcagactc agtttttgaa gttaccgttt t                           41

<210> SEQ ID NO 129
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 129
attgttctta tagcataaaa catatccatt tttctgagtc aaagcat                     47

<210> SEQ ID NO 130
<211> LENGTH: 46
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 130
taggcaaact tttacatttt tctgattttt ctcttggaaa gaaagt                      46

<210> SEQ ID NO 131
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 131
ccacctcaaa actggtcaca ttatttttg aagttaccgt ttt                          43

<210> SEQ ID NO 132
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 132
tcatagtatt tataaggttt caagctttt tttctgagtc aaagcat                      47

<210> SEQ ID NO 133
<211> LENGTH: 24
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 133
ttgacatagg caagtaggga cact                                              24

<210> SEQ ID NO 134
<211> LENGTH: 43
<212> TYPE: DNA
<213> ORGANISM: Artificial sequence
<220> FEATURE:
<223> OTHER INFORMATION: Description of the artificial sequence: bDNA
```

```
        probes for mouse CD45

<400> SEQUENCE: 134
cccatttctt tgaatcttcc cattttctc ttggaaagaa agt                43

<210> SEQ ID NO 135
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 135
tgaaaattgc acttctcagc agtttttga agttaccgtt tt                 42

<210> SEQ ID NO 136
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 136
ccggacgatc tgcttttgtg tttttctgag tcaaagcat                    39

<210> SEQ ID NO 137
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 137
ggttttcatt ccattgacct tgttttttct cttggaaaga aagt              44

<210> SEQ ID NO 138
<211> LENGTH: 36
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 138
ttgtctgtcg gccgggattt ttgaagttac cgtttt                       36

<210> SEQ ID NO 139
<211> LENGTH: 46
<212> TYPE: DNA
<213> ORGANISM: Artificial sequence
<220> FEATURE:
<223> OTHER INFORMATION: Description of the artificial sequence: bDNA
      probes for mouse CD45

<400> SEQUENCE: 139
ggaggaccac atgtaacatt tatactattt ttctgagtca aagcat            46

<210> SEQ ID NO 140
<211> LENGTH: 46
<212> TYPE: DNA
<213> ORGANISM: Artificial sequence
<220> FEATURE:
<223> OTHER INFORMATION: Description of the artificial sequence: bDNA
      probes for mouse CD45
```

<400> SEQUENCE: 140
ggttttaggg ccattagttt cataattttt ctcttggaaa gaaagt                    46

<210> SEQ ID NO 141
<211> LENGTH: 40
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 141
cgaggctggc actgcacaat ttttctcttg gaaagaaagt                           40

<210> SEQ ID NO 142
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 142
cttcaccatt ttgtctacgg gatttttgaa gttaccgttt t                         41

<210> SEQ ID NO 143
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 143
ccaaatccgt tcacaccgac tttttctgag tcaaagcat                            39

<210> SEQ ID NO 144
<211> LENGTH: 38
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 144
ccaggcgccc aatacggttt ttctcttgga aagaaagt                             38

<210> SEQ ID NO 145
<211> LENGTH: 38
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 145
caaatggcag ccctggtgat ttttgaagtt accgtttt                             38

<210> SEQ ID NO 146
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse GAPDH -continued

<400> SEQUENCE: 146
aacaatctcc actttgccac tgttttctg agtcaaagca t         41

<210> SEQ ID NO 147
<211> LENGTH: 19
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 147
tgaaggggtc gttgatggc         19

<210> SEQ ID NO 148
<211> LENGTH: 26
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 148
catgtagacc atgtagttga ggtcaa         26

<210> SEQ ID NO 149
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 149
ccgtgagtgg agtcatactg gaattttct cttggaaaga aagt         44

<210> SEQ ID NO 150
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 150
ttgactgtgc cgttgaattt gttttctct tggaaagaaa gt         42

<210> SEQ ID NO 151
<211> LENGTH: 37
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 151
agcttcccat tctcggcctt tttgaagtta ccgtttt         37

<210> SEQ ID NO 152
<211> LENGTH: 38
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 152
gggcttcccg ttgatgacat ttttctgagt caaagcat                               38

<210> SEQ ID NO 153
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 153
cgctcctgga agatggtgat tttttctctt ggaaagaaag t                           41

<210> SEQ ID NO 154
<211> LENGTH: 23
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 154
cccatttgat gttagtgggg tct                                               23

<210> SEQ ID NO 155
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse GAPDH

<400> SEQUENCE: 155
atactcagca ccggcctcac tttttctctt ggaaagaaag t                           41

<210> SEQ ID NO 156
<211> LENGTH: 37
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 156
ctgggagccg ttggccttttt tctcttggaa agaaagt                               37

<210> SEQ ID NO 157
<211> LENGTH: 40
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 157
ggcttggagc tgaacacaag gttttttgaag ttaccgtttt                            40

<210> SEQ ID NO 158
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 158
ggtataggat tcggatttga atttgttttt ctgagtcaaa gcat                    44

<210> SEQ ID NO 159
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 159
acctttcttc caccctgaat tgttttctc ttggaaagaa agt                      43

<210> SEQ ID NO 160
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 160
tctttaagcc ccactttagc ttttttttga agttaccgtt tt                      42

<210> SEQ ID NO 161
<211> LENGTH: 38
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 161
acagatatgc cccaagcccT ttttctgagt caaagcat                           38

<210> SEQ ID NO 162
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 162
cttggttttg ttgggattca aattttgaa gttaccgttt t                        41

<210> SEQ ID NO 163
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 163
ccgtcacaac ctccctggac ttttctgag tcaaagcat                           39

<210> SEQ ID NO 164
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 164
agagacaggt ggggatgggt attttctct tggaaagaaa gt                       42

<210> SEQ ID NO 165
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 165
ggtaagctgt ccataaggaa atgagttttt gaagttaccg tttt                    44

<210> SEQ ID NO 166
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 166
tgtaggtcct gtttgaatcc aaattttct gagtcaaagc at                       42

<210> SEQ ID NO 167
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 167
ggtagactgt actcgggctc tgatttttct cttggaaaga aagt                    44

<210> SEQ ID NO 168
<211> LENGTH: 38
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 168
tccaccgcca tgtagtccat ttttgaagtt accgtttt                           38

<210> SEQ ID NO 169
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 169
cctgtgggaa ggacacattg tattttttct gagtcaaagc at                      42

<210> SEQ ID NO 170
<211> LENGTH: 40
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 170
ccatgaatgt ccactgtgct gttttgaag ttaccgtttt                          40

<210> SEQ ID NO 171
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 171
tctcgaagag atgaattctg cgttttctg agtcaaagca t                    41

<210> SEQ ID NO 172
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 172
cccaagggag cttggagctt tttctcttgg aaagaaagt                      39

<210> SEQ ID NO 173
<211> LENGTH: 21
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 173
tttccacagc agaagctttg g                                         21

<210> SEQ ID NO 174
<211> LENGTH: 23
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 174
ctggagaaag aactatgctt gca                                       23

<210> SEQ ID NO 175
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse CD68

<400> SEQUENCE: 175
agagagcagg tcaaggtgaa cagttttct cttggaaaga aagt                 44

<210> SEQ ID NO 176
<211> LENGTH: 37
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 176
ggctgaagca ctgcacgctt tttgaagtta ccgtttt                        37

<210> SEQ ID NO 177
<211> LENGTH: 39
<212> TYPE: DNA
<213> ORGANISM: Artificial sequence
<220> FEATURE:
<223> OTHER INFORMATION: Description of the artificial sequence: bDNA probes for EGFP

<400> SEQUENCE: 177
gaagtcgatg cccttcagct tttttctgag tcaaagcat         39

<210> SEQ ID NO 178
<211> LENGTH: 38
<212> TYPE: DNA
<213> ORGANISM: Artificial sequence
<220> FEATURE:
<223> OTHER INFORMATION: Description of the artificial sequence: bDNA probes for EGFP

<400> SEQUENCE: 178
ggatgttgcc gtcctccttt ttttgaagtt accgtttt          38

<210> SEQ ID NO 179
<211> LENGTH: 38
<212> TYPE: DNA
<213> ORGANISM: Artificial sequence
<220> FEATURE:
<223> OTHER INFORMATION: Description of the artificial sequence: bDNA probes for EGFP

<400> SEQUENCE: 179
tactccagct tgtgccccat ttttctgagt caaagcat          38

<210> SEQ ID NO 180
<211> LENGTH: 42
<212> TYPE: DNA
<213> ORGANISM: Artificial sequence
<220> FEATURE:
<223> OTHER INFORMATION: Description of the artificial sequence: bDNA probes for EGFP

<400> SEQUENCE: 180
agacgttgtg gctgttgtag ttgttttga agttaccgtt tt      42

<210> SEQ ID NO 181
<211> LENGTH: 40
<212> TYPE: DNA
<213> ORGANISM: Artificial sequence
<220> FEATURE:
<223> OTHER INFORMATION: Description of the artificial sequence: bDNA probes for EGFP

<400> SEQUENCE: 181
tctgcttgtc ggccatgata tttttctga gtcaaagcat         40

<210> SEQ ID NO 182
<211> LENGTH: 41
<212> TYPE: DNA
<213> ORGANISM: Artificial sequence
<220> FEATURE:
<223> OTHER INFORMATION: Description of the artificial sequence: bDNA probes for EGFP

<400> SEQUENCE: 182
aagttcacct tgatgccgtt cttttttgaa gttaccgttt t       41

<210> SEQ ID NO 183

```
<211> LENGTH: 39
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 183
cgatgttgtg gcggatcttg tttttctgag tcaaagcat                               39

<210> SEQ ID NO 184
<211> LENGTH: 38
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 184
ctgcacgctg ccgtcctttt ttctcttgga aagaaagt                                38

<210> SEQ ID NO 185
<211> LENGTH: 19
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 185
gctggtagtg gtcggcgag                                                    19

<210> SEQ ID NO 186
<211> LENGTH: 18
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 186
cgccgatggg ggtgttct                                                     18

<210> SEQ ID NO 187
<211> LENGTH: 39
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 187
cttcatgtgg tcggggtagc tttttctgag tcaaagcat                              39

<210> SEQ ID NO 188
<211> LENGTH: 15
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 188
gcagcacggg gccgt                                                        15

<210> SEQ ID NO 189
<211> LENGTH: 20
```

<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 189
caggtagtgg ttgtcgggca                                                    20

<210> SEQ ID NO 190
<211> LENGTH: 38
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 190
agggcggact gggtgctttt ttctcttgga aagaaagt                                38

<210> SEQ ID NO 191
<211> LENGTH: 20
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 191
tctcgttggg gtctttgctc                                                    20

<210> SEQ ID NO 192
<211> LENGTH: 40
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 192
aggaccatgt gatcgcgctt ttttctcttg gaaagaaagt                              40

<210> SEQ ID NO 193
<211> LENGTH: 39
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 193
gcggtcacga actccagctt tttctcttgg aaagaaagt                               39

<210> SEQ ID NO 194
<211> LENGTH: 22
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 194
cggacttgaa gaagtcgtgc tg                                                 22

<210> SEQ ID NO 195
<211> LENGTH: 39
<212> TYPE: DNA

<213> ORGANISM: Artificial sequence
<220> FEATURE:
<223> OTHER INFORMATION: Description of the artificial sequence: bDNA
      probes for EGFP

<400> SEQUENCE: 195
cgtagccttc gggcatggtt tttctcttgg aaagaaagt                    39

<210> SEQ ID NO 196
<211> LENGTH: 38
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 196
aagatggtgc gctcctggat ttttgaagtt accgtttt                     38

<210> SEQ ID NO 197
<211> LENGTH: 39
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 197
agttgccgtc gtccttgaag tttttctgag tcaaagcat                    39

<210> SEQ ID NO 198
<211> LENGTH: 16
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 198
tcggcgcggg tcttgt                                             16

<210> SEQ ID NO 199
<211> LENGTH: 40
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 199
gtcgccctcg aacttcacct ttttctcttg gaaagaaagt                   40

<210> SEQ ID NO 200
<211> LENGTH: 38
<212> TYPE: DNA
<213> ORGANISM: Artificial sequence
<220> FEATURE:
<223> OTHER INFORMATION: Description of the artificial sequence: bDNA
      probes for EGFP

<400> SEQUENCE: 200
cgatgcggtt caccagggtt ttttgaagtt accgtttt                     38

<210> SEQ ID NO 201
<211> LENGTH: 38
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 201
tttctctgat cccctgggct ttttgaagtt accgtttt                              38

<210> SEQ ID NO 202
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 202
gaagatggag cctggcttcc tttttctgag tcaaagcat                             39

<210> SEQ ID NO 203
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 203
gcaatgggcc tccaaggttt tttctcttgg aaagaaagt                             39

<210> SEQ ID NO 204
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 204
gcacaggatt cctaaaccca cttttttgaa gttaccgttt t                          41

<210> SEQ ID NO 205
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 205
gcagcaacca ctactaccac aaattttttct gagtcaaagc at                        42

<210> SEQ ID NO 206
<211> LENGTH: 40
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 206
tgctagggca cccagcactt ttttctcttg gaaagaaagt                            40

<210> SEQ ID NO 207
<211> LENGTH: 39
<212> TYPE: DNA
<213> ORGANISM: Artificial sequence
<220> FEATURE:

```
<223> OTHER INFORMATION: Description of the artificial sequence: bDNA
      probes for mouse Clec7a

<400> SEQUENCE: 207
cctgaattgt gtcgccaaaa tttttgaagt taccgtttt                              39

<210> SEQ ID NO 208
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 208
ttgtctttct cctctggatt tctcttttc tgagtcaaag cat                          43

<210> SEQ ID NO 209
<211> LENGTH: 48
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 209
tggttctctt tatttcttga taggaagttt ttctcttgga aagaaagt                    48

<210> SEQ ID NO 210
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 210
ctaaagatga ttctgtgggc ttgttttga agttaccgtt tt                           42

<210> SEQ ID NO 211
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 211
ggagggagcc accttctcat tttttctgag tcaaagcat                              39

<210> SEQ ID NO 212
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 212
ctcctgtagt ttgggatgcc tttttttctc ttggaaagaa agt                         43

<210> SEQ ID NO 213
<211> LENGTH: 41
<212> TYPE: DNA
<213> ORGANISM: Artificial sequence
<220> FEATURE:
<223> OTHER INFORMATION: Description of the artificial sequence: bDNA
``` probes for mouse Clec7a

<400> SEQUENCE: 213
ggaaggcaag gctgagaaaa acttttttgaa gttaccgttt t            41

<210> SEQ ID NO 214
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 214
cttcccatgc atgatccaat tatttttctg agtcaaagca t            41

<210> SEQ ID NO 215
<211> LENGTH: 47
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 215
cctgagaagc taaataggta acagcttttt tctcttggaa agaaagt        47

<210> SEQ ID NO 216
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 216
tctcttactt ccataccagg aatttttttt gaagttaccg tttt          44

<210> SEQ ID NO 217
<211> LENGTH: 39
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 217
gcacctagct gggagcagtg tttttctgag tcaaagcat              39

<210> SEQ ID NO 218
<211> LENGTH: 28
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 218
ttttgagttg tctatcttca gtagatga                        28

<210> SEQ ID NO 219
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 219
tggctttcaa tgaactcaaa ttcttttct cttggaaaga aagt                            44

<210> SEQ ID NO 220
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 220
gcattaatac ggtgagacga tgttttttg aagttaccgt ttt                              43

<210> SEQ ID NO 221
<211> LENGTH: 40
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 221
cgggaaaggc ctatccaaaa tttttctga gtcaaagcat                                  40

<210> SEQ ID NO 222
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 222
catggccctt cactctgatt gttttctct tggaaagaaa gt                               42

<210> SEQ ID NO 223
<211> LENGTH: 42
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 223
gctgatccat cctcccagaa cttttctct tggaaagaaa gt                               42

<210> SEQ ID NO 224
<211> LENGTH: 43
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 224
ttgaaacgag ttggggaaga attttttctc ttggaaagaa agt                             43

<210> SEQ ID NO 225
<211> LENGTH: 41
<212> TYPE: DNA
<213> ORGANISM: Artificial sequence
<220> FEATURE:
<223> OTHER INFORMATION: Description of the artificial sequence: bDNA
      probes for mouse Clec7a

```
<400> SEQUENCE: 225
cctggggagc tgtatttctg actttttgaa gttaccgttt t                    41

<210> SEQ ID NO 226
<211> LENGTH: 44
<212> TYPE: DNA
<213> ORGANISM: Artificial sequence
<220> FEATURE:
<223> OTHER INFORMATION: Description of the artificial sequence: bDNA
      probes for mouse Clec7a

<400> SEQUENCE: 226
catacacaat tgtgcagtaa gcttttttt ctgagtcaaa gcat                  44
```